(12) United States Patent
Rosenbluth et al.

(10) Patent No.: US 12,741,137 B2
(45) **Date of Patent: *Sep. 22, 2026**

(54) DEVICES AND METHODS FOR CONTROLLING TREMOR

(71) Applicant: Cala Health, Inc., San Mateo, CA (US)

(72) Inventors: Kathryn H. Rosenbluth, San Francisco, CA (US); Scott Lee Delp, Stanford, CA (US); John Paderi, San Francisco, CA (US); Vijaykumar Rajasekhar, San Francisco, CA (US); Tahel Altman, San Francisco, CA (US)

(73) Assignee: Cala Health, Inc., San Mateo, CA (US)

( * ) Notice: Subject to any disclaimer, the term of this patent is extended or adjusted under 35 U.S.C. 154(b) by 166 days.

This patent is subject to a terminal disclaimer.

(21) Appl. No.: 18/934,053

(22) Filed: Oct. 31, 2024

(65) Prior Publication Data

US 2026/0115455 A1 Apr. 30, 2026

Related U.S. Application Data

(63) Continuation of application No. 17/107,435, filed on Nov. 30, 2020, now Pat. No. 12,161,858, which is a (Continued)

(51) Int. Cl.
*A61N 1/04* (2006.01)
*A61B 5/11* (2006.01)

(Continued)

(52) U.S. Cl.
CPC .......... *A61N 1/0456* (2013.01); *A61B 5/1101* (2013.01); *A61N 1/025* (2013.01);

(Continued)

(58) Field of Classification Search
None
See application file for complete search history.

(56) References Cited

U.S. PATENT DOCUMENTS 3,204,637 A 9/1965 Frank et al.
3,870,051 A 3/1975 Brindley (Continued)

FOREIGN PATENT DOCUMENTS

CN 1135722 11/1996
CN 1547483 11/2004

(Continued)

OTHER PUBLICATIONS

U.S. Appl. No. 15/277,946, filed Sep. 27, 2016, Rosenbluth et al.

(Continued)

*Primary Examiner* — Erica S Lee
(74) *Attorney, Agent, or Firm* — Knobbe Martens Olson & Bear LLP

(57) ABSTRACT

A peripheral nerve stimulator can be used to stimulate a peripheral nerve to treat essential tremor, Parkinson tremor, and other forms of tremor. The peripheral nerve stimulator can be either a noninvasive surface stimulator or an implanted stimulator. Stimulation can be electrical, mechanical, or chemical. Stimulation can be delivered using either an open loop system or a closed loop system with feedback.

20 Claims, 28 Drawing Sheets

Related U.S. Application Data continuation of application No. 15/277,946, filed on Sep. 27, 2016, now Pat. No. 10,850,090, which is a continuation of application No. 14/805,385, filed on Jul. 21, 2015, now Pat. No. 9,452,287, which is a continuation of application No. PCT/US2014/012388, filed on Jan. 21, 2014.

(60) Provisional application No. 61/857,248, filed on Jul. 23, 2013, provisional application No. 61/822,215, filed on May 10, 2013, provisional application No. 61/815,919, filed on Apr. 25, 2013, provisional application No. 61/786,549, filed on Mar. 15, 2013, provisional application No. 61/754,945, filed on Jan. 21, 2013.

(51) Int. Cl.
*A61N 1/02* (2006.01)
*A61N 1/18* (2006.01)
*A61N 1/36* (2006.01)

(52) U.S. Cl.
CPC ......... *A61N 1/0476* (2013.01); *A61N 1/0492* (2013.01); *A61N 1/18* (2013.01); *A61N 1/36031* (2017.08); *A61N 1/36034* (2017.08); *A61N 1/36067* (2013.01); *A61N 1/36167* (2013.01); *A61N 1/36178* (2013.01); *A61N 1/36196* (2013.01)

(56) References Cited

U.S. PATENT DOCUMENTS 4,103,808 A 8/1978 Hallman et al.
4,233,986 A 11/1980 Tannenbaum
4,300,575 A 11/1981 Wilson
4,313,441 A 2/1982 Buffet
4,458,696 A 7/1984 Larimore
4,461,075 A 7/1984 Bailey
4,539,996 A 9/1985 Engel
4,569,351 A 2/1986 Tang
4,582,049 A 4/1986 Ylvisaker
4,729,377 A 3/1988 Granek et al.
4,739,764 A 4/1988 Lue et al.
4,763,659 A 8/1988 Dunseath, Jr.
4,769,881 A 9/1988 Pedigo et al.
4,771,779 A 9/1988 Tanagho et al.
4,917,092 A 4/1990 Todd et al.
4,981,146 A 1/1991 Bertolucci
4,982,432 A 1/1991 Clark et al.
4,996,987 A 3/1991 Petrofsky
5,003,978 A 4/1991 Dunseath, Jr.
5,052,391 A 10/1991 Silverstone et al.
5,070,862 A 12/1991 Berlant
5,137,507 A 8/1992 Park
5,330,516 A 7/1994 Nathan
5,395,398 A 3/1995 Rogozinski
5,397,338 A 3/1995 Grey et al.
5,433,735 A 7/1995 Zanakis et al.
5,514,175 A 5/1996 Kim et al.
5,540,235 A 7/1996 Wilson
5,562,707 A 10/1996 Prochazka et al.
5,562,717 A 10/1996 Tippey et al.
5,573,011 A 11/1996 Felsing
5,575,294 A 11/1996 Perry et al.
5,606,968 A 3/1997 Mang
5,643,173 A 7/1997 Welles
5,775,331 A 7/1998 Raymond et al.
5,833,709 A 11/1998 Rise et al.
5,833,716 A 11/1998 Bar-Or et al.
5,899,922 A 5/1999 Loos
5,961,542 A 10/1999 Agarwala
6,016,449 A 1/2000 Fischell et al.
6,076,018 A 6/2000 Sturman et al.
6,081,744 A 6/2000 Loos
6,161,044 A 12/2000 Silverstone
6,178,352 B1 1/2001 Gruzdowich et al.
6,351,674 B2 2/2002 Silverstone
6,364,841 B1 4/2002 White et al.
6,366,813 B1 4/2002 DiLorenzo
6,366,814 B1 4/2002 Boveja et al.
6,419,644 B1 7/2002 White et al.
6,445,955 B1 9/2002 Michelson et al.
6,449,512 B1 9/2002 Boveja
6,453,204 B1 9/2002 Rhoads
6,505,074 B2 1/2003 Boveja et al.
6,546,290 B1 4/2003 Shloznikov
6,564,103 B2 5/2003 Fischer et al.
6,572,555 B2 6/2003 White et al.
6,579,270 B2 6/2003 Sussman et al.
6,641,546 B2 11/2003 White et al.
6,652,449 B1 11/2003 Gross et al.
6,662,052 B1 12/2003 Sarwal et al.
6,678,548 B1 1/2004 Echauz et al.
6,701,185 B2 3/2004 Burnett et al.
6,704,603 B1 3/2004 Gesotti
6,731,987 B1 5/2004 McAdams et al.
6,735,474 B1 5/2004 Loeb et al.
6,735,480 B2 5/2004 Giuntoli et al.
6,788,976 B2 9/2004 Gesotti
6,819,956 B2 11/2004 DiLorenzo
6,827,693 B2 12/2004 White et al.
6,829,510 B2 12/2004 Nathan et al.
6,836,684 B1 12/2004 Rijkhoff et al.
6,862,480 B2 3/2005 Cohen et al.
6,892,098 B2 5/2005 Ayal et al.
6,937,905 B2 8/2005 Carroll et al.
6,959,215 B2 10/2005 Gliner et al.
6,959,216 B2 10/2005 Faghri
6,988,005 B2 1/2006 McGraw et al.
7,010,352 B2 3/2006 Hogan
7,089,061 B2 8/2006 Grey
7,146,220 B2 12/2006 Dar et al.
7,162,305 B2 1/2007 Tong et al.
7,171,266 B2 1/2007 Gruzdowich et al.
7,177,694 B2 2/2007 Elbaum
7,177,703 B2 2/2007 Boveja et al.
7,209,787 B2 4/2007 DiLorenzo
7,228,178 B2 6/2007 Carroll et al.
7,231,254 B2 6/2007 DiLorenzo
7,236,830 B2 6/2007 Gliner
7,254,444 B2 8/2007 Moore et al.
7,277,758 B2 10/2007 DiLorenzo
7,283,866 B2 10/2007 Mumford et al.
7,324,851 B1 1/2008 DiLorenzo
7,326,235 B2 2/2008 Edwards
7,328,068 B2 2/2008 Spinelli et al.
7,349,739 B2 3/2008 Harry et al.
7,353,064 B2 4/2008 Gliner et al.
7,369,896 B2 5/2008 Gesotti
7,499,747 B2 3/2009 Kieval et al.
7,529,582 B1 5/2009 DiLorenzo
7,558,610 B1 7/2009 Odderson
7,636,602 B2 12/2009 Baru Fassio et al.
7,640,052 B2 12/2009 Weinstock
7,643,880 B2 1/2010 Tanagho et al.
7,643,882 B2 1/2010 Boston
7,647,112 B2 1/2010 Tracey et al.
7,650,190 B2 1/2010 Zhou et al.
7,657,317 B2 2/2010 Thacker et al.
7,660,632 B2 2/2010 Kirby et al.
7,742,820 B2 6/2010 Wyler et al.
7,761,166 B2 7/2010 Giftakis et al.
7,769,464 B2 8/2010 Gerber et al.
7,801,585 B1 9/2010 Weinstock
7,857,771 B2 12/2010 Alwan et al.
7,899,527 B2 3/2011 Yun et al.
7,899,556 B2 3/2011 Nathan et al.
7,917,201 B2 3/2011 Gozani et al.
7,930,034 B2 4/2011 Gerber
7,949,403 B2 5/2011 Palermo et al.
7,957,814 B2 6/2011 Goetz et al.
7,974,696 B1 7/2011 DiLorenzo

(56) References Cited

U.S. PATENT DOCUMENTS 7,974,698 B2 7/2011 Tass et al.
7,991,476 B2 8/2011 Nachum
7,996,088 B2 8/2011 Marrosu et al.
7,998,092 B2 8/2011 Avni
8,000,796 B2 8/2011 Tass
8,025,632 B2 9/2011 Einarsson
8,046,083 B2 10/2011 Al.
8,064,988 B2 11/2011 Weinstock
8,075,499 B2 12/2011 Nathan et al.
8,086,318 B2 12/2011 Strother et al.
8,108,047 B2 1/2012 Schumann
8,121,694 B2 2/2012 Molnar et al.
8,145,316 B2 3/2012 Deem et al.
8,165,668 B2 4/2012 Dacey, Jr. et al.
8,165,685 B1 4/2012 Knutson et al.
8,170,658 B2 5/2012 Dacey, Jr. et al.
8,175,718 B2 5/2012 Wahlgren et al.
8,187,209 B1 5/2012 Guiffrida et al.
8,190,249 B1 5/2012 Gharieb et al.
8,195,287 B2 6/2012 Dacey, Jr. et al.
8,209,036 B2 6/2012 Nathan et al.
8,219,188 B2 7/2012 Craig
8,233,988 B2 7/2012 Errico et al.
8,260,439 B2 9/2012 Diubaldi et al.
8,265,763 B2 9/2012 Fahey
8,280,513 B2 10/2012 Tehrani et al.
8,301,215 B2 10/2012 Lee
8,306,624 B2 11/2012 Gerber et al.
8,308,665 B2 11/2012 Harry et al.
8,313,443 B2 11/2012 Tom
8,326,398 B2 12/2012 Weinstock
8,326,432 B2 12/2012 Kalisek
8,343,026 B2 1/2013 Gardiner et al.
8,364,257 B2 1/2013 Van Den Eerenbeemd et al.
8,374,701 B2 2/2013 Hyde et al.
8,380,314 B2 2/2013 Panken et al.
8,382,688 B2 2/2013 Dar et al.
8,391,970 B2 3/2013 Tracey et al.
8,396,556 B2 3/2013 Libbus et al.
8,406,841 B2 3/2013 Lin et al.
8,409,116 B2 4/2013 Wang et al.
8,412,338 B2 4/2013 Faltys
8,414,507 B2 4/2013 Asada
8,417,351 B2 4/2013 Kilger
8,428,719 B2 4/2013 Napadow
8,430,805 B2 4/2013 Burnett et al.
8,435,166 B2 5/2013 Burnett et al.
8,447,411 B2 5/2013 Skelton et al.
8,452,410 B2 5/2013 Emborg et al.
8,463,374 B2 6/2013 Hudson et al.
8,467,876 B2 6/2013 Tehrani
8,473,064 B2 6/2013 Castel et al.
8,504,161 B1 8/2013 Kornet et al.
8,538,512 B1 9/2013 Bibian et al.
8,548,594 B2 10/2013 Thimineur et al.
8,571,687 B2 10/2013 Libbus et al.
8,581,731 B2 11/2013 Purks et al.
8,583,238 B1 11/2013 Heldman et al.
8,588,884 B2 11/2013 Hegde et al.
8,588,917 B2 11/2013 Whitehurst et al.
8,588,919 B2 11/2013 Li
8,608,671 B2 12/2013 Kinoshita et al.
8,626,305 B2 1/2014 Nielsen et al.
8,639,342 B2 1/2014 Possover
8,644,904 B2 2/2014 Chang et al.
8,644,921 B2 2/2014 Wilson
8,644,938 B2 2/2014 Craggs
8,660,644 B2 2/2014 Jaxx et al.
8,660,653 B2 2/2014 Kothandaraman et al.
8,660,656 B2 2/2014 Moser et al.
8,666,496 B2 3/2014 Simon et al.
8,679,038 B1 3/2014 Giuffrida
8,682,441 B2 3/2014 De Ridder
8,688,220 B2 4/2014 Degiorgio et al.
8,694,104 B2 4/2014 Libbus et al.
8,694,110 B2 4/2014 Nathan et al.
8,702,584 B2 4/2014 Rigaux et al.
8,702,629 B2 4/2014 Giuffrida et al.
8,706,241 B2 4/2014 Firlik et al.
8,718,780 B2 5/2014 Lee
8,729,129 B2 5/2014 Tracey et al.
8,738,143 B2 5/2014 Tucker et al.
8,740,825 B2 6/2014 Ehrenreich et al.
8,744,587 B2 6/2014 Miesel et al.
8,755,889 B2 6/2014 Scheiner
8,755,892 B2 6/2014 Amurthur et al.
D709,874 S 7/2014 Aumiller et al.
8,768,452 B2 7/2014 Gerber
8,788,045 B2 7/2014 Gross et al.
8,788,049 B2 7/2014 Lasko et al.
8,792,977 B2 7/2014 Kakei et al.
8,798,698 B2 8/2014 Kim et al.
8,821,416 B2 9/2014 Johansson et al.
8,825,163 B2 9/2014 Grill et al.
8,825,165 B2 9/2014 Possover
8,825,166 B2 9/2014 John
8,843,201 B1 9/2014 Heldman et al.
8,845,494 B2 9/2014 Whitall et al.
8,845,557 B1 9/2014 Giuffrida et al.
8,849,371 B2 9/2014 Weinstock
8,855,775 B2 10/2014 Leyde
8,862,238 B2 10/2014 Rahimi et al.
8,862,247 B2 10/2014 Schoendorf et al.
8,868,177 B2 10/2014 Simon et al.
8,874,227 B2 10/2014 Simon et al.
8,880,175 B2 11/2014 Simon
8,886,321 B2 11/2014 Rohrer et al.
8,892,200 B2 11/2014 Wagner et al.
8,897,870 B2 11/2014 De Ridder
8,903,494 B2 12/2014 Goldwasser et al.
8,920,345 B2 12/2014 Greenberg et al.
8,923,970 B2 12/2014 Bar-Yoseph et al.
8,923,971 B2 12/2014 Haefner et al.
8,948,876 B2 2/2015 Gozani et al.
8,958,884 B2 2/2015 Kothandaraman et al.
8,961,439 B2 2/2015 Yang et al.
8,972,017 B2 3/2015 Dar et al.
8,989,861 B2 3/2015 Su et al.
9,002,477 B2 4/2015 Burnett
9,005,102 B2 4/2015 Burnett et al.
9,008,781 B2 4/2015 Ahmed
9,011,310 B2 4/2015 Ahmed
9,017,273 B2 4/2015 Burbank et al.
9,026,216 B2 5/2015 Rossi et al.
9,042,988 B2 5/2015 Dilorenzo
9,044,587 B2 6/2015 Bachinski et al.
9,060,747 B2 6/2015 Salorio
9,079,029 B2 7/2015 Weinstock
9,089,691 B2 7/2015 Libbus et al.
9,095,351 B2 8/2015 Sachs et al.
9,095,417 B2 8/2015 Dar et al.
9,107,614 B2 8/2015 Halkias et al.
9,119,964 B2 9/2015 Marnfeldt
9,155,885 B2 10/2015 Wei et al.
9,155,890 B2 10/2015 Guntinas-Lichius et al.
9,162,059 B1 10/2015 Lindenthaler
9,168,374 B2 10/2015 Su
9,174,045 B2 11/2015 Simon et al.
9,186,095 B2 11/2015 Machado et al.
9,186,511 B2 11/2015 Bolea
9,192,763 B2 11/2015 Gerber et al.
9,211,409 B2 12/2015 Tracey et al.
9,211,417 B2 12/2015 Giuffrida et al.
9,220,431 B2 12/2015 Holzhacker
9,220,895 B2 12/2015 Siff et al.
9,227,056 B1 1/2016 Heldman et al.
9,238,137 B2 1/2016 Einav et al.
9,238,142 B2 1/2016 Heldman et al.
9,242,085 B2 1/2016 Hershey et al.
9,242,091 B2 1/2016 Bachinski et al.
9,248,285 B2 2/2016 Haessler
9,248,286 B2 2/2016 Simon et al.
9,248,297 B2 2/2016 Hoyer et al.
9,254,382 B2 2/2016 Ahmad et al.

(56) References Cited

U.S. PATENT DOCUMENTS 9,259,573 B2 2/2016 Tehrani et al.
9,259,577 B2 2/2016 Kaula et al.
9,265,927 B2 2/2016 Yonce et al.
9,282,928 B1 3/2016 Giffrida
9,289,603 B1 3/2016 Giuffrida et al.
9,289,607 B2 3/2016 Su et al.
9,301,712 B2 4/2016 McNames et al.
9,302,046 B1 4/2016 Giuffrida et al.
9,302,117 B2 4/2016 De Vincentiis
9,311,686 B2 4/2016 Roush et al.
9,314,190 B1 4/2016 Giuffrida et al.
9,314,622 B2 4/2016 Embrey et al.
9,332,918 B1 5/2016 Buckley et al.
9,339,213 B2 5/2016 Otsamo et al.
9,339,641 B2 5/2016 Rajguru et al.
9,345,872 B2 5/2016 Groteke
9,364,657 B2 6/2016 Kiani et al.
9,364,672 B2 6/2016 Marnfeldt
9,375,570 B2 6/2016 Kiani et al.
9,387,338 B2 7/2016 Burnett
9,393,418 B2 7/2016 Giuffrida et al.
9,393,430 B2 7/2016 Demers et al.
9,403,013 B2 8/2016 Walker et al.
9,408,683 B2 8/2016 St. Anne et al.
9,414,776 B2 8/2016 Sillay et al.
9,415,205 B2 8/2016 Lasko et al.
D767,436 S 9/2016 Goodner et al.
9,452,287 B2 9/2016 Rosenbluth et al.
9,468,753 B2 10/2016 Fisher et al.
9,474,898 B2 10/2016 Gozani et al.
9,522,278 B1 12/2016 Giuffrida et al.
9,533,154 B2 1/2017 Kothandaraman et al.
9,549,872 B2 1/2017 Chen et al.
9,550,068 B2 1/2017 Weinstock
9,581,972 B1 2/2017 Arrow et al.
9,586,038 B1 3/2017 Kosierkiewicz
9,589,698 B2 3/2017 Anhalt et al.
9,597,509 B2 3/2017 Hoffer et al.
9,610,442 B2 4/2017 Yoo et al.
9,610,459 B2 4/2017 Burnett et al.
9,615,797 B2 4/2017 John
9,630,004 B2 4/2017 Rajguru et al.
9,649,486 B2 5/2017 Holzhacker
9,656,070 B2 5/2017 Gozani et al.
9,662,490 B2 5/2017 Tracey et al.
9,662,502 B2 5/2017 Giuffrida et al.
9,669,211 B2 6/2017 Wijting et al.
9,675,800 B2 6/2017 Li et al.
9,675,801 B2 6/2017 Kong et al.
9,682,235 B1 6/2017 O'Mahony et al.
9,707,393 B2 7/2017 Hsueh et al.
9,717,920 B1 8/2017 Giuffrida et al.
9,717,921 B2 8/2017 Perryman et al.
9,731,126 B2 8/2017 Ferree et al.
9,757,584 B2 9/2017 Burnett
9,776,005 B2 10/2017 Meyyappan et al.
9,782,122 B1 10/2017 Giuffrida et al.
9,782,584 B2 10/2017 Cartledge et al.
9,802,041 B2 10/2017 Wong et al.
9,802,046 B2 10/2017 Grill et al.
9,826,921 B2 11/2017 Griffiths et al.
9,861,283 B1 1/2018 Giuffrida
9,861,817 B2 1/2018 Cho et al.
9,877,679 B1 1/2018 Giuffrida
9,877,680 B1 1/2018 Giuffrida et al.
9,878,158 B2 1/2018 Hershey et al.
9,884,179 B2 2/2018 Bouton et al.
9,901,299 B2 2/2018 Haviv et al.
9,907,960 B2 3/2018 Lian et al.
9,924,899 B2 3/2018 Pracar et al.
9,956,132 B2 5/2018 Francois et al.
9,956,395 B2 5/2018 Bikson et al.
9,962,549 B2 5/2018 Kothandaraman et al.
9,974,478 B1 5/2018 Brokaw et al.
9,980,659 B2 5/2018 Sadeghian-Motahar et al.
9,987,488 B1 6/2018 Gelfand et al.
9,992,918 B2 6/2018 Watanabe et al.
10,004,900 B2 6/2018 Kent et al.
10,016,600 B2 7/2018 Creasey et al.
10,022,545 B1 7/2018 Giuffrida
10,028,695 B2 7/2018 Machado et al.
10,039,928 B2 8/2018 Hyde et al.
10,045,740 B2 8/2018 John
10,046,161 B2 8/2018 Biasiucci et al.
D828,351 S 9/2018 Xi et al.
10,076,656 B2 9/2018 Dar et al.
10,080,885 B2 9/2018 Nathan et al.
10,085,670 B2 10/2018 Crosson et al.
10,085,689 B1 10/2018 Giuffrida et al.
10,092,754 B1 10/2018 Giuffrida et al.
10,099,057 B2 10/2018 Kent et al.
10,112,040 B2 10/2018 Herb et al.
10,118,035 B2 11/2018 Perez et al.
10,118,049 B2 11/2018 Matthews
10,124,169 B2 11/2018 Sabesan et al.
10,130,809 B2 11/2018 Cartledge et al.
10,130,810 B2 11/2018 Ferree et al.
10,134,378 B1 11/2018 Cenci et al.
10,137,025 B2 11/2018 Fior et al.
10,173,060 B2 1/2019 Wong et al.
10,179,238 B2 1/2019 Wong et al.
10,188,863 B2 1/2019 Kaemmerer et al.
10,199,125 B2 2/2019 Rao et al.
10,201,705 B2 2/2019 Bharmi et al.
10,213,593 B2 2/2019 Kaplan et al.
10,213,602 B2 2/2019 Ironi et al.
10,232,174 B2 3/2019 Simon et al.
10,232,179 B2 3/2019 Grill et al.
10,252,053 B2 4/2019 Page et al.
10,258,798 B2 4/2019 Panken et al.
10,265,523 B2 4/2019 Simon et al.
10,285,602 B2 5/2019 Tognetti et al.
10,285,646 B1 5/2019 Grant et al.
10,286,210 B2 5/2019 Yoo
10,293,159 B2 5/2019 Kong et al.
10,335,396 B2 7/2019 Nemechek
10,335,594 B2 7/2019 Lin et al.
10,335,595 B2 7/2019 Ferree et al.
10,342,977 B2 7/2019 Raghunathan
10,363,415 B2 7/2019 Simon et al.
10,383,571 B1 8/2019 Giuffrida et al.
10,398,896 B2 9/2019 Lin et al.
10,441,787 B2 10/2019 Canning et al.
10,456,573 B1 10/2019 Feinstein et al.
10,463,854 B2 11/2019 Perez
10,478,626 B1 11/2019 Giuffrida et al.
10,485,971 B2 11/2019 Schepis et al.
10,493,281 B2 12/2019 Giftakis et al.
10,499,848 B2 12/2019 Weinstock
10,500,396 B2 12/2019 Tamaki et al.
10,506,944 B2 12/2019 Tognetti et al.
10,507,327 B2 12/2019 Tracey et al.
10,518,090 B2 12/2019 Gelfand et al.
10,537,732 B2 1/2020 Nachum et al.
10,549,093 B2 2/2020 Wong et al.
10,556,107 B2 2/2020 Yoo et al.
10,561,839 B2 2/2020 Wong et al.
10,561,844 B2 2/2020 Meyyappan et al.
10,589,097 B2 3/2020 Meyyappan et al.
10,603,482 B2 3/2020 Hamner et al.
10,610,114 B2 4/2020 Buckley et al.
10,625,074 B2 4/2020 Rosenbluth et al.
10,632,312 B2 4/2020 Ziv
10,661,082 B2 5/2020 Kerselaers
10,679,599 B2 6/2020 Cenci et al.
10,694,992 B1 6/2020 Giuffrida et al.
10,695,568 B1 6/2020 Covalin
10,695,569 B2 6/2020 Levine et al.
10,698,492 B2 6/2020 Daniels
10,716,941 B2 7/2020 Yang et al.
10,722,709 B2 7/2020 Yoo et al.
10,736,577 B2 8/2020 Horne
10,750,946 B1 8/2020 Giuffrida
10,758,732 B1 9/2020 Heldman

(56) References Cited

U.S. PATENT DOCUMENTS 10,765,856 B2 9/2020 Wong et al.
10,773,079 B2 9/2020 Keller et al.
10,780,269 B2 9/2020 Gozani et al.
10,786,199 B1 9/2020 Giuffrida et al.
10,786,200 B1 9/2020 Giuffrida
10,786,625 B1 9/2020 Giuffrida et al.
10,786,669 B2 9/2020 Rajguru et al.
10,806,928 B2 10/2020 Sharma et al.
10,814,130 B2 10/2020 Wong et al.
10,814,131 B2 10/2020 Goldwasser et al.
D902,769 S 11/2020 Riot et al.
10,835,736 B2 11/2020 Horter et al.
10,850,090 B2 12/2020 Rosenbluth et al.
10,857,363 B2 12/2020 Tehrani
10,870,002 B2 12/2020 Wybo et al.
10,881,854 B2 1/2021 Son et al.
10,881,856 B2 1/2021 Giuffrida et al.
10,898,124 B1 1/2021 Fafiani et al.
10,898,709 B2 1/2021 Wagner et al.
10,905,879 B2 2/2021 Wong et al.
10,912,712 B2 2/2021 Tracey et al.
10,918,853 B2 2/2021 Creasey et al.
10,918,867 B2 2/2021 Walker
10,933,240 B2 3/2021 Kressel et al.
10,940,311 B2 3/2021 Gozani et al.
10,945,879 B2 3/2021 Black et al.
10,960,207 B2 3/2021 Wong et al.
D915,399 S 4/2021 Chao et al.
10,966,652 B1 4/2021 Giuffrida et al.
10,967,177 B2 4/2021 Lee
10,967,182 B2 4/2021 Khodaparast et al.
10,974,049 B1 4/2021 Giuffrida et al.
10,981,007 B2 4/2021 Patel et al.
10,994,132 B1 5/2021 Giuffrida et al.
11,004,563 B2 5/2021 Lin et al.
11,020,591 B2 6/2021 Errico et al.
11,026,835 B2 6/2021 Black et al.
11,027,116 B2 6/2021 Kong et al.
11,027,130 B2 6/2021 Hoffer
11,033,206 B2 6/2021 Roh
11,033,731 B2 6/2021 Jeffery et al.
11,033,736 B2 6/2021 Edgerton et al.
11,040,198 B1 6/2021 Giuffrida et al.
11,040,203 B1 6/2021 Giuffrida et al.
11,058,867 B2 7/2021 Nathan et al.
11,077,300 B2 8/2021 McBride
11,077,301 B2 8/2021 Creasey et al.
11,079,225 B2 8/2021 Ong et al.
11,103,691 B2 8/2021 Charlesworth et al.
11,103,699 B1 8/2021 Oppenheim et al.
11,123,562 B1 9/2021 Giuffrida et al.
11,141,586 B2 10/2021 Campean et al.
11,141,587 B2 10/2021 Campean et al.
11,160,971 B2 11/2021 Sharma et al.
11,160,979 B1 11/2021 Giuffrida et al.
11,166,632 B2 11/2021 Grossman et al.
11,191,959 B2 12/2021 Ben-David et al.
11,191,967 B1 12/2021 Giuffrida et al.
11,191,968 B1 12/2021 Giuffrida et al.
11,197,999 B2 12/2021 Crosson
11,207,518 B2 12/2021 Huston et al.
11,213,681 B2 1/2022 Raghunathan
11,224,742 B2 1/2022 Burnett
11,247,040 B2 2/2022 Ferree et al.
11,247,053 B2 2/2022 Rajguru et al.
11,247,056 B2 2/2022 Hareland et al.
11,260,225 B2 3/2022 Errico et al.
11,266,836 B2 3/2022 Charlesworth et al.
11,266,838 B1 3/2022 Tehrani
11,278,724 B2 3/2022 Law et al.
11,285,321 B2 3/2022 Ganguly et al.
11,311,235 B1 4/2022 Giuffrida et al.
11,318,296 B2 5/2022 Xiao et al.
11,318,307 B2 5/2022 Kern et al.
11,324,954 B2 5/2022 Bhattacharya et al.
11,331,480 B2 5/2022 Hamner et al.
11,338,120 B2 5/2022 Yun et al.
11,338,128 B2 5/2022 Lawson et al.
11,344,722 B2 5/2022 Wong et al.
11,344,732 B2 5/2022 Moffitt et al.
11,357,981 B2 6/2022 Moaddeb et al.
11,363,982 B1 6/2022 Giuffrida et al.
11,367,519 B1 6/2022 Heldman et al.
11,383,087 B1 7/2022 Heldman et al.
11,389,074 B2 7/2022 Togenetti et al.
11,389,651 B2 7/2022 Tamaki et al.
11,400,288 B2 8/2022 Simon et al.
11,419,515 B2 8/2022 Crosson et al.
11,420,052 B2 8/2022 Doskocil et al.
11,420,054 B2 8/2022 Page et al.
11,424,755 B2 8/2022 Yang et al.
D962,929 S 9/2022 He et al.
11,433,237 B2 9/2022 Lovett
11,471,685 B2 10/2022 Bolea
11,484,710 B2 11/2022 Mantovani et al.
11,497,915 B2 11/2022 Tehrani
11,504,530 B2 11/2022 Herr et al.
11,517,753 B2 12/2022 Rhodes
11,523,754 B2 12/2022 Battista
11,529,283 B2 12/2022 Francois et al.
11,534,605 B2 12/2022 Bouton et al.
11,541,239 B2 1/2023 Tracey et al.
11,547,316 B2 1/2023 Crosson et al.
11,559,250 B1 1/2023 Giuffrida et al.
11,590,348 B2 2/2023 Moaddeb et al.
11,596,327 B2 3/2023 Griffiths et al.
11,596,785 B2 3/2023 Hamner et al.
11,596,791 B2 3/2023 Wong et al.
11,596,792 B2 3/2023 Campean et al.
11,607,167 B2 3/2023 Han et al.
11,623,078 B2 4/2023 Simon et al.
11,628,300 B2 4/2023 Rajguru et al.
11,642,513 B2 5/2023 Sharma et al.
11,642,529 B2 5/2023 Suri et al.
11,666,758 B2 6/2023 Crosson
11,672,981 B2 6/2023 Jaasma et al.
11,701,293 B2 7/2023 Carballo et al.
11,717,682 B2 8/2023 Gozani et al.
11,744,482 B1 9/2023 Giuffrida et al.
11,759,642 B1 9/2023 Heldman
11,766,187 B2 9/2023 Togenetti et al.
11,766,191 B2 9/2023 Sharma et al.
11,779,764 B2 10/2023 Pepin et al.
11,786,727 B2 10/2023 Colborn et al.
11,786,730 B1 10/2023 Giuffrida et al.
11,786,735 B1 10/2023 Giuffrida et al.
11,794,012 B2 10/2023 Napadow et al.
11,794,013 B2 10/2023 Kressel et al.
11,809,629 B1 11/2023 Segil et al.
11,833,352 B2 12/2023 Law et al.
11,839,583 B1 12/2023 Carballo et al.
11,839,762 B2 12/2023 Doskocil et al.
11,844,943 B2 12/2023 Rajguru et al.
11,844,945 B1 12/2023 Giuffrida et al.
11,857,778 B2 1/2024 Hamner et al.
11,872,399 B2 1/2024 Raghunathan
11,878,166 B2 1/2024 Colburn et al.
11,890,468 B1 2/2024 Yu
11,890,469 B2 2/2024 Moaddeb et al.
11,890,475 B2 2/2024 Vaidyanathan
11,896,824 B2 2/2024 Doskocil
11,911,604 B2 2/2024 Sharma et al.
11,911,605 B2 2/2024 Crosson et al.
11,911,609 B1 2/2024 Heldman et al.
11,918,806 B2 3/2024 Wong et al.
11,918,810 B1 3/2024 Giuffrida et al.
11,918,826 B2 3/2024 Smith et al.
11,922,915 B2 3/2024 Cenci et al.
11,931,578 B2 3/2024 Shelton et al.
11,975,190 B2 5/2024 Cho et al.
11,975,195 B1 5/2024 Giuffrida et al.
11,986,317 B1 5/2024 Heldman et al.
11,992,682 B2 5/2024 Crawford
11,992,685 B2 5/2024 Kassiri Bidhendi et al.

(56) References Cited

U.S. PATENT DOCUMENTS 12,029,287 B2 7/2024 Ye et al.
12,029,899 B1 7/2024 Kostopoulos
12,053,627 B2 8/2024 Stanslaski et al.
12,070,601 B2 8/2024 Martins et al.
12,083,334 B2 9/2024 Burnett
12,109,413 B2 10/2024 Wong et al.
12,138,007 B2 11/2024 Sharareh
12,138,452 B2 11/2024 Arbel et al.
12,144,993 B2 11/2024 Bauer
12,157,001 B2 12/2024 Wong et al.
12,161,478 B1 12/2024 Heldman et al.
12,161,858 B2 12/2024 Rosenbluth et al.
12,161,865 B2 12/2024 Hamner et al.
12,172,015 B2 12/2024 Simon et al.
12,179,012 B2 12/2024 Simon et al.
12,182,328 B2 12/2024 Segil et al.
12,186,085 B2 1/2025 Buckley et al.
12,186,548 B2 1/2025 Jackson et al.
12,214,204 B1 2/2025 Giuffrida et al.
12,226,632 B2 2/2025 Rajguru et al.
12,237,121 B2 2/2025 Ye et al.
D1,065,549 S 3/2025 Ye et al.
D1,066,701 S 3/2025 Raghunathan et al.
D1,066,702 S 3/2025 Raghunathan et al.
12,251,560 B1 3/2025 Blabaky et al.
D1,069,129 S 4/2025 Raghunathan et al.
12,262,979 B2 4/2025 Togenetti et al.
12,263,009 B1 4/2025 Giuffrida et al.
12,263,342 B2 4/2025 Elyahoodayan et al.
12,280,258 B2 4/2025 Hughes et al.
12,285,610 B1 4/2025 Giuffrida et al.
12,290,687 B2 5/2025 Shelton et al.
12,311,175 B2 5/2025 Charlesworth et al.
12,318,341 B2 6/2025 Carballo et al.
12,318,342 B2 6/2025 Carballo et al.
12,329,716 B2 6/2025 Francois et al.
12,343,532 B1 7/2025 Chakravarthy
12,357,196 B2 7/2025 Sharma et al.
12,357,824 B2 7/2025 Wong et al.
12,380,980 B1 8/2025 Heldman et al.
12,409,323 B1 9/2025 Giuffrida et al.
12,414,704 B2 9/2025 Verzal et al.
12,420,082 B2 9/2025 Hamner et al.
12,449,899 B2 10/2025 VanWyk et al.
12,453,853 B2 10/2025 Rosenbluth et al.
12,453,855 B2 10/2025 Keenan
12,465,215 B2 11/2025 Fotiadis
12,465,272 B2 11/2025 Dundovic et al.
12,465,764 B1 11/2025 Covalin et al.
12,472,357 B2 11/2025 Dieken et al.
12,485,275 B2 12/2025 Atkin et al.
12,491,367 B2 12/2025 Tracey et al.
12,496,447 B2 12/2025 Lim et al.
12,502,121 B1 12/2025 Giuffrida
12,502,527 B2 12/2025 Covalin et al.
12,502,536 B2 12/2025 Moaddeb et al.
12,515,046 B2 1/2026 Leuthardt et al.
12,569,681 B2 3/2026 Meyyappan et al.
12,575,780 B2 3/2026 Hamner et al.
12,576,273 B2 3/2026 Song et al.
12,629,522 B1 5/2026 Yu
2001/0020177 A1 9/2001 Gruzdowich et al.
2001/0056290 A1 12/2001 Fischell et al.
2002/0055761 A1 5/2002 Mann et al.
2002/0070252 A1 6/2002 Bauer
2002/0120183 A1 8/2002 Abraham-Fuchs et al.
2002/0138116 A1 9/2002 Bertolucci
2002/0161415 A1* 10/2002 Cohen ................ A61N 1/36003 607/48
2002/0165586 A1 11/2002 Hill et al.
2002/0177882 A1 11/2002 DiLorenzo
2003/0032992 A1 2/2003 Thacker et al.
2003/0045922 A1 3/2003 Northrop
2003/0088294 A1 5/2003 Gesotti
2003/0093098 A1 5/2003 Heitzmann et al.
2003/0100932 A1 5/2003 Ciaff
2003/0149457 A1 8/2003 Tcheng et al.
2003/0181959 A1 9/2003 Dobak, III
2003/0187483 A1 10/2003 Grey et al.
2003/0191506 A1 10/2003 Shloznikov
2003/0195583 A1 10/2003 Gruzdowich et al.
2004/0015094 A1 1/2004 Manabe et al.
2004/0088025 A1 5/2004 Gessotti
2004/0093093 A1 5/2004 Andrews
2004/0102819 A1 5/2004 Zou et al.
2004/0111129 A1 6/2004 Gliner et al.
2004/0127939 A1 7/2004 Grey et al.
2004/0133249 A1 7/2004 Gesotti
2004/0167588 A1 8/2004 Bertolucci
2004/0249416 A1 12/2004 Yun et al.
2004/0267153 A1 12/2004 Bergethon
2004/0267331 A1 12/2004 Koeneman et al.
2005/0015042 A1 1/2005 Sun et al.
2005/0021103 A1 1/2005 DiLorenzo
2005/0055063 A1 3/2005 Loeb et al.
2005/0060009 A1 3/2005 Geotz
2005/0065553 A1 3/2005 Ben Ezra et al.
2005/0075502 A1 4/2005 Shafer
2005/0076909 A1 4/2005 Stahmann et al.
2005/0171576 A1 8/2005 Williams et al.
2005/0171577 A1 8/2005 Cohen et al.
2005/0182454 A1 8/2005 Gharib et al.
2005/0222626 A1 10/2005 DiLorenzo
2005/0234309 A1 10/2005 Klapper
2005/0240241 A1 10/2005 Yun et al.
2005/0257349 A1 11/2005 Bauer
2005/0261559 A1 11/2005 Mumford et al.
2006/0015153 A1 1/2006 Gliner et al.
2006/0047326 A1 3/2006 Wheeler
2006/0052726 A1 3/2006 Weisz et al.
2006/0074450 A1 4/2006 Boveja et al.
2006/0095088 A1 5/2006 De Ridder
2006/0161218 A1 7/2006 Danilov
2006/0173509 A1 8/2006 Lee et al.
2006/0184059 A1 8/2006 Jadidi
2006/0217781 A1 9/2006 John
2006/0224191 A1 10/2006 DiLorenzo
2006/0229678 A1 10/2006 Lee
2006/0253167 A1 11/2006 Kurtz et al.
2006/0276853 A1 12/2006 Tass
2006/0293723 A1 12/2006 Whitehurst et al.
2007/0027486 A1 2/2007 Armstrong
2007/0073361 A1 3/2007 Goren et al.
2007/0123951 A1 5/2007 Boston
2007/0123952 A1 5/2007 Strother et al.
2007/0142862 A1 6/2007 DiLorenzo
2007/0142874 A1 6/2007 John
2007/0156179 A1 7/2007 Karashurov
2007/0156182 A1 7/2007 Castel et al.
2007/0156183 A1 7/2007 Rhodes
2007/0156200 A1 7/2007 Kornet et al.
2007/0173899 A1 7/2007 Levin et al.
2007/0173903 A1 7/2007 Goren et al.
2007/0185409 A1 8/2007 Wu et al.
2007/0203533 A1 8/2007 Goren et al.
2007/0203534 A1 8/2007 Tapper
2007/0207193 A1 9/2007 Zasler et al.
2007/0249952 A1 10/2007 Rubin et al.
2007/0255319 A1 11/2007 Greenberg et al.
2007/0255323 A1 11/2007 Werder et al.
2007/0256284 A1 11/2007 Bauer
2007/0276217 A1 11/2007 Brown et al.
2007/0282228 A1 12/2007 Einav et al.
2007/0293917 A1 12/2007 Thompson et al.
2007/0294746 A1 12/2007 Sasakura et al.
2008/0004672 A1 1/2008 Dalal et al.
2008/0009772 A1 1/2008 Tyler et al.
2008/0021505 A1 1/2008 Hastings et al.
2008/0027507 A1 1/2008 Bijelic et al.
2008/0030170 A1 2/2008 Dacuay et al.
2008/0033259 A1 2/2008 Manto et al.
2008/0033504 A1 2/2008 Bertolucci
2008/0033510 A1 2/2008 Herregraven et al.
2008/0033511 A1 2/2008 Dobak

(56) References Cited

U.S. PATENT DOCUMENTS

2008/0045775 A1 2/2008 Lozano
2008/0051839 A1 2/2008 Libbus et al.
2008/0051845 A1 2/2008 Mentelos
2008/0058773 A1 3/2008 John
2008/0058871 A1 3/2008 Libbus et al.
2008/0058893 A1 3/2008 Noujokat
2008/0061961 A1 3/2008 John
2008/0091256 A1 4/2008 Libbus et al.
2008/0097564 A1 4/2008 Lathrop
2008/0147146 A1 6/2008 Wahlgren et al.
2008/0177398 A1 7/2008 Gross et al.
2008/0195007 A1 8/2008 Podrazhansky et al.
2008/0208282 A1 8/2008 Gelfand et al.
2008/0208288 A1 8/2008 Podrazhansky et al.
2008/0216593 A1 9/2008 Jacobsen et al.
2008/0243204 A1 10/2008 Uthman et al.
2008/0269593 A1 10/2008 Weinstock
2008/0288016 A1 11/2008 Amurthur et al.
2008/0300449 A1 12/2008 Gerber et al.
2008/0306325 A1 12/2008 Burnett et al.
2008/0312520 A1 12/2008 Rowlandson et al.
2009/0005713 A1 1/2009 Podrazhansky et al.
2009/0018609 A1 1/2009 DiLorenzo
2009/0049722 A1 2/2009 Chan
2009/0076565 A1 3/2009 Surwit
2009/0082831 A1 3/2009 Paul et al.
2009/0099623 A1 4/2009 Bentwich
2009/0105785 A1 4/2009 Wei et al.
2009/0112133 A1 4/2009 Deisseroth et al.
2009/0132018 A1 5/2009 DiUbaldi et al.
2009/0157138 A1 6/2009 Errico et al.
2009/0187121 A1 7/2009 Evans
2009/0216294 A1 8/2009 Ewing et al.
2009/0222053 A1 9/2009 Gaunt et al.
2009/0247910 A1 10/2009 Klapper
2009/0249617 A1 10/2009 Karicherla et al.
2009/0270952 A1 10/2009 Weinstock
2009/0299435 A1 12/2009 Gliner et al.
2009/0312690 A1 12/2009 Kim et al.
2009/0318986 A1 12/2009 Alo et al.
2009/0326595 A1 12/2009 Brockway et al.
2009/0326607 A1 12/2009 Castel et al.
2010/0004715 A1 1/2010 Fahey
2010/0010381 A1 1/2010 Skelton et al.
2010/0010383 A1 1/2010 Skelton et al.
2010/0010572 A1 1/2010 Skelton et al.
2010/0016929 A1 1/2010 Prochazka
2010/0030119 A1 2/2010 McNames et al.
2010/0036464 A1 2/2010 Picciano
2010/0057154 A1 3/2010 Dietrich et al.
2010/0059722 A1 3/2010 Copp-Howland et al.
2010/0072046 A1 3/2010 Maeda et al.
2010/0076533 A1 3/2010 Dar et al.
2010/0099963 A1 4/2010 Kilger
2010/0107657 A1 5/2010 Vistakula
2010/0125220 A1 5/2010 Seong
2010/0152623 A1 6/2010 Williams
2010/0152817 A1 6/2010 Gillbe
2010/0168501 A1 7/2010 Burnett et al.
2010/0168604 A1 7/2010 Echauz
2010/0174342 A1 7/2010 Boston et al.
2010/0202172 A1 8/2010 Skirda et al.
2010/0222629 A1 9/2010 Burnett et al.
2010/0222630 A1 9/2010 Mangrum et al.
2010/0227330 A1 9/2010 Fink et al.
2010/0228180 A1 9/2010 Jayes et al.
2010/0249637 A1 9/2010 Walter et al.
2010/0292527 A1 11/2010 Schneider et al.
2010/0298655 A1 11/2010 McCombie
2010/0298905 A1 11/2010 Simon
2010/0324611 A1 12/2010 Deming et al.
2011/0004268 A1* 1/2011 Tcheng .............. A61N 1/36135
607/45
2011/0009920 A1 1/2011 Whitehurst et al.
2011/0021899 A1 1/2011 Arps et al.
2011/0040204 A1 2/2011 Ivorra et al.
2011/0040288 A1 2/2011 Eckstein et al.
2011/0054358 A1 3/2011 Kim et al.
2011/0071590 A1 3/2011 Mounaim et al.
2011/0082524 A1 4/2011 Thomas et al.
2011/0098780 A1 4/2011 Graupe et al.
2011/0112605 A1 5/2011 Fahey
2011/0118805 A1 5/2011 Wei et al.
2011/0125212 A1 5/2011 Tyler
2011/0137375 A1 6/2011 McBride
2011/0152968 A1 6/2011 Nathan et al.
2011/0184489 A1 7/2011 Nicolelis et al.
2011/0196446 A1 8/2011 Wu
2011/0202107 A1 8/2011 Sunagawa et al.
2011/0208444 A1 8/2011 Solinky
2011/0213278 A1 9/2011 Horak et al.
2011/0224571 A1 9/2011 Pascual-Leone et al.
2011/0230701 A1 9/2011 Simon et al.
2011/0245734 A1 10/2011 Wagner et al.
2011/0250297 A1 10/2011 Oronsky et al.
2011/0282412 A1 11/2011 Glukhovsky et al.
2011/0288615 A1 11/2011 Armstrong et al.
2011/0301663 A1 12/2011 Wang et al.
2011/0313327 A1 12/2011 Van Acht et al.
2012/0010492 A1 1/2012 Thramann et al.
2012/0035674 A1 2/2012 Weinstock
2012/0035680 A1 2/2012 Napadow
2012/0046535 A1 2/2012 Lin et al.
2012/0050298 A1 3/2012 Hoffman
2012/0053491 A1 3/2012 Nathan et al.
2012/0059298 A1 3/2012 Hoffman et al.
2012/0078319 A1 3/2012 De Ridder
2012/0088986 A1 4/2012 David et al.
2012/0092178 A1 4/2012 Callsen et al.
2012/0098493 A1 4/2012 Budike
2012/0101326 A1 4/2012 Simon et al.
2012/0109013 A1 5/2012 Everett et al.
2012/0136410 A1 5/2012 Rezai et al.
2012/0158094 A1 6/2012 Kramer et al.
2012/0184801 A1 7/2012 Simon et al.
2012/0185020 A1 7/2012 Simon et al.
2012/0186121 A1 7/2012 Hanssen et al.
2012/0203079 A1 8/2012 Mclaughlin
2012/0203245 A1 8/2012 Imabayashi et al.
2012/0211013 A1 8/2012 Otis
2012/0220812 A1 8/2012 Mishelevich
2012/0239112 A1 9/2012 Muraoka
2012/0245483 A1 9/2012 Lundqvist
2012/0259255 A1 10/2012 Tomlinson et al.
2012/0277621 A1 11/2012 Gerber et al.
2012/0289869 A1 11/2012 Tyler
2012/0290036 A1 11/2012 Karamanoglu et al.
2012/0302821 A1 11/2012 Burnett
2012/0303080 A1 11/2012 Ben-David et al.
2012/0310298 A1 12/2012 Besio et al.
2012/0310299 A1 12/2012 Norbert et al.
2012/0310303 A1 12/2012 Popovic et al.
2012/0330182 A1 12/2012 Alberts et al.
2013/0006322 A1 1/2013 Tai
2013/0035745 A1 2/2013 Ahmed et al.
2013/0046276 A1 2/2013 Mernoe et al.
2013/0053817 A1 2/2013 Yun et al.
2013/0060124 A1 3/2013 Zietsma
2013/0066388 A1 3/2013 Bernhard et al.
2013/0066393 A1 3/2013 Gross et al.
2013/0066395 A1 3/2013 Simon et al.
2013/0085317 A1 4/2013 Feinstein
2013/0090519 A1 4/2013 Tass
2013/0106684 A1 5/2013 Weast et al.
2013/0116606 A1 5/2013 Cordo
2013/0123568 A1 5/2013 Hamilton et al.
2013/0123666 A1 5/2013 Giuffrida et al.
2013/0123684 A1 5/2013 Giuffrida et al.
2013/0131484 A1 5/2013 Pernu
2013/0131770 A1 5/2013 Rezai
2013/0150918 A1 6/2013 Peterson et al.
2013/0158624 A1 6/2013 Bain et al.
2013/0158627 A1 6/2013 Gozani et al.
2013/0178765 A1 7/2013 Mishelevich

(56) References Cited

U.S. PATENT DOCUMENTS

2013/0211471 A1 8/2013 Libbus et al.
2013/0231713 A1 9/2013 De Ridder et al.
2013/0236867 A1 9/2013 Avni et al.
2013/0238049 A1 9/2013 Simon et al.
2013/0245486 A1 9/2013 Simon et al.
2013/0245713 A1 9/2013 Tass
2013/0253299 A1 9/2013 Weber et al.
2013/0262298 A1 10/2013 Morley
2013/0267759 A1 10/2013 Jin
2013/0281890 A1 10/2013 Mishelevich
2013/0289647 A1 10/2013 Bhadra et al.
2013/0296967 A1 11/2013 Skaribas et al.
2013/0297022 A1 11/2013 Pathak
2013/0317565 A1 11/2013 Weinstock
2013/0331907 A1 12/2013 Sumners et al.
2013/0333094 A1 12/2013 Rogers et al.
2013/0338726 A1 12/2013 Machado
2014/0005743 A1 1/2014 Giuffrida et al.
2014/0025059 A1 1/2014 Kerr
2014/0031605 A1 1/2014 Schneider
2014/0039573 A1 2/2014 Jindra
2014/0039575 A1 2/2014 Bradley
2014/0046406 A1 2/2014 Ellrich et al.
2014/0046407 A1 2/2014 Ben-Ezra et al.
2014/0046423 A1 2/2014 Rajguru et al.
2014/0058189 A1 2/2014 Stubbeman
2014/0067003 A1 3/2014 Vase et al.
2014/0074179 A1 3/2014 Heldman et al.
2014/0074180 A1 3/2014 Giuffrida et al.
2014/0078694 A1 3/2014 Wissmar
2014/0081345 A1 3/2014 Hershey
2014/0081353 A1 3/2014 Cook et al.
2014/0094675 A1 4/2014 Luna et al.
2014/0094873 A1 4/2014 Emborg et al.
2014/0107542 A1 4/2014 Schubert et al.
2014/0114117 A1 4/2014 Naghavi et al.
2014/0128939 A1 5/2014 Embrey et al.
2014/0132410 A1 5/2014 Chang
2014/0142654 A1 5/2014 Simon et al.
2014/0148872 A1 5/2014 Goldwasser et al.
2014/0148873 A1 5/2014 Kirn
2014/0155799 A1 6/2014 Skahan et al.
2014/0163444 A1 6/2014 Ingvarsson
2014/0171834 A1 6/2014 DeGoede et al.
2014/0180361 A1 6/2014 Burdick et al.
2014/0200573 A1 7/2014 Deem et al.
2014/0214119 A1 7/2014 Greiner et al.
2014/0228927 A1 8/2014 Ahmad et al.
2014/0236258 A1 8/2014 Carroll et al.
2014/0246628 A1 9/2014 Anhalt et al.
2014/0249452 A1 9/2014 Marsh et al.
2014/0257047 A1 9/2014 Sillay et al.
2014/0257129 A1 9/2014 Choi et al.
2014/0257141 A1 9/2014 Giuffrida et al.
2014/0276194 A1 9/2014 Osorio
2014/0277220 A1 9/2014 Brennan et al.
2014/0296752 A1 10/2014 Edgerton et al.
2014/0296934 A1 10/2014 Gozani et al.
2014/0296935 A1 10/2014 Ferree et al.
2014/0300490 A1 10/2014 Kotz et al.
2014/0309709 A1 10/2014 Gozanl et al.
2014/0316484 A1 10/2014 Edgerton et al.
2014/0324118 A1 10/2014 Simon et al.
2014/0330068 A1 11/2014 Partsch et al.
2014/0330335 A1 11/2014 Errico et al.
2014/0336003 A1 11/2014 Franz et al.
2014/0336722 A1 11/2014 Rocon De Lima et al.
2014/0336731 A1 11/2014 Weinstock
2014/0343462 A1 11/2014 Burnet
2014/0350436 A1 11/2014 Nathan et al.
2014/0358040 A1 12/2014 Kim et al.
2014/0364678 A1 12/2014 Harry et al.
2015/0004656 A1 1/2015 Tang et al.
2015/0005852 A1 1/2015 Hershey et al.
2015/0012067 A1 1/2015 Bradley et al.
2015/0018926 A1 1/2015 Frenkel et al.
2015/0026783 A1 1/2015 Tseng et al.
2015/0038886 A1 2/2015 Snow
2015/0042315 A1 2/2015 Cen et al.
2015/0044656 A1 2/2015 Eichhorn et al.
2015/0057506 A1 2/2015 Luna et al.
2015/0073310 A1 3/2015 Pracar et al.
2015/0080979 A1 3/2015 Lasko et al.
2015/0097617 A1 4/2015 Chak
2015/0100004 A1 4/2015 Goldman et al.
2015/0100104 A1 4/2015 Kiani et al.
2015/0100105 A1 4/2015 Kiani et al.
2015/0112404 A1 4/2015 Holding et al.
2015/0148865 A1 5/2015 Gozani et al.
2015/0148866 A1 5/2015 Bulsen et al.
2015/0148878 A1 5/2015 Yoo et al.
2015/0157274 A1 6/2015 Ghassemzadeh et al.
2015/0163873 A1 6/2015 Kawai et al.
2015/0164377 A1 6/2015 Nathan et al.
2015/0164401 A1 6/2015 Toth et al.
2015/0190085 A1 7/2015 Nathan et al.
2015/0190634 A1 7/2015 Rezai et al.
2015/0196767 A1 7/2015 Zaghloul
2015/0202444 A1 7/2015 Franke et al.
2015/0208955 A1 7/2015 Smith
2015/0216475 A1 8/2015 Luna et al.
2015/0230733 A1 8/2015 Heo et al.
2015/0230756 A1 8/2015 Luna et al.
2015/0273234 A1 10/2015 Weinstock
2015/0277559 A1 10/2015 Vescovi et al.
2015/0290463 A1 10/2015 Yonce
2015/0297901 A1 10/2015 Kockx
2015/0321000 A1 11/2015 Rosenbluth et al.
2015/0335882 A1 11/2015 Gross
2015/0360030 A1 12/2015 Cartledge et al.
2016/0001096 A1 1/2016 Mishelevich
2016/0008620 A1 1/2016 Stubbeman
2016/0016014 A1 1/2016 Wagner et al.
2016/0022987 A1 1/2016 Zschaeck et al.
2016/0022989 A1 1/2016 Pfeifer
2016/0038059 A1 2/2016 Asada et al.
2016/0039239 A1 2/2016 Ward et al.
2016/0045140 A1 2/2016 Kitamura et al.
2016/0082253 A1 3/2016 Moffitt et al.
2016/0089045 A1 3/2016 Sadeghian-Motahar et al.
2016/0106344 A1 4/2016 Nazari
2016/0120432 A1 5/2016 Sridhar et al.
2016/0121110 A1 5/2016 Kent et al.
2016/0128621 A1 5/2016 Machado et al.
2016/0129248 A1 5/2016 Creasey et al.
2016/0144186 A1 5/2016 Kaemmerer et al.
2016/0156261 A1 6/2016 Kaneda
2016/0157735 A1 6/2016 Zhang
2016/0158542 A1 6/2016 Ahmed
2016/0158565 A1 6/2016 Lee
2016/0198998 A1 7/2016 Rahimi et al.
2016/0213924 A1 7/2016 Coleman et al.
2016/0220836 A1 8/2016 Parks
2016/0233034 A1 8/2016 Sheng
2016/0242656 A1 8/2016 Jackson et al.
2016/0256689 A1 9/2016 Vallejo et al.
2016/0262685 A1 9/2016 Wagner et al.
2016/0263376 A1 9/2016 Yoo et al.
2016/0279435 A1 9/2016 Hyde et al.
2016/0287879 A1 10/2016 Denison et al.
2016/0336722 A1 11/2016 Taxter
2016/0339239 A1 11/2016 Yoo et al.
2016/0361540 A9 12/2016 Simon et al.
2016/0375249 A1 12/2016 Bonnet et al.
2017/0014625 A1 1/2017 Rosenbluth et al.
2017/0027812 A1 2/2017 Hyde et al.
2017/0036025 A1 2/2017 Sachs et al.
2017/0042467 A1 2/2017 Herr et al.
2017/0055880 A1 3/2017 Agrawal et al.
2017/0056238 A1 3/2017 Yi et al.
2017/0056643 A1 3/2017 Herb et al.
2017/0079597 A1 3/2017 Horne
2017/0080207 A1 3/2017 Perez et al.
2017/0087364 A1 3/2017 Cartledge et al.

(56) References Cited

U.S. PATENT DOCUMENTS

2017/0095667 A1 4/2017 Yakovlev et al.
2017/0113045 A1 4/2017 Baldassano et al.
2017/0132067 A1 5/2017 Singaravelu et al.
2017/0157398 A1 6/2017 Wong et al.
2017/0165485 A1 6/2017 Sullivan et al.
2017/0224991 A1 8/2017 Wingeier et al.
2017/0239415 A1 8/2017 Hwang et al.
2017/0246481 A1 8/2017 Mishelevich
2017/0259061 A1 9/2017 Simon et al.
2017/0266443 A1 9/2017 Rajguru et al.
2017/0274208 A1 9/2017 Nagel et al.
2017/0287146 A1 10/2017 Pathak et al.
2017/0312505 A1 11/2017 Ahmed
2017/0312512 A1 11/2017 Creasey et al.
2017/0312513 A1 11/2017 Hershey et al.
2017/0361093 A1 12/2017 Yoo et al.
2017/0368329 A1 12/2017 Tyler et al.
2018/0001086 A1 1/2018 Bartholomew et al.
2018/0001088 A1 1/2018 Tass
2018/0021576 A1 1/2018 Wong et al.
2018/0028809 A1 2/2018 Ziv
2018/0028841 A1 2/2018 Konofagou et al.
2018/0036535 A1 2/2018 Wong et al.
2018/0042654 A1 2/2018 Ingvarsson et al.
2018/0049676 A1 2/2018 Griffiths et al.
2018/0064344 A1 3/2018 Nguyen
2018/0064362 A1 3/2018 Hennings et al.
2018/0064944 A1 3/2018 Grill et al.
2018/0116546 A1 5/2018 Pastoor et al.
2018/0132757 A1 5/2018 Kong et al.
2018/0140842 A1 5/2018 Olaighin et al.
2018/0168905 A1 6/2018 Goodall et al.
2018/0169400 A1 6/2018 Wong et al.
2018/0199841 A1 7/2018 Yang et al.
2018/0214694 A1 8/2018 Parramon
2018/0221620 A1 8/2018 Metzger
2018/0235500 A1 8/2018 Lee et al.
2018/0236217 A1 8/2018 Hamner et al.
2018/0264263 A1 9/2018 Rosenbluth et al.
2018/0289965 A1 10/2018 Nelson et al.
2018/0345020 A1 12/2018 Ironi et al.
2018/0361153 A1 12/2018 Giuffrida et al.
2019/0001117 A1 1/2019 Ben-David et al.
2019/0001129 A1 1/2019 Rosenbluth et al.
2019/0001139 A1 1/2019 Mishra et al.
2019/0126047 A1 5/2019 Kassiri Bidhendi et al.
2019/0134393 A1 5/2019 Wong et al.
2019/0143098 A1 5/2019 Kaplan et al.
2019/0143111 A1 5/2019 Hamner et al.
2019/0143113 A1 5/2019 Wong et al.
2019/0167976 A1 6/2019 Byers et al.
2019/0229727 A1 7/2019 Krishna
2019/0269914 A1 9/2019 Moaddeb et al.
2019/0298998 A1 10/2019 Coleman et al.
2019/0299008 A1 10/2019 Rao
2019/0321636 A1 10/2019 Law et al.
2019/0343462 A1 11/2019 Grant et al.
2019/0374771 A1 12/2019 Simon et al.
2020/0023183 A1 1/2020 Ollerenshaw et al.
2020/0038654 A1 2/2020 Doskocil et al.
2020/0046968 A1 2/2020 Herr et al.
2020/0061378 A1 2/2020 Ganguly et al.
2020/0069947 A1 3/2020 Kent
2020/0077943 A1 3/2020 Weinstock
2020/0093400 A1 3/2020 Hamner et al.
2020/0139118 A1 5/2020 John et al.
2020/0147373 A1 5/2020 Tamaki et al.
2020/0155847 A1 5/2020 Perez
2020/0171269 A1 6/2020 Hooper et al.
2020/0171304 A1 6/2020 Simon et al.
2020/0179687 A1 6/2020 Wong et al.
2020/0197707 A1 6/2020 Covalin
2020/0204164 A1 6/2020 Nishiyama
2020/0215324 A1 7/2020 Mantovani et al.
2020/0221975 A1 7/2020 Basta et al.
2020/0246617 A1 8/2020 Errico et al.
2020/0254247 A1 8/2020 Brezel et al.
2020/0254251 A1 8/2020 Wong et al.
2020/0269046 A1 8/2020 Page et al.
2020/0276442 A1 9/2020 Owen
2020/0282201 A1 9/2020 Doskocil
2020/0289813 A1 9/2020 Ito et al.
2020/0289814 A1 9/2020 Hamner et al.
2020/0297999 A1 9/2020 Pal
2020/0316379 A1 10/2020 Yoo et al.
2020/0324104 A1 10/2020 Labuschagne et al.
2020/0338348 A1 10/2020 Honeycutt et al.
2020/0346008 A1 11/2020 Song
2020/0367775 A1 11/2020 Buckley et al.
2020/0405188 A1 12/2020 Sharma et al.
2020/0406022 A1 12/2020 Sharma et al.
2021/0008369 A1 1/2021 Crosson
2021/0016079 A1 1/2021 Ekelem et al.
2021/0016089 A1 1/2021 Crosson
2021/0023376 A1 1/2021 Hareland et al.
2021/0031026 A1 2/2021 Simon et al.
2021/0031036 A1 2/2021 Sharma et al.
2021/0052883 A1 2/2021 Wong et al.
2021/0052897 A1 2/2021 Bhadra et al.
2021/0052900 A1 2/2021 Pepin et al.
2021/0060337 A1 3/2021 Wybo et al.
2021/0069507 A1 3/2021 Gozani et al.
2021/0085974 A1 3/2021 Bouton et al.
2021/0085976 A1 3/2021 Heldman et al.
2021/0099867 A1 4/2021 Brown et al.
2021/0100999 A1 4/2021 Rosenbluth et al.
2021/0101007 A1 4/2021 Hamner et al.
2021/0113834 A1 4/2021 Wong et al.
2021/0128906 A1 5/2021 Perez et al.
2021/0162212 A1 6/2021 Kern et al.
2021/0169684 A1 6/2021 Black et al.
2021/0187279 A1 6/2021 Bouton et al.
2021/0205619 A1 7/2021 Wong et al.
2021/0212230 A1 7/2021 Hsu et al.
2021/0213283 A1 7/2021 Yoo et al.
2021/0220650 A1 7/2021 Kassiri Bidhendi et al.
2021/0244940 A1 8/2021 Liberatore et al.
2021/0244950 A1 8/2021 Ironi et al.
2021/0248893 A1 8/2021 Van Dinther
2021/0252278 A1 8/2021 Hamner et al.
2021/0252279 A1 8/2021 Kong et al.
2021/0260379 A1 8/2021 Charlesworth et al.
2021/0266011 A1 8/2021 Chen et al.
2021/0283400 A1 9/2021 Hamner et al.
2021/0289814 A1 9/2021 Roubos-Van Den Hil et al.
2021/0299445 A1 9/2021 Rajguru et al.
2021/0308460 A1 10/2021 Wong et al.
2021/0330547 A1 10/2021 Moaddeb et al.
2021/0330974 A1 10/2021 Wong et al.
2021/0353181 A1 11/2021 Roh
2021/0379374 A1 12/2021 Hamner et al.
2021/0379379 A1 12/2021 Campean et al.
2021/0402172 A1 12/2021 Ross et al.
2022/0001164 A1 1/2022 Sharma et al.
2022/0016413 A1 1/2022 John et al.
2022/0031245 A1 2/2022 Bresler
2022/0054820 A1 2/2022 Turner
2022/0054831 A1 2/2022 McBride
2022/0080196 A1 3/2022 Crosson
2022/0088373 A1 3/2022 Burnett
2022/0126095 A1 4/2022 Rajguru et al.
2022/0134104 A1 5/2022 Elyahoodayan et al.
2022/0143391 A1 5/2022 Vaishya et al.
2022/0143392 A1 5/2022 Labuschagne et al.
2022/0143393 A1 5/2022 Charlesworth et al.
2022/0143402 A1 5/2022 Oppenheim et al.
2022/0203091 A1 6/2022 Vysokov
2022/0212007 A1 7/2022 Rajguru et al.
2022/0218991 A1 7/2022 Moaddeb et al.
2022/0220276 A1 7/2022 Ziebell et al.
2022/0233860 A1 7/2022 Hamner et al.
2022/0266011 A1 8/2022 Hamner et al.
2022/0266012 A1 8/2022 Hamner et al.
2022/0273938 A1 9/2022 Chen

(56) References Cited

U.S. PATENT DOCUMENTS

2022/0287616 A1 9/2022 Dundovic et al.
2022/0323745 A1 10/2022 Staats et al.
2022/0347461 A1 11/2022 Campean et al.
2022/0370786 A1 11/2022 Atkin et al.
2022/0370802 A1 11/2022 Tracey et al.
2022/0387793 A1 12/2022 Song et al.
2022/0401721 A1 12/2022 Jackson et al.
2022/0409404 A1 12/2022 Yang et al.
2023/0001205 A1 1/2023 Aprasoff
2023/0009158 A1 1/2023 Liberatore
2023/0010696 A1 1/2023 Pradeep
2023/0026037 A1 1/2023 Larraya et al.
2023/0062326 A1 3/2023 Colachis et al.
2023/0074017 A1 3/2023 Pan
2023/0075750 A1 3/2023 Pan
2023/0080790 A1 3/2023 Crosson et al.
2023/0086004 A1 3/2023 Yang et al.
2023/0110185 A1 4/2023 Mantovani et al.
2023/0146449 A1 5/2023 Muse et al.
2023/0148956 A1 5/2023 Narayanan et al.
2023/0172542 A1 6/2023 Baker et al.
2023/0191115 A1 6/2023 Blum et al.
2023/0191126 A1 6/2023 Kent et al.
2023/0200732 A1 6/2023 Ye et al.
2023/0201584 A1 6/2023 Rajguru et al.
2023/0207232 A1 6/2023 Ye et al.
2023/0218897 A1 7/2023 Wang et al.
2023/0230669 A1 7/2023 Jung
2023/0233855 A1 7/2023 Sunkeri et al.
2023/0241393 A1 8/2023 Suri et al.
2023/0248962 A1 8/2023 Zhang et al.
2023/0256245 A1 8/2023 Crosson
2023/0277091 A1 9/2023 Blanco
2023/0277109 A1 9/2023 Blum et al.
2023/0277838 A1 9/2023 Errico et al.
2023/0277841 A1 9/2023 Wang et al.
2023/0285743 A1 9/2023 Muccio
2023/0293882 A1 9/2023 Howe
2023/0321430 A1 10/2023 Ye et al.
2023/0321436 A1 10/2023 Tass
2023/0321437 A1 10/2023 Nemechek
2023/0337944 A1 10/2023 Szmulewicz et al.
2023/0338225 A1 10/2023 Carballo et al.
2023/0363711 A1 11/2023 Theodore et al.
2023/0371846 A1 11/2023 Sharma et al.
2023/0381505 A1 11/2023 Gozani et al.
2023/0381545 A1 11/2023 Carballo et al.
2023/0397833 A1 12/2023 Tognetti et al.
2024/0001120 A1 1/2024 Napadow et al.
2024/0032819 A1 2/2024 Zhao et al.
2024/0042203 A1 2/2024 Gill et al.
2024/0050308 A1 2/2024 Carballo et al.
2024/0058606 A1 2/2024 Law et al.
2024/0062890 A1 2/2024 Shin et al.
2024/0065617 A1 2/2024 Choi
2024/0066286 A1 2/2024 Yin et al.
2024/0066287 A1 2/2024 Siff
2024/0090600 A1 3/2024 Colachis et al.
2024/0091533 A1 3/2024 Ziv et al.
2024/0108239 A1 4/2024 Crosson et al.
2024/0122797 A1 4/2024 Moaddeb et al.
2024/0123223 A1 4/2024 Charlesworth et al.
2024/0123226 A1 4/2024 Raymondos
2024/0123227 A1 4/2024 Charlesworth et al.
2024/0123230 A1 4/2024 Raghunathan
2024/0149063 A1 5/2024 Leuthardt et al.
2024/0156674 A1 5/2024 Carballo et al.
2024/0156675 A1 5/2024 Carballo et al.
2024/0157142 A1 5/2024 Yeniel et al.
2024/0189538 A1 6/2024 Bamber
2024/0189594 A1 6/2024 Hamner et al.
2024/0189596 A1 6/2024 Mech et al.
2024/0197200 A1 6/2024 Thorp et al.
2024/0197204 A1 6/2024 Jung et al.
2024/0197237 A1 6/2024 Hamner et al.
2024/0207618 A1 6/2024 Baker et al.
2024/0226550 A1 7/2024 Moaddeb et al.
2024/0245388 A1 7/2024 Plunger
2024/0245905 A1 7/2024 Fitzgerald
2024/0252824 A1 8/2024 Verzal et al.
2024/0285941 A1 8/2024 Raymondos
2024/0285951 A1 8/2024 Huynh et al.
2024/0293669 A1 9/2024 Kostopoulos
2024/0293670 A1 9/2024 Kostopoulos
2024/0293674 A1 9/2024 Shelton et al.
2024/0299734 A1 9/2024 Wang et al.
2024/0299735 A1 9/2024 Wang et al.
2024/0316339 A1 9/2024 Keefer et al.
2024/0325727 A1 10/2024 Hamner et al.
2024/0325728 A1 10/2024 Schulte et al.
2024/0335654 A1 10/2024 Schulte et al.
2024/0350805 A1 10/2024 Kent
2024/0366935 A1 11/2024 Olofsson et al.
2024/0374208 A1 11/2024 Zaphrir et al.
2024/0386553 A1 11/2024 Akakin et al.
2024/0399148 A1 12/2024 Leuthardt et al.
2024/0406000 A1 12/2024 Nguyen et al.
2024/0408382 A1 12/2024 Shin et al.
2024/0416110 A1 12/2024 Kim
2024/0428429 A1 12/2024 Akakin et al.
2025/0001193 A1 1/2025 MÜLler-Bruhn
2025/0010061 A1 1/2025 John et al.
2025/0010068 A1 1/2025 Carballo et al.
2025/0010078 A1 1/2025 Netoff et al.
2025/0017518 A1 1/2025 Shah et al.
2025/0017815 A1 1/2025 Carballo et al.
2025/0018185 A1 1/2025 Ye et al.
2025/0032789 A1 1/2025 David
2025/0037595 A1 1/2025 Carballo et al.
2025/0037880 A1 1/2025 Pepin
2025/0041597 A1 2/2025 Tyler et al.
2025/0058101 A1 2/2025 Kong
2025/0058106 A1 2/2025 Simon et al.
2025/0065114 A1 2/2025 Crosson et al.
2025/0065117 A1 2/2025 Charlesworth et al.
2025/0068737 A1 2/2025 Keith et al.
2025/0082924 A1 3/2025 Simon et al.
2025/0099019 A1 3/2025 Muhammed et al.
2025/0114608 A1 4/2025 Haddock et al.
2025/0128058 A1 4/2025 Hamner et al.
2025/0128059 A1 4/2025 Rigot et al.
2025/0135189 A1 5/2025 Wong et al.
2025/0135199 A1 5/2025 Evans et al.
2025/0135200 A1 5/2025 Wong et al.
2025/0144405 A1 5/2025 Jackson et al.
2025/0144415 A1 5/2025 Vaishya et al.
2025/0161663 A1 5/2025 Rosenbluth et al.
2025/0161664 A1 5/2025 Wong et al.
2025/0161665 A1 5/2025 Liberatore et al.
2025/0161678 A1 5/2025 Rodriguez et al.
2025/0161684 A1 5/2025 Hamner et al.
2025/0161685 A1 5/2025 Hamner et al.
2025/0170399 A1 5/2025 Wong et al.
2025/0195877 A1 6/2025 Schulte et al.
2025/0205464 A1 6/2025 Bradley et al.
2025/0222256 A1 7/2025 Cardasis et al.
2025/0222261 A1 7/2025 Elyahoodayan et al.
2025/0235690 A1 7/2025 Jeffrey et al.
2025/0242150 A1 7/2025 Bouton et al.
2025/0248641 A1 8/2025 Mase
2025/0249244 A1 8/2025 Keenan
2025/0262430 A1 8/2025 Ross et al.
2025/0268783 A1 8/2025 Carballo et al.
2025/0269184 A1 8/2025 Shelton et al.
2025/0281309 A1 9/2025 Benigni et al.
2025/0281347 A1 9/2025 Francois et al.
2025/0281349 A1 9/2025 Carballo et al.
2025/0281735 A1 9/2025 Yang
2025/0295319 A1 9/2025 Tognetti et al.
2025/0319311 A1 10/2025 Sharma et al.
2025/0325815 A1 10/2025 Mazanec et al.
2025/0332415 A1 10/2025 Kent et al.
2025/0339671 A1 11/2025 Rosenbluth et al.
2025/0339672 A1 11/2025 Wong et al.

(56) References Cited

U.S. PATENT DOCUMENTS

2025/0339685 A1 11/2025 Wong et al.
2025/0345593 A1 11/2025 Rosenbluth et al.
2025/0345594 A1 11/2025 Rosenbluth et al.
2025/0352855 A1 11/2025 Dirkes et al.
2025/0367457 A1 12/2025 Moore et al.
2025/0375134 A1 12/2025 Chen
2025/0375612 A1 12/2025 Wong et al.
2025/0380891 A1 12/2025 Buckley et al.
2025/0381397 A1 12/2025 Gill et al.
2025/0381398 A1 12/2025 McNutt
2026/0000891 A1 1/2026 Yang
2026/0007354 A1 1/2026 Yang
2026/0007357 A1 1/2026 Sobel et al.
2026/0021301 A1 1/2026 Rosenbluth et al.
2026/0027364 A1 1/2026 Tucker
2026/0041910 A1 2/2026 Ollis
2026/0048263 A1 2/2026 Covalin et al.
2026/0076608 A1 3/2026 Dundovic et al.
2026/0077180 A1 3/2026 Rosenbluth et al.
2026/0077181 A1 3/2026 Rosenbluth et al.
2026/0115461 A1 4/2026 Balbaky et al.
2026/0115466 A1 4/2026 Wong et al.

FOREIGN PATENT DOCUMENTS

CN 1826154 8/2006
CN 101022849 8/2007
CN 101115524 1/2008
CN 101365373 2/2009
CN 101612043 12/2009
CN 101687093 3/2010
CN 101801453 8/2010
CN 102089031 6/2011
CN 102481394 5/2012
CN 102905757 1/2013
CN 202724457 2/2013
CN 103517732 1/2014
CN 103608069 2/2014
CN 103889503 6/2014
CN 104144729 11/2014
CN 104168951 11/2014
CN 104436431 3/2015
CN 104519960 4/2015
CN 104939815 9/2015
CN 105457158 4/2016
CN 105848710 8/2016
CN 106413805 2/2017
CN 106687161 5/2017
CN 106794347 5/2017
CN 206434707 U 8/2017
CN 107949421 4/2018
CN 108697890 10/2018
CN 111358461 7/2020
CN 118022172 2/2024
CN 117679641 3/2024
CN 118320302 7/2024
CN 222488608 U 2/2025
CN 120114759 6/2025
DE 10 2008042373 4/2010
DE 10 2009004011 7/2010
EP 0000759 2/1979
EP 0801957 10/1997
EP 0725665 1/1998
EP 1062988 12/2000
EP 1558333 5/2007
EP 1727591 4/2009
EP 2383014 11/2011
EP 2291115 9/2013
EP 2801389 11/2014
EP 2892418 7/2015
EP 2892419 7/2015
EP 2892613 7/2015
EP 3020448 5/2016
EP 2948043 12/2016
EP 2029222 3/2017
EP 2780073 9/2017
EP 1951365 10/2017
EP 3154627 4/2018
EP 2827771 5/2018
EP 3184143 7/2018
EP 3075412 12/2018
EP 2691149 2/2019
EP 3349712 7/2019
EP 2790777 9/2019
EP 2734110 3/2020
EP 3503960 3/2020
EP 2667934 5/2020
EP 3650077 5/2020
EP 3113684 7/2020
EP 3352846 7/2020
EP 3337557 8/2020
EP 3493874 8/2020
EP 3409200 9/2020
EP 3701865 9/2020
EP 3427793 11/2020
EP 3212277 12/2020
EP 3436140 1/2021
EP 3758595 1/2021
EP 3261710 3/2021
EP 3641876 4/2021
EP 3679979 6/2021
EP 3841967 6/2021
EP 3402404 7/2021
EP 3562541 7/2021
EP 3453423 8/2021
EP 3675795 8/2021
EP 3648832 11/2021
EP 3100765 1/2022
EP 3693053 1/2022
EP 2741813 3/2022
EP 3399912 4/2022
EP 3558446 8/2022
EP 2714188 12/2022
EP 3487578 12/2022
EP 4108292 12/2022
EP 4119038 1/2023
EP 2967415 5/2023
EP 3326688 6/2023
EP 3378462 6/2023
EP 3784337 6/2023
EP 3870270 8/2023
EP 4233990 8/2023
EP 3541279 9/2023
EP 3989907 10/2023
EP 3990105 10/2023
EP 4171469 10/2023
EP 3600011 11/2023
EP 3996807 11/2023
EP 4010063 11/2023
EP 3461530 1/2024
EP 3463550 3/2024
EP 3565631 4/2024
EP 4115942 4/2024
EP 4356952 4/2024
EP 3842094 5/2024
EP 4061472 7/2024
EP 3990098 8/2024
EP 3784336 11/2024
EP 3893988 3/2025
EP 4556056 5/2025
EP 4433151 6/2025
EP 4578487 7/2025
EP 4241675 11/2025
EP 4659795 12/2025
ES 2222819 3/2006
ES 2272137 6/2008
GB 2496449 5/2013
JP 2010-527256 1/1900
JP 2002-200178 7/2002
JP 2003-501207 1/2003
JP 2003-533299 11/2003
JP 2004-512104 4/2004
JP 2006-503658 2/2006
JP 2008-018235 1/2008

(56) References Cited

FOREIGN PATENT DOCUMENTS

| | | |
|---|---|---|
| JP | 2009-034328 | 2/2009 |
| JP | 2009-512516 | 3/2009 |
| JP | 2009-529352 | 8/2009 |
| JP | 2010-506618 | 3/2010 |
| JP | 2010-512926 | 4/2010 |
| JP | 2010-246745 | 11/2010 |
| JP | 2012-005596 | 1/2012 |
| JP | 2012-055650 | 3/2012 |
| JP | 2012-217565 | 11/2012 |
| JP | 2013-017609 | 1/2013 |
| JP | 2013-094305 | 5/2013 |
| JP | 5439921 | 3/2014 |
| JP | 2015-514460 | 5/2015 |
| JP | 2016-511651 | 4/2016 |
| JP | 2018-038597 | 3/2018 |
| JP | 2018-516702 | 6/2018 |
| JP | 2019-531775 | 11/2019 |
| KR | 20130104446 | 9/2013 |
| WO | WO 1987/01024 | 2/1987 |
| WO | WO 1994/000187 | 1/1994 |
| WO | WO 1994/017855 | 8/1994 |
| WO | WO 95/19804 | 7/1995 |
| WO | WO 1996/032909 | 10/1996 |
| WO | WO 98/23326 | 6/1998 |
| WO | WO 98/40121 | 9/1998 |
| WO | WO 1998/043700 | 10/1998 |
| WO | WO 1999/019019 | 4/1999 |
| WO | WO 2000/015293 | 3/2000 |
| WO | WO 2000/076436 | 12/2000 |
| WO | WO 01/03768 | 1/2001 |
| WO | WO 2001/087411 | 11/2001 |
| WO | WO 2002/017987 | 3/2002 |
| WO | WO 2002/034327 | 5/2002 |
| WO | WO 03/015866 | 2/2003 |
| WO | WO 2004/037344 | 5/2004 |
| WO | WO 2004/067087 | 8/2004 |
| WO | WO 2004/108209 | 12/2004 |
| WO | WO 2005/007029 | 5/2005 |
| WO | WO 2005/105201 | 11/2005 |
| WO | WO 2005/0122894 | 12/2005 |
| WO | WO 2006/021820 | 3/2006 |
| WO | WO 2006/044793 | 4/2006 |
| WO | WO 2006/054118 | 5/2006 |
| WO | WO 2006/092007 | 9/2006 |
| WO | WO 2006/102724 | 10/2006 |
| WO | WO 2007/056493 | 5/2007 |
| WO | WO 2007/092290 | 8/2007 |
| WO | WO 2007/112092 | 10/2007 |
| WO | WO 2008/005478 | 1/2008 |
| WO | WO 2008/045598 | 4/2008 |
| WO | WO 2008/062395 | 5/2008 |
| WO | WO 2008/106174 | 9/2008 |
| WO | WO 2008/150591 | 12/2008 |
| WO | WO 2009/005797 | 1/2009 |
| WO | WO 2009/153730 | 12/2009 |
| WO | WO 2010/014260 | 2/2010 |
| WO | WO 2010/031055 | 3/2010 |
| WO | WO 2010/111321 | 9/2010 |
| WO | WO 2010/141155 | 12/2010 |
| WO | WO 2011/106225 | 9/2011 |
| WO | WO 2011/119224 | 9/2011 |
| WO | WO 2011/144883 | 11/2011 |
| WO | WO 2011/149656 | 12/2011 |
| WO | WO 2012/040243 | 3/2012 |
| WO | WO 2012/074794 | 6/2012 |
| WO | WO 2012166860 | 12/2012 |
| WO | WO 2013012625 | 1/2013 |
| WO | WO 2013/071307 | 5/2013 |
| WO | WO 2013/074809 | 5/2013 |
| WO | WO 2013/173727 | 11/2013 |
| WO | WO 2014/043757 | 3/2014 |
| WO | WO 2014040007 | 3/2014 |
| WO | WO 2014040018 | 3/2014 |
| WO | WO 2014040023 | 3/2014 |
| WO | WO 2014/053041 | 4/2014 |
| WO | WO 2014055507 | 4/2014 |
| WO | WO 2014/070999 | 5/2014 |
| WO | WO 2014/089549 | 6/2014 |
| WO | WO 2014/093964 | 6/2014 |
| WO | WO 2014/113813 | 7/2014 |
| WO | WO 2014/146082 | 9/2014 |
| WO | WO 2014/151431 | 9/2014 |
| WO | WO 2014/153201 | 9/2014 |
| WO | WO 2014138022 | 9/2014 |
| WO | WO 2014/207512 | 12/2014 |
| WO | WO 2015/033152 | 3/2015 |
| WO | WO 2015/039206 | 3/2015 |
| WO | WO 2015/039244 | 3/2015 |
| WO | WO 2015/042365 | 3/2015 |
| WO | WO 2015/079319 | 6/2015 |
| WO | WO 2015/085880 | 6/2015 |
| WO | WO 2015/095880 | 6/2015 |
| WO | WO 2015/128090 | 9/2015 |
| WO | WO 2015/138981 | 9/2015 |
| WO | WO 2015/148184 | 10/2015 |
| WO | WO 2015/164706 | 10/2015 |
| WO | WO 2015/187712 | 12/2015 |
| WO | WO 2016/007093 | 1/2016 |
| WO | WO 2016/019250 | 2/2016 |
| WO | WO 2016/032929 | 3/2016 |
| WO | WO 2016/094728 | 6/2016 |
| WO | WO 2016/102958 | 6/2016 |
| WO | WO 2016/110804 | 7/2016 |
| WO | WO 2016/128985 | 8/2016 |
| WO | WO 2016/149751 | 9/2016 |
| WO | WO 2016/166281 | 10/2016 |
| WO | WO 2016/176668 | 11/2016 |
| WO | WO 2016/179407 | 11/2016 |
| WO | WO 2016/189422 | 12/2016 |
| WO | WO 2016/195587 | 12/2016 |
| WO | WO 2016/201366 | 12/2016 |
| WO | WO 2017/004021 | 1/2017 |
| WO | WO 2017/010930 | 1/2017 |
| WO | WO 2017/023864 | 2/2017 |
| WO | WO 2017/044904 | 3/2017 |
| WO | WO 2017/053847 | 3/2017 |
| WO | WO 2017/062994 | 4/2017 |
| WO | WO 2017/086798 | 5/2017 |
| WO | WO 2017/088573 | 6/2017 |
| WO | WO 2017/105930 | 6/2017 |
| WO | WO 2017/132067 | 8/2017 |
| WO | WO 2017/199026 | 11/2017 |
| WO | WO 2017/208167 | 12/2017 |
| WO | WO 2017/209673 | 12/2017 |
| WO | WO 2017/210729 | 12/2017 |
| WO | WO 2017/221037 | 12/2017 |
| WO | WO 2018/009680 | 1/2018 |
| WO | WO 2018/028170 | 2/2018 |
| WO | WO 2018/028220 | 2/2018 |
| WO | WO 2018/028221 | 2/2018 |
| WO | WO 2018/039458 | 3/2018 |
| WO | WO 2018/093765 | 5/2018 |
| WO | WO 2018/106839 | 6/2018 |
| WO | WO 2018/112164 | 6/2018 |
| WO | WO 2018119220 | 6/2018 |
| WO | WO 2018/187241 | 10/2018 |
| WO | WO 2019/005774 | 1/2019 |
| WO | WO 2019/014250 | 1/2019 |
| WO | WO 2019/028000 | 2/2019 |
| WO | WO 2019/046180 | 3/2019 |
| WO | WO 2019/082180 | 6/2019 |
| WO | WO 2019/143790 | 7/2019 |
| WO | WO 2019/169240 | 9/2019 |
| WO | WO 2019/202489 | 10/2019 |
| WO | WO 2019/213433 | 11/2019 |
| WO | WO 2020/006048 | 1/2020 |
| WO | WO 2020/068830 | 4/2020 |
| WO | WO 2020/069219 | 4/2020 |
| WO | WO 2020/086726 | 4/2020 |
| WO | WO 2020/131857 | 6/2020 |
| WO | WO 2020/185601 | 9/2020 |
| WO | WO 2020/252406 | 12/2020 |
| WO | WO 2021/005584 | 1/2021 |
| WO | WO 2021/055716 | 3/2021 |

(56) References Cited

FOREIGN PATENT DOCUMENTS

WO WO 2021/062345 4/2021
WO WO 2021/092533 5/2021
WO WO 2021/127422 6/2021
WO WO 2021/228128 11/2021
WO WO 2021/236815 11/2021
WO WO 2021/252292 12/2021
WO WO 2022/090834 5/2022
WO WO 2022/187318 9/2022
WO WO 2022/187486 9/2022
WO WO 2022/221858 10/2022
WO WO 2022/235607 11/2022
WO WO 2023/283568 1/2023
WO WO 2023/014499 2/2023
WO WO 2023/015158 2/2023
WO WO 2023/015159 3/2023
WO WO 2023/129722 7/2023
WO WO 2023/156391 8/2023
WO WO 2023/163300 8/2023
WO WO 2023/168016 9/2023
WO WO 2023/191236 10/2023
WO WO 2023/192519 10/2023
WO WO 2023/196578 10/2023
WO WO 2023/215558 11/2023
WO WO 2023/222911 11/2023
WO WO 2023/224636 11/2023
WO WO 2024/059136 3/2024
WO WO 2024/059140 3/2024
WO WO 2024/059141 3/2024
WO WO 2024/059643 3/2024
WO WO 2024/059651 3/2024
WO WO 2024/059663 3/2024
WO WO 2024/083685 4/2024
WO WO 2024/086209 4/2024
WO WO 2024/119042 6/2024
WO WO 2024/155527 7/2024
WO WO 2024/182256 9/2024
WO WO 2024/206883 10/2024
WO WO 2024/215916 10/2024
WO WO 2024/218174 10/2024
WO WO 2024/228655 11/2024
WO WO 2024/233290 11/2024
WO WO 2024/234051 11/2024
WO WO 2024/238988 11/2024
WO WO 2024/241067 11/2024
WO WO2024/243537 11/2024
WO WO 2024/258592 12/2024
WO WO 2025/000028 1/2025
WO WO 2025/010365 1/2025
WO WO 2025/015047 1/2025
WO WO 2025/024798 1/2025
WO WO 2025/029578 2/2025
WO WO 2025/029692 2/2025
WO WO 2025/029698 2/2025
WO WO 2025/038457 2/2025
WO WO 2025/038622 2/2025
WO WO 2025/046593 3/2025
WO WO 2025/049694 3/2025
WO WO 2025/069021 4/2025
WO WO 2025/080428 4/2025
WO WO 2025/081022 4/2025
WO WO 2025/219728 4/2025
WO WO 2025068762 4/2025
WO WO 2025/087735 5/2025
WO WO 2025/099587 5/2025
WO WO 2025/104232 5/2025
WO WO 2025/106892 5/2025
WO WO 2025/117608 6/2025
WO WO 2025/117609 6/2025
WO WO 2025/127179 6/2025
WO WO 2025/128510 6/2025
WO WO 2025/128825 6/2025
WO WO 2025/133597 6/2025
WO WO 2025/136631 6/2025
WO WO 2025/151398 7/2025
WO WO 2025/151439 7/2025
WO WO 2025/155529 7/2025
WO WO 2025/175157 8/2025
WO WO 2025/177139 8/2025
WO WO 2025/193607 9/2025
WO WO 2025/219826 10/2025
WO WO 2025/220500 10/2025
WO WO 2025/226257 10/2025
WO WO 2025/231998 11/2025
WO WO 2025/240843 11/2025
WO WO 2025/243290 11/2025
WO WO 2025/245482 11/2025
WO WO 2025/247161 12/2025
WO WO 2025/250395 12/2025
WO WO 2025/264783 12/2025
WO WO 2026/003575 1/2026
WO WO 2026/003759 1/2026
WO WO 2026/005669 1/2026
WO WO 2026/010730 1/2026
WO WO 2026/011148 1/2026
WO WO 2026/020207 1/2026
WO WO 2026/060203 3/2026

OTHER PUBLICATIONS

U.S. Appl. No. 15/354,943, filed Nov. 17, 2016, Wong et al.
U.S. Appl. No. 15/580,631, filed Dec. 7, 2017, Wong et al.
U.S. Appl. No. 15/721,475, filed Sep. 29, 2017, Wong et al.
U.S. Appl. No. 15/721,480, filed Sep. 29, 2017, Wong et al.
U.S. Appl. No. 15/748,616, filed Jan. 29, 2018, Hamner et al.
U.S. Appl. No. 15/762,043, filed Mar. 21, 2018, Hamner et al.
U.S. Appl. No. 16/071,056, filed Jul. 18, 2018, Wong et al.
U.S. Appl. No. 16/241,846, filed Jan. 7, 2019, Wong et al.
U.S. Appl. No. 16/242,983, filed Jan. 8, 2019, Wong et al.
U.S. Appl. No. 16/247,310, filed Feb. 22, 2019, Wong et al.
U.S. Appl. No. 16/327,780, filed Feb. 22, 2019, Hamner et al.
U.S. Appl. No. 16/780,758, filed Feb. 3, 2020, Hamner et al.
U.S. Appl. No. 16/792,100, filed Feb. 14, 2020, Hamner et al.
U.S. Appl. No. 16/833,388, filed Mar. 27, 2020, Hamner et al.
U.S. Appl. No. 16/962,810, filed Jul. 16, 2002, Hamner et al.
U.S. Appl. No. 16/993,085, filed Aug. 13, 2020, Balbaky et al.
U.S. Appl. No. 17/013,396 filed 09-04-1001, Wong et al.
U.S. Appl. No. 17/052,483, filed Nov. 2, 2020, Liberatore et al.
U.S. Appl. No. 17/061,231, filed Oct. 1, 2020, Yu.
U.S. Appl. No. 17/080,544, filed Oct. 26, 2020, Wong et al.
U.S. Appl. No. 17/663,004, filed May 11, 2020, Wong et al.
U.S. Appl. No. 17/663,010, filed May 11, 2022, Wong et al.
Amarenco et al. "Urondynamic Effect of Acute Transcutaneous Posterior Tibial Nerve Stimulation in Overactive Bladder" Journal of Urology vol. 169, 2210-2215 (Jun. 2003).
Apartis; Clinical neurophysiology in movement disorders. Handb Clin Neurol; 111; Pediatric Neurology Pt. 1; pp. 87-92;Apr. 2013.
Barath et al., 2020, Brain metabolic changes with longitudinal transcutaneous afferent patterned stimulation in essential tremor subjects, Tremor and Other Hyperkinetic Movements, 10(1):52, pp. 1-10.
Barbaud et al.; Improvement in essential tremor after pure sensory stroke due to thalamic infarction; European neurology; 46; pp. 57-59; Jul. 2001.
Barrios et al.: BCI algorithms for tremor identification, characterization and tracking; Seventh Framework Programme, EU; Contract No. FP7-ICT-2007-224051 (v3.0); 57 pgs .; Jul. 10, 2011.
Bartley et al.; Neuromodulation for overactive bladder; Nature Reviews Urology; 10; pp. 513-521; Sep. 2013.
Benabid et al.; A putative generalized model of the effects and mechanism of action of high frequencyelectrical stimulation of the central nervous system; Acta Neural Belg; 105(3); pp. 149-157; Sep. 2005.
Bergquist et al.: Motor unit recruitment when neuromuscular electrical stimulation is applied over anerve trunk compared with a muscle belly: quadriceps femoris, Journal of Applied Physiology; vol. 113, No. 1, pp. 78-89; Jul. 2012.
Bergquist et al.; Motor unit recruitment when neuromuscular electrical stimulation is applied over anerve trunk compared with a muscle belly: triceps surae, Journal of Applied Physiology; vol. 110, No. 3, pp. 627-637; Mar. 2011.

(56) References Cited

OTHER PUBLICATIONS

Bijelic et al.: E Actitrode®: The New Selective Stimulation Interface for Functional Movements in Hemiplegic Patients; Serbian Journal of Electrical Engineering; 1(3); pp. 21-28; Nov. 2004.
Birdno et al.; Pulse-to-pulse changes in the frequency of deep brain stimulation affect tremor and modeled neuronal activity .; Journal of Neurophysiology; 98; pp. 1675-1684; Jul. 2007.
Birdno et al.; Response of human thalamic neurons to high-frequency stimulation.; PloS One; 9(5); 10 pgs.; May 2014.
Birgersson et al.; Non-invasive bioimpedance of intact skin: mathematical modeling and experiments; Physiological Measurement; 32(1); pp. 1-18; Jan. 2011.
Bohling et al.; Comparison of the stratum corneum thickness measured in vivo with confocal Ramanspectroscopy and confocal reflectance microscopy; Skin research and Technology; 20(1); pp. 50-47; Feb. 2014.
Bonaz, B., V. Sinniger, and S. Pellissier. "Vagus nerve stimulation: a new promising therapeutic tool in inflammatory bowel disease." Journal of internal medicine 282.1 (2017): 46-63.
Bowman et al.; Effects of waveform parameters on comfort during transcutaneous neuromuscular electrical stimulation; Annals of Biomedical Engineering; 13(1); pp. 59-74; Jan. 1985.
Bratton et al.; Neural regulation of inflammation: no neural connection from the vagus to splenic sympathetic neurons; Exp Physiol 97.11 (2012); pp. 1180-1185.
Brillman et al., 2022, Real-world evidence of transcutaneous afferent patterned stimulation for essential tremor, Tremor and Other Hyperkinetic Movements, 12(1):27, pp. 1-11.
Brittain et al.; Tremor suppression by rhythmic transcranial current stimulation; Current Biology; 23; pp. 436-440; Mar. 2013.
Britton et al.; Modulation of postural tremors at the wrist by supramaximal electrical median nerveshocks in Et, Pd, and normal subjects mimicking tremor; J Neurology, Neurosurgery, and Psychiatry; 56(10); pp. 1085-1089; Oct. 1993.
Buschbacher et al.; Manual of nerve conduction series; 2nd edition; Demos Medical Publishing, LLC; 2006.
Buschbacher et al.; Manual of nerve conduction series; 2nd edition; Demos Medical Publishing, LLC; 2006 (part 2, pg. #143 to #299).
Cagnan et al.; Phase dependent modulation of tremor amplitude in essential tremor through thalamic stimulation; Brain; 136(10); pp. 3062-3075; Oct. 2013.
Cala Trio Health Care Professional Guide (Jul. 2020).
Cala Trio Health Care Professional Guide (Nov. 2019).
Campero et al.; Peripheral projections of sensory fascicles in the human superficial radial nerve; Brain; 128(Pt 4); pp. 892-895; Apr. 2005.
Chang, M.D., Qwang-Yuen et al., Effect of Electroacupuncture and Transcutaneous Electrical NerveStimulation at Hegu (LI.4) Acupuncture Point on the Cutaneous Reflect, 27 Acupuncture & Electro-Therapeutics Res., Int. J. 191-202 (2002).
Chen et al.; A web-based system for home monitoring of patients with Parkinson's disease using wearable sensors; IEEE Trans on Bio-Medical Engineering; 58(3); pp. 831-836; Mar. 2011.
Choi, Jong Bo, et al. "Analysis of heart rate variability in female patients with overactive bladder." Urology 65.6 (2005): 1109-1112.
Clair et al.; Postactivation depression and recovery of reflex transmission during repetitive electrical stimulation of the human tibial nerve, Journal of Neurophysiology; vol. 106, No. 1; pp. 184-192; Jul. 2011.
Clar et al.; Skin impedance and moisturization; J. Soc. Cosmet. Chem .; 26; pp. 337-353; 1975;presented at IFSCC Vilith Int'l Congress on Cosmetics Quality and Safety in London on Aug. 26-30, 1974.
Constandinou et al.; A Partial-Current-Steering Biphasic Stimulation Driver for Vestibular Prostheses; IEEE Trans on Biomedical Circuits and Systems; 2(2); pp. 106-113; Jun. 2008.
Daneault et al.; Using a smart phone as a standalone platform for detection and monitoring of pathological tremors; Frontiers in Human Neuroscience; vol. 6, article 357; 12 pgs .; Jan. 2012.
DEUSCHL et at; Consensus statement of the Movement Disorder Society on Tremor. Ad Hoc Scientific Committee., Movement Disorders, vol. 13 Suppl 3, pp. 2-23; 1998.
Di Giovangiulio et al.; The Neuromodulation of the intestinal immune system and its relevance in inflammatory bowel disease; Frontier's in Immunology; vol. 6; Article 590; Nov. 2015.
Dideriksen et al.; EMG-based characterization of pathological tremor using the iterated Hilbert transform; IEEE transactions on Biomedical Engineering; 58(10); pp. 2911-2921; Oct. 2011.
Dosen et al.: Tremor suppression using electromyography and surface sensory electrical stimulation;Converging Clinical and Engineering Research on Neurorehabilitation; vol. 1 (Biosystems & Biorobotics Series); pp. 539-543; Feb. 2013.
Doucet et al.; Neuromuscular electrical stimulation for skeletal muscle function; The Yale Journal of Biology and Medicine; 85(2); pp. 201-215; Jun. 2012.
Extended European Search Report received in European Application No. 14740684.7 dated Jul. 25, 2016 in 7 pages.
Ferreira et al., 2019, MDS evidence-based review of treatments for essential tremor, Movement Disorders, 34(7):950-958.
Fiorentino et al., 2011, Self calibrating wearable active running asymmetry measurement and correction, Journal of Control Engineering and Applied Informatics, 13(2):3-8.
Fred E. Govier, et al., "Percutaneous Afferent Neuromodulation for the Refractory Overactive Bladder: Results of a Multicenter Study," 165 J. Urology 1193-1198 (Apr. 2001).
Fuentes et al.; Restoration of locomotive function in Parkinson's disease by spinal cord stimulation:mechanistic approach, Eur J Neurosci, vol. 32, pp. 1100-1108; Oct. 2010 (author manuscript; 19 p. ).
Fuentes et al.; Spinal cord stimulation restores locomotion in animal models of Parkinson's disease; Science; 323; pp. 1578-1582; Mar. 2009.
Gallego et al.; A neuroprosthesis for tremor management through the control of muscle co-contraction; Journal of Neuroengineering and Rehabilitation; vol. 10; 36; (13 pgs); Apr. 2013.
Gallego et al.; Real-time estimation of pathological tremor parameters from gyroscope data .; Sensors; 10(3); pp. 2129-2149; Mar. 2010.
Gallego et al.; A soft wearable robot for tremor assessment and suppression; 2011 IEEE InternationalConference on Robotics and Automation; Shanghai International Conference Center; pp. 2249-2254; May 9-13, 2011.
GAO; Analysis of amplitude and frequency variations of essential and Parkinsonian tremors; Medical & Biological Engineering & Computing; 42(3); pp. 345-349; May 2004.
Garcia et al.; Modulation of brainstem activity and connectivity by respiratory-gated auricular vagalafferent nerve stimulation in migraine patients; PAIN; International Association for the Study of Pain; 2017.
Garcia-Rill, E., et al. "Arousal, motor control, and Parkinson's disease." Translational neuroscience 6.1 pp. 198-207 (2015).
Giuffridda et al.; Clinically deployable Kinesia technology for automated tremor assessment .; Movement Disorders; 24(5); pp. 723-730; Apr. 2009.
Gracanin et al.; Optimal stimulus parameters for minimum pain in the chronic stimulation of innervated muscle; Archives of Physical Medicine and Rehabilitation; 56(6); pp. 243-249; Jun. 1975.
Gupta et al., 2021, Exploring essential tremor: results from a large online survey, Clinical Parkinsonism & Related Disorders, 5:100101, 4 pp.
H.C. Klingler, et al., "Use of Peripheral Neuromodulation of the S3 Region for Treatment of Detrusor Overactivity: A Urodynamicbased Study," UROLOGY 56:766-771, 2000.
Haeri et al.; Modeling the Parkinson's tremor and its treatments; Journal of Theoretical Biology; 236(3); pp. 311-322; Oct. 2005.
Halonen et al.; Contribution of cutaneous and muscle afferent fibres to cortical SEPs followingmedian and radial nerve stimulation in man; Electroenceph. Clin. Neurophysiol.; 71(5); pp. 331-335; Sep.-Oct. 1988.
Hao et al.; Effects of electrical stimulation of cutaneous afferents on corticospinal transmission oftremor signals in patients with Parkin-

(56) References Cited

OTHER PUBLICATIONS son's disease; 6th International Conference on Neural Engineering; San Diego, CA; pp. 355-358; Nov. 2013.
Haubenberger et al., 2018, Essential Tremor, The New England Journal of Medicine, 378:1802-1810 and Supplementary Appendix.
Hauptmann et al.; External trial deep brain stimulation device for the application of desynchronizing stimulation techniques; Journal of Neural Engineering; 6; 12 pgs.; Oct. 2009.
Heller et al.; Automated setup of functional electrical stimulation for drop foot using a novel 64channel prototype stimulator and electrode array: Results from a gait-lab based study; Medical Engineering & Physic; 35(1); pp. 74-81; Jan. 2013.
Hellwig et al., Feb. 17, 2001, Tremor-correlated cortical activity in essential tremor, The Lancet, 357:519-523.
Henry Dreyfuss Associates; The Measure of Man and Woman: Human Factors in Design (Revised Edition); John Wiley & Sons, New York; pp. 10-11 and 22-25; Dec. 2001.
Hernan, Miguel, et al. "Alcohol Consumption and the Incidence of Parkinson's Disease." May 15, 2003. Annals of Neurology. vol. 54. pp.170-175.
Hernandez-Martin et al., 2021, High-fidelity transmission of high-frequency burst stimuli from peripheral nerve to thalamic nuclei in children with dystonia, Scientific Reports, 11:8498, 9 pp.
Hua et al.; Posture-related oscillations in human cerebellar thalamus in essential tremor are enabled by voluntary motor circuits; J Neurophysiol; 93(1); pp. 117-127; Jan. 2005.
Huang, et al.; Theta burst stimulation report of the human motor cortex; Neuron, vol. 45, 201-206, Jan. 20, 2005.
Hubeaux, Katelyne, et al. "Autonomic nervous system activity during bladder filling assessed by heartrate variability analysis in women with idiopathic overactive bladder syndrome or stress urinary incontinence." The Journal of urology 178.6 (2007): 2483-2487.
Hubeaux, Katelyne, et al. "Evidence for autonomic nervous system dysfunction in females with idiopathic overactive bladder syndrome." Neurology and urodynamics 30.8 (2011): 1467-1472.
Inoue et al. "Stretchable human interface using a conductive silicone elastomer containing silver fillers." Consumer Electronics, 2009. ISCE'09. IEEE 13th International Symposium on. IEEE, 2009.
International Search Report received in Application No. 19874940.0 dated Jan. 20, 2020.
Isaacson et al., 2020, Prospective home-use study on non-invasive neuromodulation therapy for essential tremor, Tremor and Other Hyperkinetic Movements, 10(1):29, pp. 1-16.
Jacks et al.; Instability in human forearm movements studied with feed-back-controlled electrical stimulation of muscles; Journal of Physiology; 402; pp. 443-461; Aug. 1988.
Javidan, et al., Attenuation of Pathological Tremors by Functional Electrical Stimulation II: Clinical Evaluation, 20 Annals of Biomedical Engineering 225 (1992).
Jobges et al.; Vibratory proprioceptive stimulation affects Parkinsonian tremor; Parkinsonism & Related Disorders; 8(3); pp. 171-176; Jan. 2002.
Joundi et al.; Rapid tremor frequency assessment with the iPhone accelerometer .; Parkinsonism & Related Disorders; 17(4); pp. 288-290; May 2011.
Kim et al.: Adaptive control of movement for neuromuscular stimulation-assisted therapy in a rodent model; IEEE Trans on Biomedical Engineering,; 56(2); pp. 452-461; Feb. 2009.
Knutson et al., Neuromuscular Electrical Stimulation for Motor Restoration in Hemiplegia. Phys MedRehabil Clin N A,. Nov. 2015; 26(4): 729-745. Published online Aug. 1, 20154. Doi: 10.1016/j.pmr.2015.06.002.
Krauss et al.; Chronic spinal cord stimulation in medically intractable orthostatic tremor; J Neurol Neurosurg Psychiatry; 77(9); pp. 1013-1016; Sep. 2006.
Krishnamoorthy et al., 2008, Gait Training After Stroke: A Pilot Study Combining a Gravity-BalancedOrthosis, Functional Electrical Stimulation, and Visual Feedback, Journal of Neurologic Physical Therapy, 32(4): 192-202.
Kuhn et al.; Array electrode design for transcutaneous electrical stimulation a simulation study; Medical Engineering & Physics; 31 (8); pp. 945-951; Oct. 2009.
Kuhn et al.; The Influence of Electrode Size on Selectivity and Comfort in Transcutaneous ElectricalStimulation of the Forearm; Neural Systems and Rehabilitation Engineering, IEEE Transactions on; 18(3); pp. 255-262; Jun. 2010.
Kunz, Patrik, et al. "5 kHz transcranial alternating current stimulation: lack of cortical excitability changes when grouped in a theta burst pattern." Frontiers in Human Neuroscience 10 (2016): 683.
Lagerquist et al.: Influence of stimulus pulse width on M-waves, H-reflexes, and torque during tetanic low-intensity neuromuscular stimulation, Muscle & Nerve, 42(6), pp. 886-893; Dec. 2010.
Laroy et al.; The sensory innervation pattern of the fingers; J. Neurol .; 245 (5); pp. 294-298; May 1998.
Lee et al.; Resetting of tremor by mechanical perturbations: A comparison of essential tremor and parkinsonian tremor; Annals of Neurology; 10(6); pp. 523-531; Dec. 1981.
Legon et al.; Pulsed ultrasound differentially stimulates somatosensory circuits in humans as indicated by EEG and fMRI; Plos One; 7(12); e51177; 14 pgs .; Dec. 2012.
Liao, Wen-Chien, et al. "A noninvasive evaluation of autonomic nervous system dysfunction in women with an overactive bladder." International Journal of Gynecology & Obstetrics 110.1 (2010): 12-17.
Lin et al., 2018, Noninvasive neuromodulation inessential tremor demonstrates relief in a sham- controlled pilot trial, Movement Disorders, 33(7):1182-1183.
Llinas et al., Dec. 21, 1999, Thalamocortical dysrhythmia: a neurological and neuropsychiatric syndrome characterized by magnetoencephalography, PNAS, 96(26):15222-15227.
Lourenco et al.; Effects produced in human arm and forearm motoneurons after electrical stimulation of ulnar and median nerves at wrist level; Experimental Brain Research; 178(2); pp. 267-284; Apr. 2007.
Lyons et al., 2021, Essential tremor in adult patients, International Essential Tremor Foundation, 16 pp.
Malek et al.; The utility of electromyography and mechanomyography for assessing neuromuscular function: a noninvasive approach; Phys Med Rehabil in N Am; 23(1); pp. 23-32; Feb. 2012.
Mamorita et al.; Development of a system for measurement and analysis of tremor using a three-axis accelerometer; Methods Inf Med; 48(6); pp. 589-594; epub Nov. 2009.
Maneski et al.; Electrical Stimulation for suppression of pathological tremor; Med Biol Eng Comput; 49(10); pp. 1187-1193; Oct. 2011.
Marsden et al.; Coherence between cerebellar thalamus, cortex and muscle in man; Brain; 123; pp. 1459-1470; Jul. 2000.
Marshall, Ryan, et al. "Bioelectrical stimulation for the reduction of inflammation in inflammatory bowel disease." Clinical Medicine Insights: Gastroenterology 8 (2015): CGast-S31779.
Mcauley et al.; Physiological and pathological tremors and rhythmic central motor control; Brain; 123(Pt 8); pp. 1545-1567; Aug. 2000.
Mcintyre et al.; Finite element analysis of current-density and electric field generated by metal microelectrodes; Annals of Biomedical Engineering; 29(3); pp. 227-235; Mar. 2001.
Meekins et al.; American Association of Neuromuscular & Electrodiagnostic Medicine evidenced-based review: use of surface electromyography in the diagnosis and study of neuromuscular disorders; Muscle Nerve 38(4); pp. 1219-1224; Oct. 2008.
Mehnert, Ulrich, et al. "Heart rate variability: an objective measure of autonomic activity and bladder sensations during urodynamics." Neurology and urodynamics 28.4 (2009): 313-319.
Michael R. Van Balken, et al., "Posterior Tibial Nerve Stimulation as Neuromodulative Treatment of Lower Urinary Track Dysfunction," 166 J. Urology 914-918 (Sep. 2001).
Miguel et al.; Alcohol consumption and the incidence of Parkinson's disease; Ann. Neurol .; 54(2); pp. 170-175; May 15, 2003.

(56) References Cited

OTHER PUBLICATIONS

Miller et al.; Multiplexed microneedle-based biosensor array for characterization of metabolic acidosis; Talanta; 88; pp. 739-742; Jan. 2012 (author manuscript; 13 p. ).
Miller et al.; Neurostimulation in the treatment of primary headaches; Pract Neurol; Apr. 11, 2016;16:pp. 362-375.
Milne et al.; Habituation to repeated in painful and non-painful cutaneous stimuli: A quantitative psychophysical study; Experimental Brain Research; 87(2); pp. 438-444; Nov. 1991.
Mommaerts et al.; Excitation and nerve conduction; in Comprehensive Human Physiology; Springer Berlin Heidelberg; Chap. 13; pp. 283-294; Mar. 1996.
Mones et al.; The response of the tremor of patients with Parkinsonism to peripheral nerve stimulation; J Neurology, Neurosurgery, and Psychiatry; 32(6); pp. 512-518; Dec. 1969.
Morgante et al.: How many parkinsonian patients are suitable candidates for deep brain stimulationof subthalamic nucleus ?; Results of a Questionnaire, Parkinsonism Relat Disord; 13; pp. 528-531; Dec. 2007.
Munhoz et al.; Acute effect of transcutaneous electrical nerve stimulation on tremor; Movement Disorders; 18(2); pp. 191-194; Feb. 2003.
Nardone et al.; Influences of transcutaneous electrical stimulation of cutaneous and mixed nerves onsubcortical somatosensory evoked potentials; Electroenceph. Clin. Neurophysiol .; 74(1); pp. 24-35; Jan .- Feb. 1989.
Nonis et al.; Evidence of activation of vagal afferents by non-invasive vagus nerve stimulation: Anelectrophysiological study in healthy volunteers; Cephalalgia; pp. 1285-1293; vol. 37(13); Mar. 28, 2017.
Office Action recieved in U.S. Appl. No. 17/107,435 dated Aug. 30, 2022.
Office Action recieved in Japanese Application No. 2015-553901 dated Nov. 14, 2017.
Pahwa et al., 2018, An acute randomized controlled trial of noninvasive peripheral nerve stimulation in essential tremor, Neuromodulation, 22:537-545.
PCT Search Report and Written Opinion in PCT Application No. PCT/US14/12388 dated Apr. 10, 2014 in 16 pages.
PCT Search Report and Written Opinion in PCT Application No. PCT/US2015/033809 mailed Apr. 10, 2014 in 15 pages.
PCT Search Report and Written Opinion in PCT Application No. PCT/US2016/037080 mailed Sep. 13, 2016.
PCT Search Report and Written Opinion in PCT Application No. PCT/US2016/045038 mailed Nov. 15, 2016 in 16 pages.
Peng et al., 2015, Flexible dry electrode based on carbon nanotube/polymer hybrid micropillars for biopotential recording, Sensor and Actuatora A: Physical, 235:48-65.
Perez et al.; Patterned Sensory Stimulation Induces Plasticity in Reciprocal la Inhibition in Humans; The Journal of Neuroscience; 23(6); pp. 2014-2018; Mar. 2003.
Perez-Reyes, Jan. 2003, Molecular physiology of low-voltage-activated T-type calcium channels, Physiol. Rev. 83:117-161.
Perlmutter et al.; Deep brain stimulation; Ann Rev Neurosci; 29; pp. 229-257; Jul. 2006.
Popovi Maneski et al.; Electrical stimulation for the suppression of pathological tremor; Medical & Biological Engineering & Computing; 49(10); pp. 1187-1193; Oct. 2011.
Popovic-Bijelic et al. "Multi-field surface electrode for selective electrical stimulation." Artificial organs 29.6 (2005): 448-452.
Prochazka et al.; Attenuation of pathological tremors by functional electrical stimulation I: Method; Annals of Biomedical Engineering; 20(2); pp. 205-224; Mar. 1992.
PTAB-IPR2024-00732—Exhibit 1002—Declaration of John Laughlin, M. Eng., P.E., in 109 pages.
PTAB-IPR2024-00732—Petition for Inter Partes Review of U.S. Pat. No. 10,786,669, filed Mar. 29, 2024, in 101 pages.
PTAB-IPR2024-00743—Exhibit 1002—Declaration of John Laughlin, M. Eng., P.E., in 102 pages.
PTAB-IPR2024-00743—Petition for Inter Partes Review of U.S. Pat. No. 11,628,300, filed Mar. 29, 2024, in 113 pages.
Pulliam et al.; Continuous in-home monitoring of essential tremor; Parkinsonism Relat Disord; 20(1); pp. 37-40; Jan. 2014.
Quattrini et al.; Understanding the impact of painful diabetic neuropathy; Diabetes/Metabolism Research and Reviews; 19, Suppl. 1; pp. S2-S8; Jan.-Feb. 2003.
Rocon et al.; Design and validation of a rehabilitation robotic exoskeleton for tremor assessment and suppression; IEEE Trans Neural Sys and Rehab Eng .; 15(3); pp. 367-378; Sep. 2007.
Sigrist et al., 2012. Augmented visual, auditory, haptic, and multimodal feedback in motor learning: A review. Psychonomic Bulletin & Review, 20(1):21-53.
Silverstone et al.; Non-Invasive Neurostimulation In The Control of Familial Essential Tremor UsingThe Synaptic Neuromodulator; Conference Proceedings, International Functional Electrical Stimulation Society (IFES); Ed. Paul Meadows; 3 pgs .; May 1999.
Singer et al.; The effect of EMG triggered electrical stimulation plus task practice on arm function inchronic stroke patients with moderate-severe arm deficits; Restor Neurol Neurosci; 31(6); pp. 681-691; Oct. 2013.
Solomonow et al., 1998, Studies toward spasticity suppression with high frequency electrical stimulation, Orthopedics, 7(8):1284-1288.
Straube et al.; Treatment of chronic migraine with transcutaneous stimulation of the auricular branchof the vagal nerve (auricular t-VNS): a randomized, monocentric clinical trial; The Journal of Headache and Pain (2015) 16:63.
Takanashi et al.; A functional MRI study of somatotopic representation of somatosensory stimulation in the cerebellum; Neuroradiology; 45(3); pp. 149-152; Mar. 2003.
Tass et al.; Coordinated reset has sustained aftereffects in Parkinsonian monkeys; Ann Neurol; 72(5); pp. 816-820; Nov. 2012.
Tass et al.; Counteracting tinnitus by acoustic coordinated reset neuromodulation; Restorative neurology and Neuroscience; 30(2); pp. 137-159; Apr. 2012.
Tass; A Model of desynchronizing deep brain stimulation with a demand-controlled coordinated reset of neural subpopulations; Biol Cybern; 89(2); pp. 81-88; Aug. 2003.
Thomas et al.; A review of posterior tibial nerve stimulation for faecal incontinence; ColorectalDisease; 2012 The Association of Coloproctology of Great Britain and Ireland. 15, pp. 519-526; Jun. 25, 2012.
Tolosa et al.; Essential tremor: treatment with propranolol; Neurology; 25(11); p. 1041; Nov. 1975.
Tracey; The inflammatory reflex; Nature; vol. 420; pp. 853-859; Dec. 19/26, 2002.
Treager; Interpretation of skin impedance measurements; Nature; 205; pp. 600-601; Feb. 1965.
Valente; Novel methods and circuits for field shaping in deep brain stimulation; Doctoral thesis, UCL (University College London); 222 pgs .; 2011.
Vitton et al.; Transcutaneous posterior tibial nerve stimulation for fecal Incontinence in inflammatorybowel disease patients: a therapeutic option ?; Inflamm Bowel Dis; vol. 15, No. 3, Mar. 2009; pp. 402-405.
Von Lewinski et al.; Efficacy of EMG-triggered electrical arm stimulation in chronic hemiparetic stroke patients; Restor Neurol Neurosci; 27(3); pp. 189-197; Jun. 2009.
Wallerberger, Apr. 4, 2019, Efficient Estimation of Autocorrelation Spectra, ArXiv.org, https://arxiv.org/abs/1810.05079.
Wardman et al.; Subcortical, and cerebellar activation evoked by selective stimulation of muscle and cutaneous afferents: an fMRI study; Physiol. Rep .; 2(4); pp. 1-16; Apr. 2014.
Wiestler et al.; Integration of sensory and motor representations of single fingers in the human; J. Neurophysiol .; 105(6); pp. 3042-3053; Jun. 2011.
Woldag et al.; Evidence-based physiotherapeutic concepts for improving arm and hand function in stroke patients R A review; J Neurol; 249(5); pp. 518-528; May 2002.
Woolf et al.; Peripheral nerve injury triggers central sprouting of myelinated afferents; Nature; 355(6355); pp. 75-78; Jan. 1992.

(56) References Cited

OTHER PUBLICATIONS

Yarnitsky et al.; Nonpainful remote electrical stimulation alleviates episodic migraine pain; Neurology 88; pp. 1250-1255; Mar. 28, 2017.
Yeh et al., “Intensity sensitive modulation effect of theta burst form of median nerve stimulation on the monosynaptic spinal reflex.” Neural plasticity 2015 (2015) in 8 pages.
Yilmaz, Ozlem O., et al. “Efficacy of EMG-biofeedback in knee osteoarthritis.” Rheumatology international 30.7 (2010): 887-892.
Zhang et al.; Neural oscillator based control for pathological tremor suppression via functional electrical stimulation; Control Engineering Practice; 19(1); pp. 74-88; Jan. 2011.
Zorba et al.; Overactive bladder and the pons; Rize University, Medical Faculty, Department of Urology; 123-124; Oct. 18, 2012.
Zwarts et al.; Multichannel surface EMG: basic aspects and clinical utility; Muscle Nerve; 28(1); pp. 1-17; Jul. 2003.
Aemed, Inc., 510(k) Summary, StimPad™ TENS System, Dec. 6, 2007.
Antal et al., Anodal Transcranial Direct Current Stimulation of the Motor Cortex Ameliorates Chronic Pain and Reduces Short Intracortical Inhibition, Journal of Pain and Symptom Management, vol. 39, No. 5, pp. 890-903, May 2010.
De Santana, et al., Effectiveness of Transcutaneous Electrical Nerve Stimulation for Treatment of Hyperalgesia and Pain, Curr Rheumatol Rep .; 10(6): 492-499, Decmeber 2008.
Dewey, et al., A Pilot Study of Ai-Controled Transcutaneous Peripheral Nerve Stimulation for Essential Tremor, Tremor and Other Hyperkinetic Movements, 2025; 15(1): 10, pp. 1-9.
Encore Medical, L.P., Intelect Transport 2 Channel Electrotherapy User Manual, 2005.
Falco et al., Cross Talk: A New Method for Peripheral Nerve Stimulation. An Observational Report with Cadaveric Verification, Pain Physician, 12:965-983, 2009.
Fowler et al., The conduction velocities of peripheral nerve fibres conveying sensations of warming and cooling, Journal of Neurology, Neurosurgery and Psychiatry Sep. 1988;51(9):1164-70.
Griffin et al., Efficacy of High Voltage Pulsed Current for Healing of Pressure Ulcers in Patents with Spinal Cord Injury, Physical Therapy, vol. 71, No. 6, Jun. 1991, pp. 433-442.
Johnson, Factors Influencing The Analgesic Effects and Clinical Efficacy of Transcutaneous Electrical Nerve Stimulation (TENS), Newcastle University, Jul. 1991.
Jones et al., Trancutaneous electronical nerve stimulation, Continuing Education in Anaethesia, Critical Care & Pain, vol. 9, No. 4, pp. 130-135, 2009.
Korkmaz et al., Pulsed radiofrequency versus conventional transcutaneous electrical nerve stimulation in painful shoulder: a prospective, randomized study, Clin Rehabil. Nov. 2010;24(11):1000-8, Aug. 4, 2010.
Lowry et al., Spinal Cord Stimulation for the Treatment of Chronic Knee Pain Following Total Knee Replacement, Pain Physician, 13:251-256, 2010.
Miller et al., Superimposed single impulse and pulse train electrical stimulation: A quantitative assessment during submaximal isometric knee extension in young, healthy men, Superimposed Electrical Stimulation Techniques, Muscle & Nerve, Aug. 1999, pp. 1038-1046.
Cala kIQ, calahealth.com, [online], [site visited Mar. 7, 2025], Available from internet URL: https://calahealth.com/ (Year: 2025).
Feinstein Institutes for Medical Research, Northwell Health; High-frequency electrical stimulation helps reduce inflammation pain in new Feinstein Institute study; Press Release Oct. 5, 2022.
Hu et al., Pain modulation effect of breathing-controlled electrical stimulation (BreEStim) is not likely to be mediated by deep and fast voluntary breathing. Sci Rep 5, 14228 (2015). (Year: 2015).
Lauk et al., “A software for recording and analysis of human tremor,” Computer Methods and Programs in Biomedicine 60 (1999) 65-77, https://www.sciencedirect.com/science/article/pii/S0169260799000127?via%3Dihub.
Nouman et al; Additive blooming in polymer materials: Consequences in the pharmaceutical and medical field, Polymer Degradation and Stability, vol. 143, Sep. 2017, pp. 239-252 (Year: 2017).
Pain & Spine Specialists (Apr. 12, 2024). Identifying Symptoms of Diabetic Neuropathy. https://painandspinespecialists.com/ identifying-symptoms-of-diabetic-neuropathy/ (Year: 2024).
Rajaraman et al., “A novel quantitative method for 3D measurement of Parkinsonian tremor,” Clin Neurophysiol, Feb. 2000;111(2):338-43, https://pubmed.ncbi.nlm.nih.gov/10680570/.
Technical Presentation: Third-Stream Additives that Modify LSR and HCR, Nov. 13, 2020 [online]; RDAbbott webpage; hyperlink titled “presentation”; [https://rdabbott.com/wp-content/uploads/2020/11/ISC2020-.
Trends in the Health Wearable Technology, first available Oct. 26, 2021, mokosmart.com, [online], [site visited Mar. 7, 2025], Available from internet URL: https://www.mokosmart.com/health-wearable-technology-trends/ (Year: 2021).
Wang et al.; Mechanically Flexible Conductors for Stretchable and Wearable E-Skin and E-Textile Devices, May 2019; [https:// doi.org/10.1002/adma.201901408] (Year: 2019).
Yang et al.; High-frequency electrical stimulation attenuates neuronal release of inflammatory mediators and ameliorates neuropathic pain, Bioelectronic Medicine, 8(1); pp. 1-13; Oct. 5, 2022.

* cited by examiner

Before treatment
After treatment

Wrist Flexion-Extension
2°
-2°
0
2
4
6
8
10
Time (s)

Wrist Flexion-Extension
2°
-2°
0
2
4
6
8
10
Time (s)

Wrist Flexion-Extension
2°
-2°
0
2
4
6
8
10
Time (s)

700
720 Housing
797
790 Display
Processor
740 Controls
750 Power supply
770 Memory
760 Interface
780 Sensor
730 Effector 700
Interface Unit
704
Effector 730
Instructions & Power
Decision Unit
702
Display 790
Processor 797
User controls 740
Power 750
Memory 770
Sensor 780

700
Interface Unit
704
Sensor 780
Effector 730
Power 750
Data
Instructions
Decision Unit
702
Display 790
Processor 797
User controls 740
Memory 770
Power 750

810
820

830
840

860
850
870

Median nerve
Ulnar nerve
810
820
820
820
820
810
810
810

Radial nerve
810 820

1400

1410

1420

1430

1440

1410

1470

1450

1452
1450

1450
1452

1450

1452

1460
Spine
C2-C8

Target nerve
Conductive tattoo 1600
Arm
1604

1604
1602 Correctly positioned electrodes
1600

1604
1600
1602 Incorrectly positioned electrodes still stimulate the nerve 1604
1600
Alternate tattoo configuration FIG. 18A
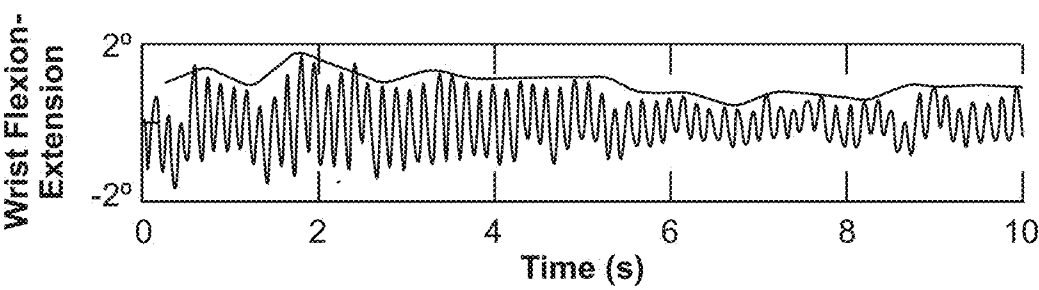
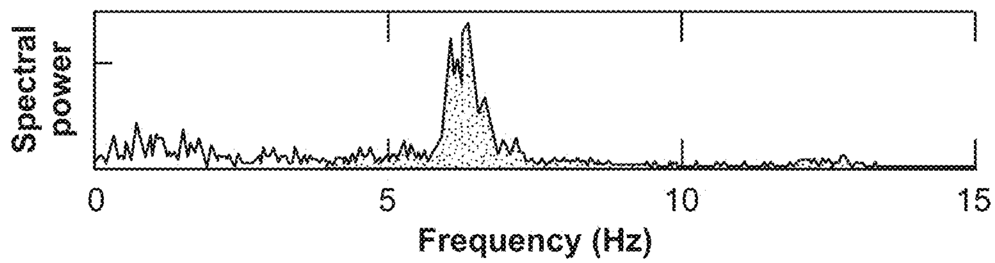
FIG. 18B FIG. 21A
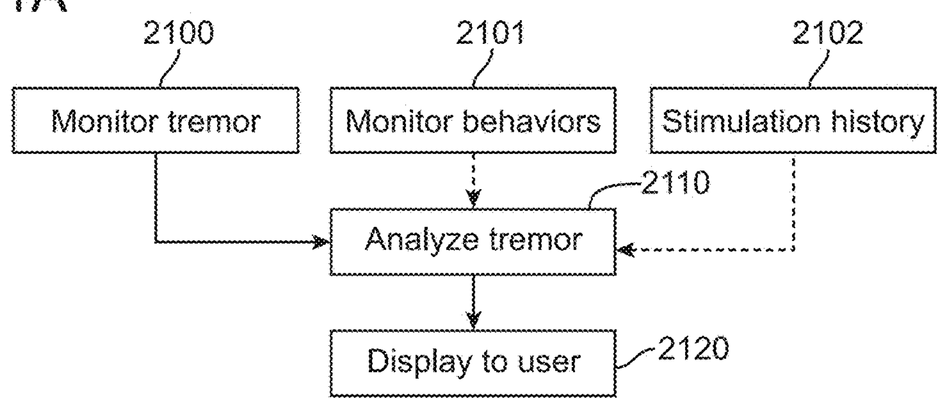
FIG. 21B
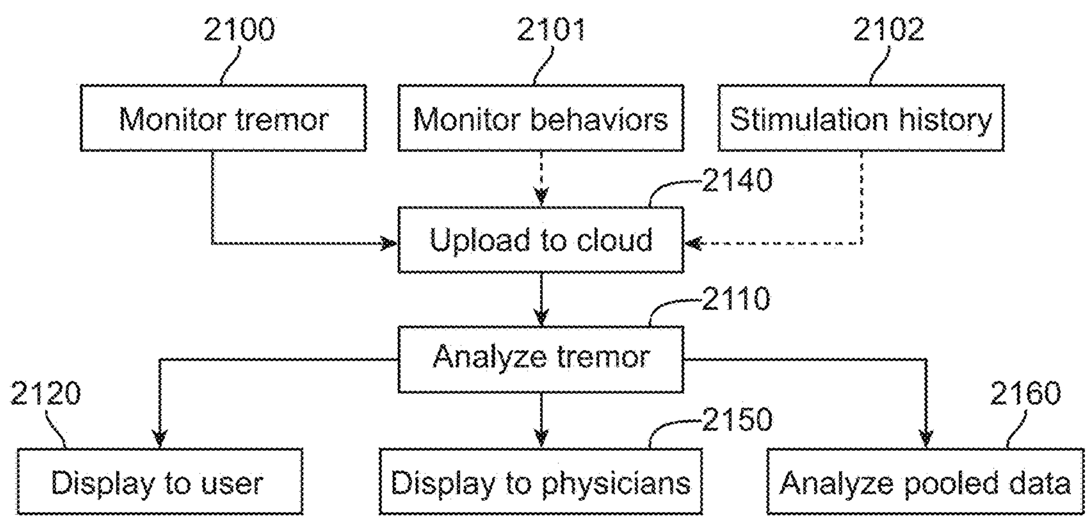
FIG. 21C
FIG. 21D
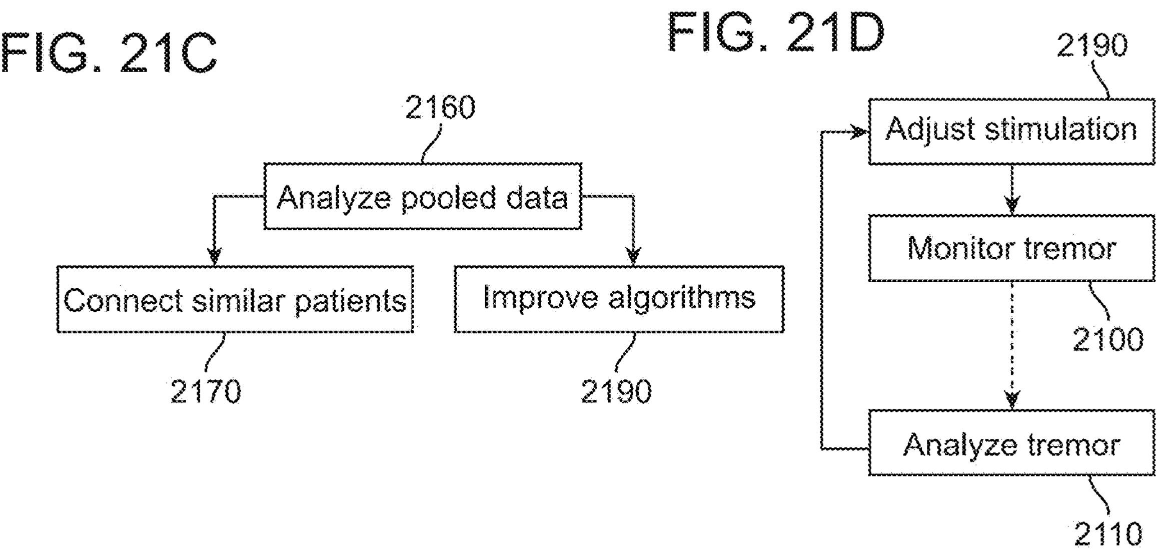

NEEDLE INSERTION

IMPLANTED MICROELECTRODE
IN COMMUNICATION
WITH EXTERNAL DEVICE

INFO TRANSFER
FROM IMPLANT
TO EXTERNAL
LISTENER DEVICE 2406
2404
2400

POWER TRANSFER BY
RF FROM EXTERNAL
DRVICE TO IMPLANT

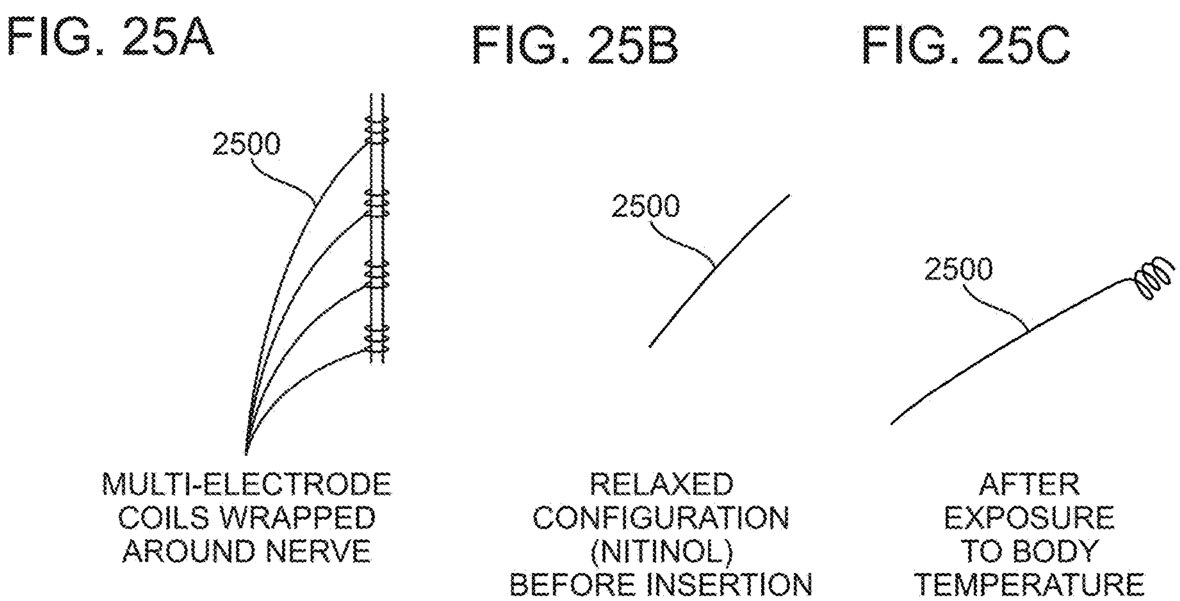
FIG. 25A
2500
MULTI-ELECTRODE COILS WRAPPED AROUND NERVE
FIG. 25B
2500
RELAXED CONFIGURATION (NITINOL) BEFORE INSERTION
FIG. 25C
2500
AFTER EXPOSURE TO BODY TEMPERATURE
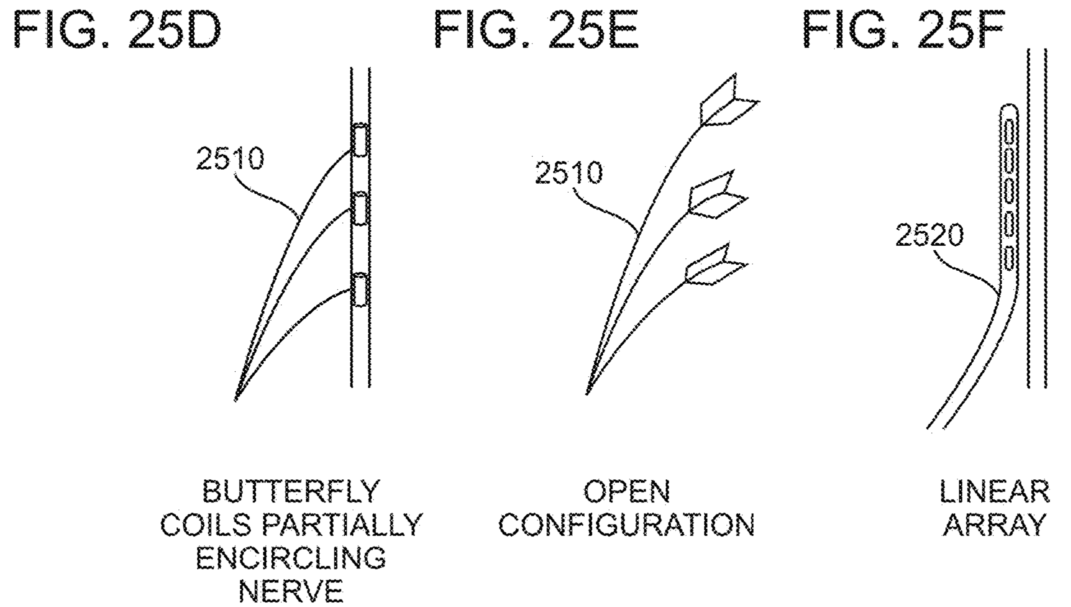
FIG. 25D
2510
BUTTERFLY COILS PARTIALLY ENCIRCLING NERVE
FIG. 25E
2510
OPEN CONFIGURATION
FIG. 25F
2520
LINEAR ARRAY

DEVICES AND METHODS FOR CONTROLLING TREMOR

CROSS REFERENCE TO RELATED APPLICATIONS

This application is a continuation of U.S. patent application Ser. No. 17/107,435, filed Nov. 30, 2020, titled "DEVICES AND METHODS FOR CONTROLLING TREMOR," now U.S. Pat. No. 12,161,858, which is a continuation of U.S. patent application Ser. No. 15/277,946, filed Sep. 27, 2016, titled "DEVICES AND METHODS FOR CONTROLLING TREMOR," now U.S. Pat. No. 10,850,090, which is in turn a continuation of U.S. patent application Ser. No. 14/805,385, filed Jul. 21, 2015, titled "DEVICES AND METHODS FOR CONTROLLING TREMOR," now U.S. Pat. No. 9,452,287, which is a continuation of International Patent Application No. PCT/US2014/012388, filed Jan. 21, 2014, titled "DEVICES AND METHODS FOR CONTROLLING TREMOR," now Publication No. WO 2014/113813, which claims priority to U.S. Provisional Patent Application No. 61/754,945, filed Jan. 21, 2013, titled "DEVICES AND METHODS FOR CONTROLLING TREMOR," U.S. Provisional Patent Application No. 61/786,549, filed Mar. 15, 2013, titled "USER CONTROLLABLE DEVICE TO REDUCE ESSENTIAL TREMOR VIA NEUROMODULATION," U.S. Provisional Patent Application No. 61/815,919, filed Apr. 25, 2013, titled "DEVICES AND METHODS FOR INFLUENCING PERIPHERAL NERVES TO TREAT ESSENTIAL TREMOR, PARKINSON'S DISEASE, AND OTHER NEURODEGENERATIVE OR NEUROMUSCULAR DISORDERS," U.S. Provisional Patent Application No. 61/822,215, filed May 10, 2013, titled "DEVICES AND METHODS FOR CONTROLLING TREMOR," and U.S. Provisional Patent Application No. 61/857,248, filed Jul. 23, 2013 and titled "DEVICES AND METHODS FOR CONTROLLING TREMOR," each of the foregoing of which are herein incorporated by reference in their entireties.

INCORPORATED BY REFERENCE

All publications and patent applications mentioned in this specification are herein incorporated by reference to the same extent as if each individual publication or patent application was specifically and individually indicated to be incorporated by reference.

FIELD

Embodiments of the invention relate generally to systems, devices, and methods for treating tremor, and more specifically relate to system, devices, and methods for treating tremor by stimulation of a peripheral nerve.

BACKGROUND

Essential tremor (ET) is the most common movement disorder, affecting an estimated 10 million patients in the U.S., with growing numbers due to the aging population. The prevalence of ET rises with age, increasing from 6.3% of the population over 65, to above 20% in the population over 95. ET is characterized by an involuntary oscillatory movement, typically between 4-12 Hz. It can produce oscillations in the voice and unwanted movements of the head and limbs. Tremor in the hands and forearm is especially prevalent and problematic because it makes it difficult to write, type, eat, and drink. Unlike Parkinson's tremor, which exists at rest, essential tremor is postural and kinetic, meaning tremor is induced by holding a limb against gravity or during movement, respectively.

Disability with ET is variable, and ranges from embarrassment to the inability to live independently when tasks such as writing and self-feeding are not possible due to the uncontrolled movements of the hand and arm. Despite the high prevalence and high disability in many patients with ET, there are insufficient treatment options to address tremor.

The drugs used to treat tremor (e.g., Propanolol and Primidone) have been found to be effective in reducing tremor amplitude by only 50% in only 60% of patients. These drugs have side effects that can be severe and are not tolerated by many patients with ET. An alternative treatment is surgical implantation of a stimulator within the brain using deep brain stimulation (DBS), which can be effective in reducing tremor amplitude by 90%, but is a highly invasive surgical procedure that carries significant risks and cannot be tolerated by many ET patients. Thus, there is a great need for alternative treatments for ET patients that reduce tremors without the side effects of drugs and without the risks of brain surgery.

Tremor is also a significant problem for patients with orthostatic tremor, multiple sclerosis and Parkinson's Disease. A variety of neurological disorders include tremor such as stroke, alcoholism, alcohol withdrawal, peripheral neuropathy, Wilson's disease, Creutzfeldt-Jacob disease, Guillain-Barré syndrome and fragile X syndrome, as well as brain tumors, low blood sugar, hyperthyroidism, hypoparathyroidism, insulinoma, normal aging, and traumatic brain injury. Stuttering or stammering may also be a form of tremor. The underlying etiology of tremor in these conditions may differ from ET; however, treatment options for some of these conditions are also limited and alternative treatments are needed.

ET is thought to be caused by abnormalities in the circuit dynamics associated with movement production and control. Previous work has shown that these circuit dynamics may be temporarily altered by cooling, topical analgesics and vibration. Previous work reported that electrical stimulation using transcutaneous electrical nerve stimulation (TENS) did not improve tremor (Munhoz 2003). It was therefore surprising to discover in our clinical study that circuit dynamics associated with ET can be altered by peripheral nerve simulation resulting in a substantial reduction in the tremor of individuals with ET.

The present invention is a novel peripheral stimulation device to send signals along the sensory nerves to the central nervous system in order to modify the abnormal network dynamics. Over time, this stimulation normalizes the neural firing in the abnormal network and reduces tremor. While DBS stimulates the brain directly, our peripheral stimulation influences the abnormal brain circuit dynamics by sending signals along the sensory nerves that connect the periphery to the brain. This approach is non-invasive and expected to avoid DBS's surgical risks and associated problems with cognitive, declarative and spatial memory dysarthria, ataxia or gait disturbances. The peripheral nerve stimulation may effectively treat tremors by dephasing, overriding or obscuring the abnormal brain circuit dynamics. Overriding, obscuring or training the brain to ignore the abnormal brain circuit dynamics follows on hypotheses for the mechanisms of traditional DBS.

Perhaps the technology most closely related to our approach is transcutaneous electrical nerve stimulation (TENS). High-frequency TENS (50 to 250 Hz) is commonly used to treat pain, with the hypothesis that excitation of large, myelinated peripheral proprioceptive fibers (A-beta) blocks incoming pain signals. While the inconsistent clinical results achieved using TENS for pain control have led many to question its use for treatment of pain, it is well documented that surface electrical stimulation excites A-beta neurons. A-beta neurons communicate proprioceptive sensory information into the same brain circuits that are abnormal in diseases including ET and Parkinson's disease. Without being limited by any proposed mechanism of action, this has led us to propose that neurostimulation could be used to excite A-beta nerves and thereby improve tremor. This proposal is particularly surprising because a previous study by Munhoz et al. failed to find any significant improvement in any of the tremor parameters tested after application of TENS. See Munhoz et al., Acute Effect of Transcutaneous Electrical Nerve Stimulation on Tremor, Movement Disorders, 18(2), 191-194 (2003).

SUMMARY OF THE DISCLOSURE

The present invention relates systems, devices, and methods for treating tremor, and more specifically relate to system, devices, and methods for treating tremor by stimulation of a peripheral nerve.

In some embodiments, a method of reducing tremor in a patient is provided. The method includes placing a first peripheral nerve effector at a first location relative to a first peripheral nerve; delivering a first stimulus to the first peripheral nerve through the first peripheral nerve effector; and reducing the tremor amplitude by modifying the patient's neural network dynamics.

In some embodiments, the placing step comprises placing the first peripheral nerve effector on the patient's skin and the first stimulus is an electrical stimulus applied to a skin surface.

In some embodiments, the first stimulus has an amplitude from about 0.1 mA to 10 mA and a frequency from about 10 to 5000 Hz. In some embodiments, the first stimulus has an amplitude that is less than about 15, 14, 13, 12, 11, 10, 9, 8, 7, 6, 5, 4, 3, 2 or 1 mA.

In some embodiments, the placing step comprises implanting the first peripheral nerve effector in the patient and the first stimulus is an electrical stimulus.

In some embodiments, the implanting step comprises injecting the first peripheral nerve effector in the patient. In some embodiments, the first stimulus has an amplitude less than about 3 mA and a frequency from about 10 to 5000 Hz. In some embodiments, the first stimulus has an amplitude that is less than about 5, 4, 3, 2 or 1 mA.

In some embodiments, the peripheral nerve effector includes a power source.

In some embodiments, the method further includes powering the first peripheral nerve effector wirelessly through an externally located power source.

In some embodiments, the first stimulus is vibrotactile.

In some embodiments, the first stimulus is chemical.

In some embodiments, the method further includes sensing motion of the patient's extremity using a measurement unit to generate motion data; and determining tremor information from the motion data.

In some embodiments, the delivery step comprises delivering the first stimulus based on the tremor information.

In some embodiments, the tremor information comprises a maximum deviation from a resting position for the patient's extremity.

In some embodiments, the tremor information comprises a resting position for the patient's extremity.

In some embodiments, the tremor information comprises tremor frequency, phase, and amplitude.

In some embodiments, the step of delivering the first stimulus comprises delivering a plurality of bursts of stimulation having a variable temporal delay between the bursts of stimulation.

In some embodiments, the method further includes placing a second peripheral nerve effector at a second location relative to a second peripheral nerve; and delivering a second stimulus to the second peripheral nerve through the second peripheral nerve effector.

In some embodiments, the method further includes determining a period of the patient's tremor, wherein the step of delivering the second stimulus comprises offsetting delivery of the second stimulus from the delivery of the first stimulus by a predetermined fraction or multiple of a period of the tremor.

In some embodiments, the method further includes dephasing the synchronicity of a neural network in the patient's brain.

In some embodiments, the first location and second location are located on adjacent fingers.

In some embodiments, the first peripheral nerve and the second peripheral nerve are adjacent nerves.

In some embodiments, the first peripheral nerve is the median nerve and the second peripheral nerve is the ulnar or radial nerve.

In some embodiments, the first peripheral nerve and the second peripheral nerve are somatotopically adjacent.

In some embodiments, the first stimulus has an amplitude that is below a sensory threshold.

In some embodiments, the first stimulus is greater than 15 Hz.

In some embodiments, the first peripheral nerve carries proprioceptive information from the patient's extremity.

In some embodiments, the method further includes determining a duration of efficacy of the first stimulus on reducing the tremor amplitude; and delivering a second stimulus before the expiration of the duration of efficacy.

In some embodiments, the step of determining the duration of effect comprises analyzing multiple stimuli applications applied over a predetermined period of time.

In some embodiments, the step of determining the duration of efficacy further comprises determining an activity profile for the patient.

In some embodiments, the step of determining the duration of efficacy further comprises determining a profile of the tremor.

In some embodiments, the activity profile includes data regarding caffeine and alcohol consumption.

In some embodiments, the method further includes placing a conduction pathway enhancer over the first peripheral nerve.

In some embodiments, the conduction pathway enhancer is a conductive tattoo.

In some embodiments, the conduction pathway enhancer comprises one or more conductive strips.

In some embodiments, the first location is selected from the group consisting of a wrist, a forearm, a carpel tunnel, a finger, and an upper arm.

In some embodiments, a system for treating tremor in a patient is provided. The device can include a decision unit; and an interface unit adapted to deliver electrical stimuli to a peripheral nerve, the interface unit comprising a first peripheral nerve effector in communication with the decision unit, the first peripheral nerve effector comprising at least one electrode; wherein the decision unit comprises a processor and a memory storing instructions that, when executed by the processor, cause the decision unit to: deliver a first electrical stimulus to a first peripheral nerve through the first peripheral nerve effector, the electrical stimulus configured by the controller to reduce tremor in the patient's extremity by modifying the patient's neural network dynamics.

In some embodiments, the first electrical stimulus has an amplitude less than about 10 mA and a frequency from about 10 to 5000 Hz. In some embodiments, the amplitude is less than about 15, 14, 13, 12, 11, 10, 9, 8, 7, 6, 5, 4, 3, 2, or 1 mA.

In some embodiments, the interface unit further comprises a second peripheral nerve effector in communication with the decision unit, the second peripheral nerve effector comprising at least one electrode, wherein the memory storing instructions that, when executed by the processor, further cause the decision unit to deliver a second electrical stimulus to a second peripheral nerve in the patient's extremity through the second peripheral nerve effector.

In some embodiments, the instructions, when executed by the processor, cause the decision unit to deliver the second electrical stimulus offset in time from the first electrical stimulus by a predetermined fraction or multiple a period of the tremor.

In some embodiments, the first peripheral nerve effector is adapted to be placed on a first finger and the second peripheral nerve effector is adapted to be placed on a second finger.

In some embodiments, the first peripheral nerve effector comprises a plurality of electrodes arranged in linear array. In some embodiments, the plurality of electrodes are spaced about 1 to 100 mm apart.

In some embodiments, the first peripheral nerve effector comprises a plurality of electrodes arranged in a two dimensional array.

In some embodiments, the memory storing instructions that, when executed by the processor, further cause the decision unit to select a subset of the plurality of electrodes based on a position of first peripheral nerve effector on the patient's extremity, wherein the selection of the subset of the plurality of electrodes occurs each time the first peripheral nerve effector is positioned or repositioned on the extremity.

In some embodiments, the plurality of electrodes are spaced about 1 to 100 mm apart along a first axis and about 1 to 100 mm apart along a second axis perpendicular to the first axis. In some embodiments, some of the electrodes are adjacent to each other to form a strip. In some embodiments, the spacing can be less than about 100, 90, 80, 70, 60, 50, 40, 30, 20, 10, 5, 4, 3, 2, or 1 mm.

In some embodiments, the system further includes a measurement unit, wherein the memory storing instructions that, when executed by the processor, further cause the decision unit to: measure the movement of the patient's extremity using the measurement unit to generate motion data; and determine a tremor frequency and magnitude based on an analysis of the motion data.

In some embodiments, the analysis of the motion data comprises a frequency analysis of the spectral power of the movement data.

In some embodiments, the frequency analysis is restricted to between about 4 to 12 Hz. In some embodiments, the frequency analysis is restricted to approximately the expected frequency range of the tremor or tremors of concern.

In some embodiments, the analysis of the motion data is done on a predetermined length of time of the motion data.

In some embodiments, the decision unit is further adapted to determine tremor phase information based on the motion data and to deliver the first electrical stimulus based on the tremor phase information.

In some embodiments, the tremor phase information comprises peak tremor deviation, the decision unit being further adapted to deliver the first electrical stimulus at a time corresponding to the peak tremor deviation.

In some embodiments, the memory storing instructions that, when executed by the processor, further cause the decision unit to deliver the first electrical stimulus as a plurality of bursts of electrical stimulation having a variable temporal delay between the bursts of electrical stimulation.

In some embodiments, the memory storing instructions that, when executed by the processor, further cause the decision unit to set parameters of the first electrical stimulus based on the determined tremor frequency.

In some embodiments, the memory storing instructions that, when executed by the processor, further cause the decision unit to set parameters of the first electrical stimulus based on the determined tremor magnitude.

In some embodiments, the memory storing instructions that, when executed by the processor, further cause the decision unit to compare the determined tremor magnitude with a predetermined threshold; and wherein the first electrical stimulus is delivered when the determined tremor magnitude exceeds a predetermined threshold.

In some embodiments, the electrode is adapted to deliver the first electrical stimulus through the patient's skin.

In some embodiments, the electrode is adapted to be implanted and deliver the electrical In some embodiments, the decision unit comprises a user interface adapted to accept input from a user to adjust a parameter of the first electrical stimulus.

In some embodiments, the memory further stores a library of one or more predetermined stimulation protocols.

In some embodiments, the interface unit is integrated with the decision unit.

In some embodiments, the interface unit and the decision unit are separate from each other and have separate housings.

In some embodiments, the decision unit is configured to wirelessly provide power to, or communicate with, the interface unit.

In some embodiments, the system further includes a measurement unit located in the decision unit.

In some embodiments, the system further includes a measurement unit located in the interface unit.

In some embodiments, the decision unit is a computing device selected from the group consisting of a smartphone, tablet and laptop.

In some embodiments, the system further includes a server in communication with the computing device, the server configured to receive from the computing device motion data along with a history of the electrical stimuli delivered to the patient.

In some embodiments, the server is programmed to: add the received motion data and the history of the electrical stimuli delivered to the patient to a database storing data from a plurality of patients.

In some embodiments, the server is programmed to: compare the received motion data and the history of the electrical stimuli delivered to the patient to the data stored in the database; determine a modified electrical stimulus protocol based on the comparison of the received motion data and the history of the electrical stimuli delivered to the patient to the data stored in the database; and transmit the modified electrical stimulus protocol to the computing device.

In some embodiments, the electronics are flexible and are disposed on a flexible substrate, which can be a sleeve, pad, band, or other housing.

In some embodiments, a system for monitoring tremor in a patient's extremity is provided. The system can include an interface unit having an inertial motion unit for capturing motion data, a power source and a wireless transmitter and receiver, the interface unit adapted to be worn on the patient's extremity; and a processing unit in communication with the interface unit, the processing unit configured to receive the motion data from the interface unit, wherein the processing unit is programmed to: determine a tremor signature and profile over a predetermined period of time based on an analysis of the motion data.

In some embodiments, the processing unit is a mobile phone.

In some embodiments, the system further includes a server in communication with the mobile phone, the server configured to receive motion data from the mobile phone.

In some embodiments, the processing unit is further programmed to compare the tremor magnitude with a predetermined threshold.

In some embodiments, the processing unit is further programmed to generate an alert when the tremor magnitude exceeds the predetermined threshold.

In some embodiments, the predetermined threshold is adjustable by the patient.

In some embodiments, the processing unit is programmed to prompt the patient to enter activity data, the activity data including a description of the activity and a time the activity occurred.

In some embodiments, the processing unit is programmed to correlate the activity data with the determined tremor frequency and magnitude.

In some embodiments, the activity data comprises consumption of caffeine or alcohol.

In some embodiments, the activity data comprises consumption of a drug.

We have invented a peripheral nerve stimulation device and method that effectively reduces tremors without the side effects of drugs and without the risks of brain surgery. Our approach is safe, and in some embodiments non-invasive, and effective in reducing tremor. In some embodiments, the device may work by altering the neural circuit dynamics associated with essential tremor, Parkinson's tremor, and other tremors. The device is simple to use, comfortable, and adjustable to achieve the best therapy for each patient.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 3A shows the tremor before treatment; FIG. 3B shows the reduction in tremor immediately after treatment; FIG. 3C shows that the tremor reduction is maintained twenty minutes after the treatment.

FIG. 14E is a drawing showing an embodiment in which the stimulator is mechanical. FIG. 14H illustrates an embodiment of a device having a form factor of a wrist watch. FIG. 14I illustrates the back of the device shown in FIG. 14H, showing the electrodes which are the interface with the user. FIGS. 14J and 14K illustrate an embodiment of a disposable electrode interface that snaps into place of the wrist watch form factor of the device housing. FIG. 14L illustrates an embodiment of a self aligning snap feature that allows the disposable electrode interface to snap into the housing of the device in a wrist watch form factor. FIG. 14M is a drawing showing the potential placement of electrodes along the spine in an embodiment of the device where the effector is electrical.

FIGS. 18A and 18B illustrate an example of spectral analysis of gyroscopic motion data for a patient with a tremor centered at 6.5 Hz.

FIGS. 21A-21D are flowcharts showing the monitoring, integration, analysis and display of data used to inform the users or improve the stimulation.

FIGS. 24A-24D illustrate various embodiments of implantable devices and skin surface devices allowing wireless power and control.

FIGS. 25A-25F illustrate various geometries of electrodes for implanted electrical stimulation.

DETAILED DESCRIPTION OF THE PREFERRED EMBODIMENT

Definition of Terms

As used herein, the terms "stimulating" and "stimulator" generally refer to delivery of a signal, stimulus, or impulse to neural tissue of the targeted region. The effect of such stimulation on neuronal activity is termed "modulation;" however, for simplicity, the terms "stimulating" and "modulating," and variants thereof, are sometimes used interchangeably herein. The effect of delivery of the signal to the neural tissue may be excitatory or inhibitory and may potentiate acute and/or long-term changes in neuronal activity. For example, the effect of "stimulating" or "modulating" a neural tissue may comprise one or more of the following effects: (a) depolarizing the neurons such that the neurons fire action potentials, (b) hyperpolarizing the neurons to inhibit action potentials, (c) depleting neurons ion stores to inhibit firing action potentials (d) altering with proprioceptive input, (e) influencing muscle contractions, (f) affecting changes in neurotransmitter release or uptake, or (g) inhibiting firing. "Proprioception" refers to one's sensation of the relative position of one's own body parts or the effort being employed to move one's body part. Proprioception may otherwise be referred to as somatosensory, kinesthetic or haptic sensation. A "proprioceptor" is a receptor providing proprioceptive information to the nervous system and includes stretch receptors in muscles, joints, ligaments, and tendons as well as receptors for pressure, temperature, light and sound. An "effector" is the mechanism by which the device modulates the target nerve. For example, the "effector" may be electrical stimulation of the nerve or mechanical stimulation of proprioceptors.

"Electrical stimulation" refers to the application of electrical signals to the soft-tissue and nerves of the targeted area. "Vibrotactile stimulation" refers to excitation of the proprioceptors, as by application of a biomechanical load to the soft-tissue and nerves of the targeted area. Applying "thermal stimulation" refers to induced cooling or heating of the targeted area. Applying "chemical stimulation" refers to delivery of either chemical, drug or pharmaceutical agents capable of stimulating neuronal activity in a nerve or in neural tissue exposed to such agent. This includes local anesthetic agents that affect neurotransmitter release or uptake in neurons, electrically excitable cells that process and transmit information through electrical and chemical signals. The "cloud" refers to a network of computers communication using real-time protocols such as the internet to analyze, display and interact with data across distributed devices.

Clinical Study

Figure 1:
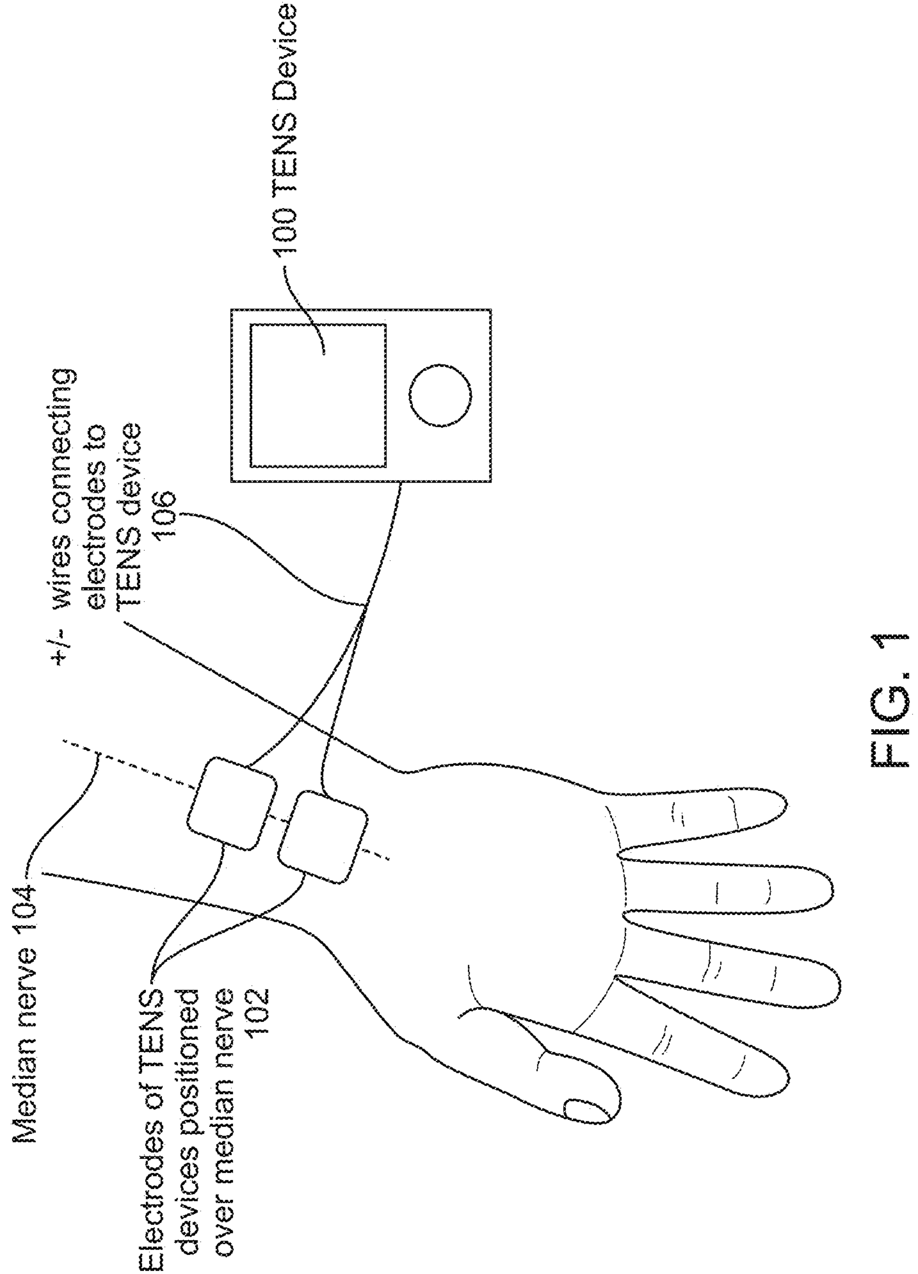
FIG. 1 illustrates one embodiment of delivering stimulation to the median nerve found to reduce tremor.

We evaluated the method of using peripheral nerve stimulation to alter the circuit dynamics associated with ET in a clinical study. A device 100 that delivers transcutaneous electrical nerve simulation (TENS) using surface electrodes 102 positioned on the palmar side of the wrist was used to stimulate the median nerve 104 with square waves at a frequency of 150 Hz with a pulse width of 300 microseconds for 40 minutes, as illustrated in FIG. 1. Wires 106 were used in this embodiment to connect the device 100 to the electrodes 102. It was surprising to discover that the tremor was reduced because previous work reported that peripheral nerve stimulation using TENS did not improve tremor (Munhoz 2003, referenced above).

This electrical stimulation effectively reduced the tremor in subjects with tremors ranging in severity from mild to severe. Kinetic tremors were evaluated using a widely used measure of kinetic tremor: the Archimedes Spiral drawing task of the Fahn Tolosa Marin test. Postural tremors were evaluated by measuring the angular velocity of gyroscopes worn on the back on the hand.

Figures 2A, 2B, 2C:
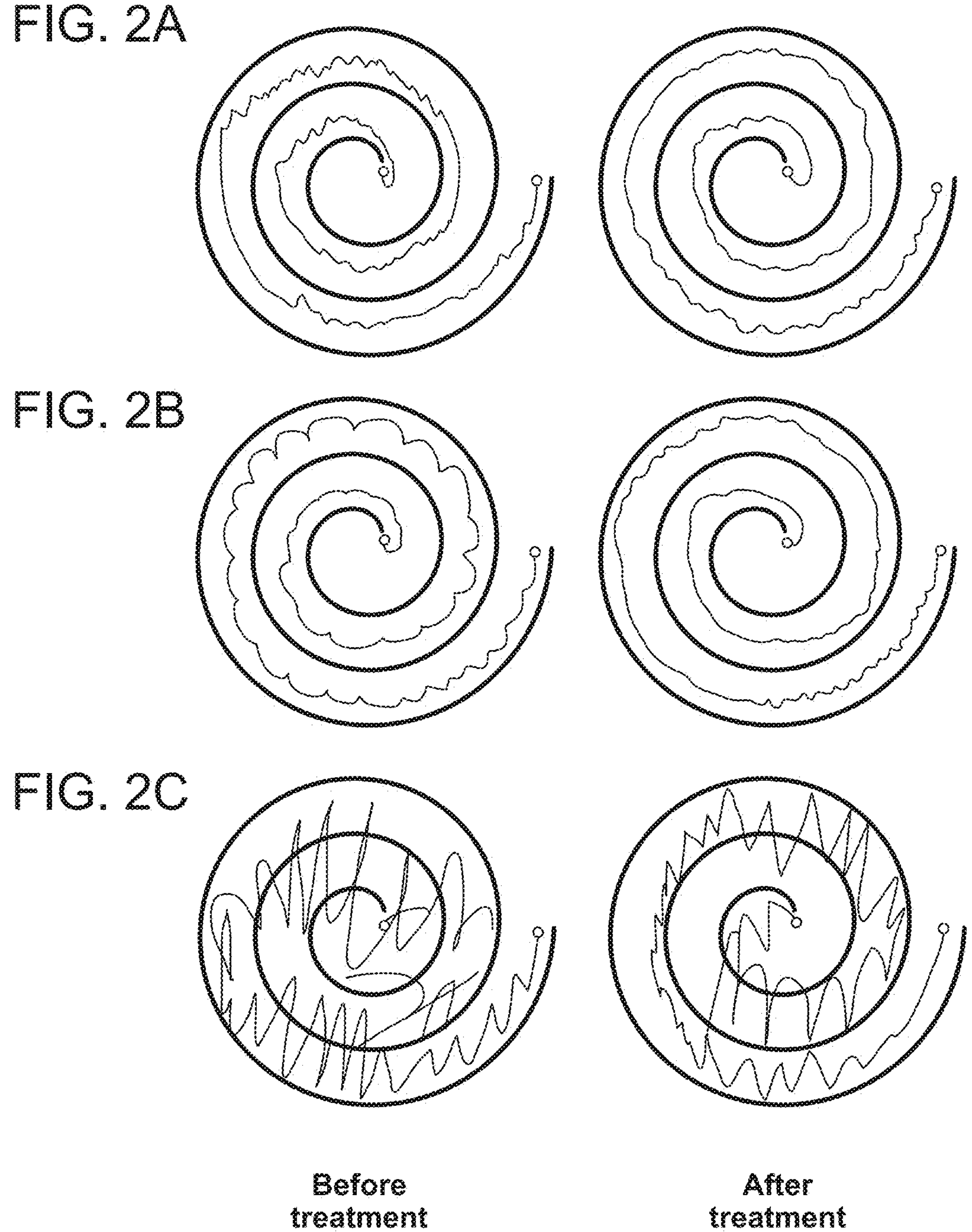
FIGS. 2A-2C illustrate treatment effect of an embodiment of peripheral nerve stimulation in a (FIG. 2A) mild, (FIG. 2B) moderate and (FIG. 2C) severe ET patient. It presents results of a clinical study in which a patient with essential tremor reduced tremor amplitude by the configuration of stimulation at 150 Hz frequency, 300 us, and for 40 minutes of stimulation on-time. The tremor reduction, shown by comparing the ET patient's ability to draw a spiral, was observed immediately after the stimulation was turned off.
Figures 3A, 3B, 3C:
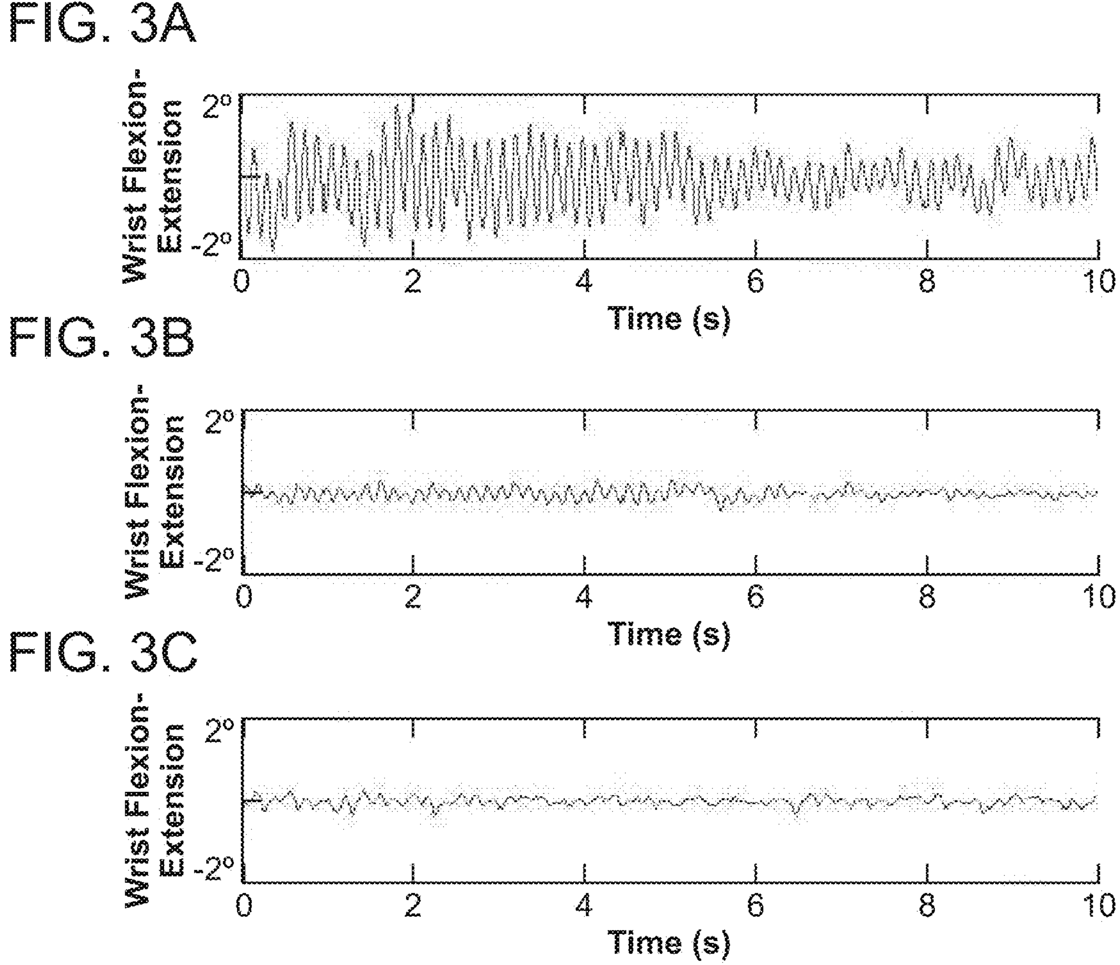
FIGS. 3A-3C illustrate wrist flexion-extension calculated from gyroscopic data in subject B from FIGS. 2A-2C.
Figure 4:
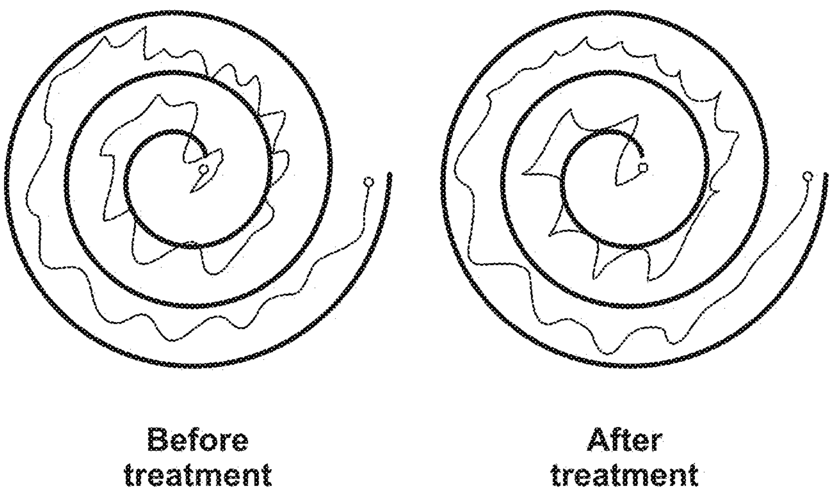
FIG. 4 illustrates an example of ineffective treatment in a moderate ET patient.

Three patients, represented as subject A, B and C in FIG. 2, show spirals drawn by subjects with mild, moderate and severe ET before and after stimulation. The postural tremor reductions were 70%, 78% and 92%, respectively, in the subjects with mild, moderate and severe tremor. Postural tremor could also be reduced with electrical stimulation, and this effect was maintained up to 45 minutes after the end of treatment. FIGS. 3A-3C shows the effect on wrist flexion-extension as determined from gyroscopic data in subject B from FIG. 2 as a representative example. Fifteen minutes of treatment reduced the tremor amplitude from 0.9 degrees (FIG. 3A) to 0.2 degrees (FIG. 3B). This reduction in tremor amplitude was maintained through 40 minutes of treatment. A measurement taken 20 minutes after treatment showed the tremor amplitude continued to be reduced and was maintained at 0.2 degrees (FIG. 3C). The tremor reduction was variable between subjects. Some subjects did not respond to therapy, as shown in FIG. 4.

Great therapeutic results were achieved by reducing the tremor in subjects with ET through the application of electrical stimulation. The stimulation was able to reduce tremor during the treatment, immediately after the treatment, and up to twenty minutes after treatment. To enable chronic use and allow patients with ET to integrate the treatment into their lives, it is important to make the system convenient to use and effective over a long duration. The following innovations and devices achieve this goal.

Device Location

Figure 5:
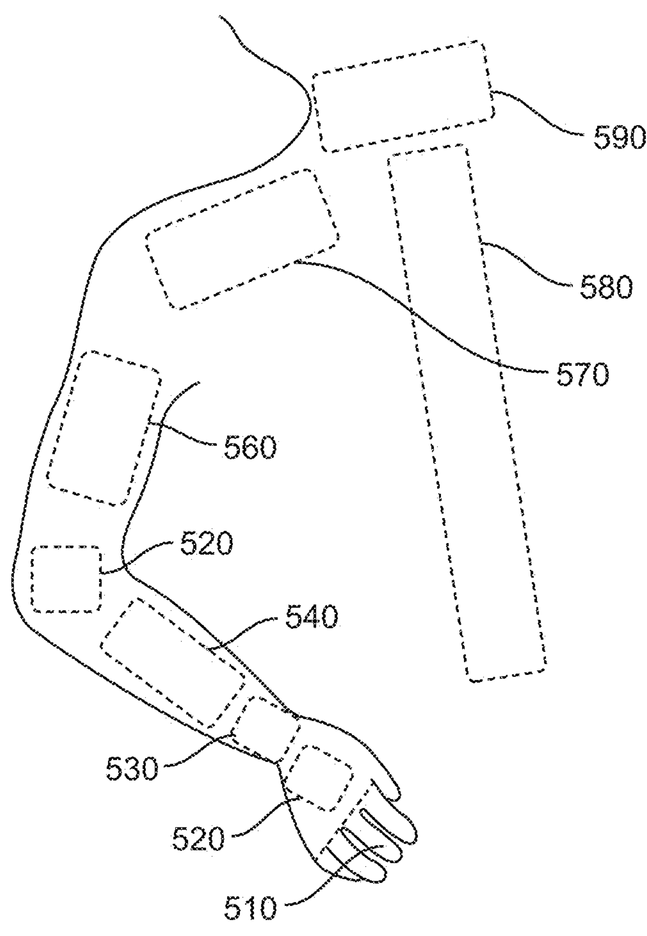
FIG. 5 illustrates various positions on a patient where the tremor altering system can be located.

The device stimulates the sensory nerves in order to modify the abnormal network dynamics. Over time, this stimulation normalizes the neural firing in the abnormal network and reduces tremor. Preferentially, the stimulated nerve is a nerve that carries sensory proprioceptive information from the limb affected by the tremor. The nerve may be modulated directly, such as by electrical stimulation anywhere along or adjacent to a nerve carrying proprioceptive information. Alternatively, the target nerve may be modulated indirectly, such as by excitation of the proprioceptors that stimulate the target nerve. FIG. 5 shows access points to nerves carrying proprioceptive information from a limb or vocal cords or larynx. These access points can include, but are not limited to, the fingers (510), the hand (520), the wrist (530), the lower arm (540), the elbow (550), the upper arm (560), the shoulder (570), the spine (580) or the neck (590), foot, ankle, lower leg, knee, or upper leg. Nerves affecting proprioception can include, for example, the median, ulnar, radial, or other nerves in the hand, arm, and spinal area, or along muscle or within joints. These regions target to the nerves may include the brachial plexus, medial nerves, radial nerves, and ulnar, dermal, or joint space nerves. These regions may also target the musculature including muscles of the shoulder, muscles of the arm, and muscles of the forearm, hand, or fingers. Muscles of the shoulder may include, by non-limiting example, the deltoid, teres major and supraspinatus. Muscles of the arm may include the coracobrachialis and triceps brachii. Muscles of the forearm may include the extensor carpi radialis longus, abductor pollicis longus, extensor carpi unlarnis, and flexor carpi ulnaris.

In a preferred location, the device interfaces with the dermal surface of the tremulous upper extremities of the user and applies neuromodulatory signals to the nerve bundles selected from the group consisting of the brachial plexus, medial nerves, radial nerves, and ulnar nerves or the excitable structures in the musculature of the upper extremities on the skin or within a joint.

Proprioceptors can be found for example in muscles, tendons, joints, skin, and the inner ear. Criteria defining candidate nerves for direct modulation include the location of the tremor to be reduced and the proximity of the nerve to the skin's surface, high density of proprioceptive fibers, and distance from excitable pain receptors or muscles. The median nerve targeted at the wrist and the ulnar nerve targeted at the elbow rank high by these criteria. Criteria defining candidate location for indirect proprioceptive modulation include the density and type of proprioceptors. Pacinian corpuscles provide information about touch; Muscle spindles provide information about changes in muscle length by triggering action potentials in the muscle spindle afferent nerve when mechanically-gated ion channels open due to muscle stretching; Golgi tendon organs provide information about muscle tension. These structures may also be stimulated to alter circuit dynamics and reduce tremor.

Figures 6A, 6B:
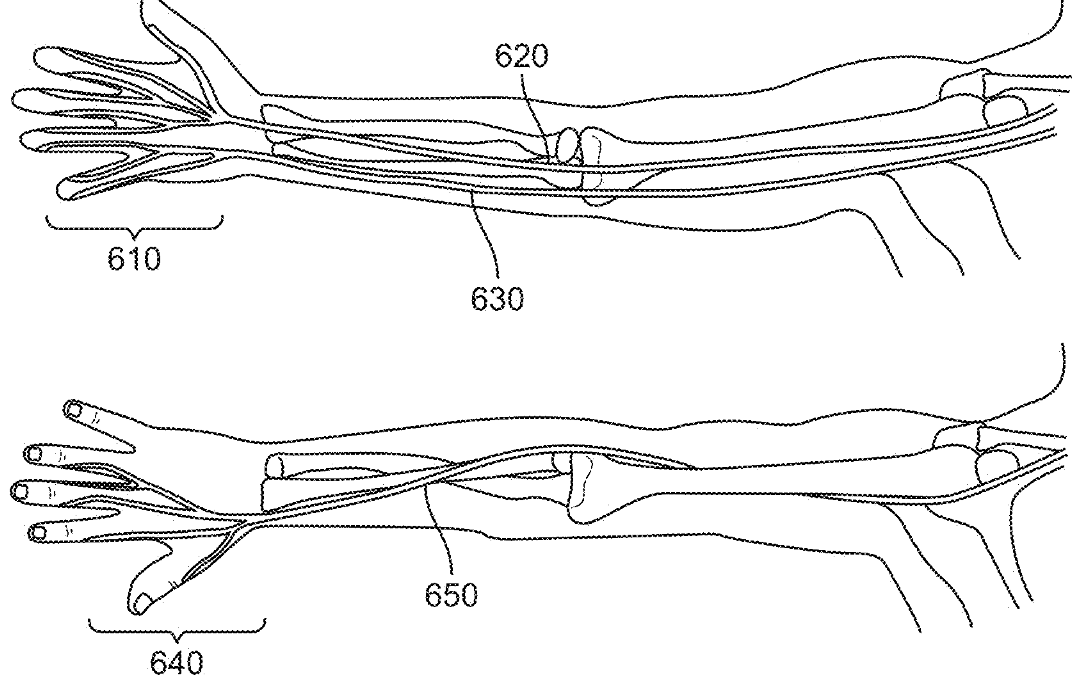
FIGS. 6A and 6B illustrate the major nerves innervating the hand and their distal branches.

The device targets the specific nerves that synapse on the abnormal brain circuit. This synapse may be either direct, or through multiple relay synapses. FIGS. 6A and 6B shows a set of representative nerves that transmit proprioceptive information into the olivo-cerebello network, a network that is abnormal in ET. These nerves include the (610) distal branches and main branches of the (620) median nerve and (630) ulnar nerve, as well as the (640) distal branches and main branches of the (650) radial nerve. In preferred embodiments, this device targets the nerves inputting proprioceptive information from the hand, wrist and forearm.

In another embodiment, the combination of any parts described here within, may be used to affect the nerves associated with voice tremor, including but not limited to branches of the vagus nerve such as the superior laryngeal nerve or the recurrent laryngeal nerve.

Device Components: Various Embodiments

FIGS. 7A-7D are conceptual diagrams illustrating some embodiments of a tremor altering system 700. System 700 includes a housing 720, one or more effectors 730, one or more controls 740 in electrical communication with the effector 730, and one or more power sources 750. The housing 720 can, in some embodiments, include an interface 760. The interface facilitates the coupling of the effector to the patient. For example, the interface can provide a physical, electrical, chemical, thermal or magnetic connection between the device and the patient's nerve. The housing 720 can also, in some embodiments, include a sensor 780 to detect the tremor, memory 770, display 790, and processor 797. The device in this embodiment may include a processor 797 coupled to the effector which could perform computations and control of other components. The device may also include a digital library stored on the processor 797 or memory 770 which could contain preloaded modulation protocols. The device could include a controls module 740 that communicates with the processor 797 and could be used by the user to control stimulation parameters. The controls allow the user to adjust the operation of the device. For example, the controls can be configured to turn the device on, turn the device off, adjust a parameter of the effector, such as the intensity. The device may include a sensor 780 connected to the processor 797 which may detect information of predefined parameters and transmits said parameter information to the processor 797. The device may include a data storage unit 770 connected to the sensor 780 and processor 797; and a power supply 750 may be connected to the processor.

The device may further contain a display or indicators 790 to communicate with the user and report on the status of the device. Indicators are preferably a light-emitting diode (LED) or some visual indicator but can alternatively be an audio indicator. The information may include the battery power or the stimulation status.

The device might not have an Effector 730. It may be a diagnostic non-therapeutic device. In a preferred embodiment, the Interface Unit 704 would be worn on the tremoring limb to track the tremor over time. Providing feedback to the user of the device can make them aware of their tremor and allow monitoring over time. Even without therapeutic stimulation this biofeedback can help some individuals reduce their tremor. Alternatively, the device might not have a Sensor 780. It may be a therapeutic non-diagnostic device.

Figures 7A, 7B, 7C:
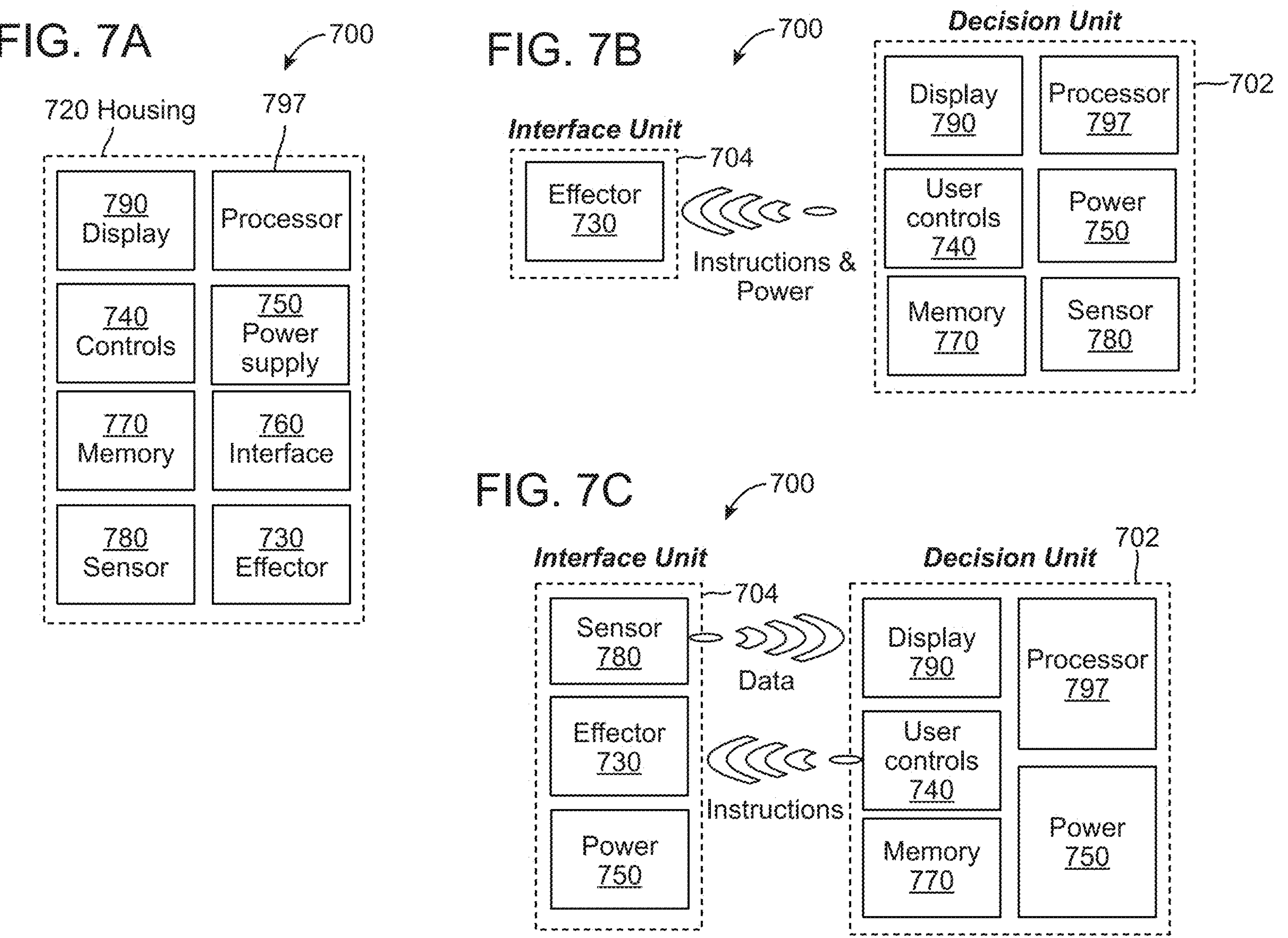
FIGS. 7A-7D are block diagrams illustrating various embodiments of a tremor altering system.
Figure 7D:
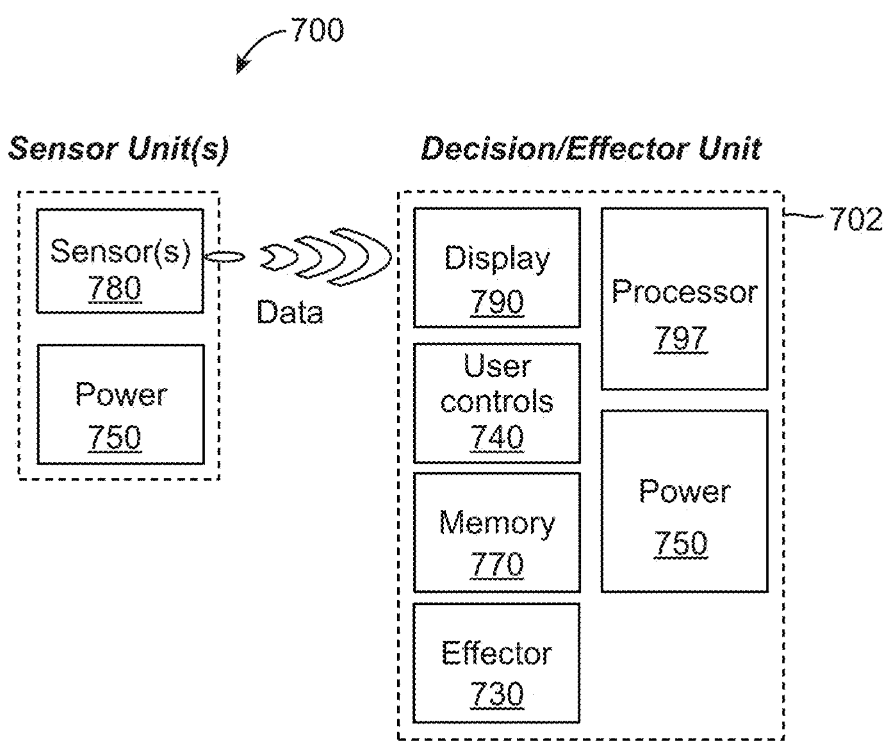

In order to make the device small and simple, many of these components could be housed in a separate unit. Processing, controlling and possibly sensing may be done remotely in a Decision Unit 702, making the Interface Unit 704 that provides the therapeutic contact with the patient compact, simple, and flexible for a variety of applications (FIGS. 7B-7D). This Decision Unit 702 may be a new device designed for this application, or it may be integrated into an existing technology such as a smartphone. This would allow the system to be robust handheld form-factor with a reduced cost and size.

In a preferred embodiment shown in FIG. 7B, the Interface Unit 704 is an implant; the Effector 730 provides electrical stimulation of the nerves; the instruction set and power are transmitted wirelessly from an external device. Alternatively, the implanted Interface Unit 704 may be powered with an on-board battery. Alternatively, the implanted Interface Unit 704 may contain a sensor 780 for direct detection of the tremor or neuromuscular activity detected by electroneurography (ENG) or electromyography (EMG).

In the preferred embodiment shown in FIG. 7C, the Interface Unit 704 is worn on the surface of the body; the Effector 730 provides electrical stimulation of the underlying nerves or vibrotactile stimulation of nearby proprioceptors. The sensor 780 could include motion sensors including accelerometers, gyroscopes and magnetometers.

In the preferred embodiment shown in FIG. 7D, one or more sensor units 780, sensing motion, temperature, etc. may be worn at different locations in the body. The effector 730 and decision unit 702 are a separate entity worn at a different location on the body than the sensors 780. This is useful if stimulation of a nerve occurs in a location where tremor is not as easily or accurately measured. For instance, a stimulation device 700 placed on the underside of the wrist for reducing hand tremor is highly effective. However, measuring tremor of the hand from the wrist using accelerometer or gyroscopes could prove more difficult; a sensor unit placed separately on the palm or backside of the hand in a glove or worn as a ring on one of the digits would show greater sensitivity towards hand tremor since it is located beyond wrist joint.

Effectors: General

The effector may function to modulate the neural tissue in the upper extremity region at which stimulation is directed. For example, the effector can modify neuronal signals in the nerves and/or modify the flow or content of proprioceptive information. The effectors may be delivered transcutaneously or subcutaneously. One or more effectors can be used to influence the nerves. In some embodiments, the effector can be excitatory to the nerve. In other embodiments, the effector can be inhibitory to the nerve. In some embodiments, the system can be used to excite the nerve during some portions of the treatment and inhibit the nerve during other portions of the treatment.

Effector: Electrical Stimulation

In some embodiments, the effector may be an electrical stimulator. Electrical effectors can include an electrode, an electrode pair, an array of electrodes or any device capable of delivering an electrical stimulation to a desired location. Electrical stimulation may be transcutaneous or subcutaneous. For example, transcutaneous electrical stimulation may be achieved with electrodes placed on the surface of the skin while subcutaneous electrical stimulation may be achieved with an implanted electrode positioned close to a nerve.

The stimulation parameters may be adjusted automatically, or controlled by the user. The stimulation parameters may include on/off, time duration, intensity, pulse rate, pulse width, waveform shape, and the ramp of pulse on and off. In one preferred embodiment the pulse rate may be approximately 50 to 5000 Hz, and a preferred frequency of about 50 Hz to 300 Hz, or 150 Hz. A preferred pulse width may range from 50 to 500 μs (micro-seconds), and a preferred pulse width may be approximately 300 μs. The intensity of the electrical stimulation may vary from 0 mA to 500 mA, and a preferred current may be approximately 1 to 6 mA. These preferred settings are derived from the clinical study described above that provided a valuable reduction in tremor sustained for a time period. We note that the electrical stimulation can be adjusted in different patients and with different methods of electrical stimulation; thus, these preferred settings are non-limiting examples. The increment of intensity adjustment may be 0.1 mA to 1.0 mA. In one preferred embodiment the stimulation may last for approximately 10 minutes to 1 hour.

In one preferred embodiment, the electrodes may be in contact with the user at the surface of the skin above one or more nerve(s) that may include the medial, radial, and ulnar nerves. The electrode may be in the configuration where there is an electrode pair, in which one electrode is proximal (closer to the elbow) and another is distal (closer to the hand). The electrodes may be in communication with the opposing electrode. The electrode pair may have a polarity of positive or negative charge in which electrical current passes.

The effector may include two electrodes, each with positive or negative polarity, or an electrode array may include multiple electrode pairs, where each pair is independently programmed or programmed dependently in relation to the other pairs of electrodes. As an example, the program can allow cyclic stimulation of different nerves at different times, such as ulnar, then median, then radial, or any combination thereof.

Electrical stimulation may be designed to suppress tremors by interfering with proprioceptive input, inducing compensatory muscle contractions, or by a combination of both methods. The electrodes may be substituted by any equivalent material capable of conducting electrical signals through the stimulator interface with the dermal surface of the upper extremity. The electrodes may be attached to a control unit 740 which could apply electrical stimulation via the electrodes to the soft tissue and nerves in the region where the electrode are placed and the region immediately surrounding. In another variation of the embodiment, several electrodes can be placed to a combination of targeted regions.

A function generator connected to and controlled by the processor may function to modulate electrical stimulation parameters. The function generator is preferably an arbitrary waveform generator that uses direct digital synthesis techniques to generate any waveform that can be described by a table of amplitudes. The parameters are selected from a group including but not limited to frequency, intensity, pulse width or pulse duration, and overall duration. The outputs preferably have a power limit set by the maximum output voltage. In a preferred embodiment, the digitally stored protocols cycle through various stimulation parameters to prevent patient acclimation. Variation of electrical stimulation is achieved by the function generator.

Optimizing Stimulation: Dephasing

In a preferred embodiment, the stimulation is designed to dephase synchronicity in the brain. The concept of dephasing the abnormal circuit follows on recent work showing neural retraining reduces the network's propensity to fall into an abnormal rhythm. Interestingly, movement disorders are often associated with abnormal periodic synchronous firing in brain circuits. In Parkinson's disease, this circuit is in the basal ganglia. In ET, it is the olivo-cerebellar circuit. These anomalous oscillations are thought to drive the tremor, as supported by numerous studies showing that the tremor observed in the hand and forearm muscles is synched with pathological rhythmic discharges in the brain. Recent DBS studies have shown that low-voltage phase-shifted bursts on adjacent pairs of electrodes (called Coordinated Reset) can reduce synchronization in abnormal brain networks and that this reduces Parkinsonian tremors. The application of Coordinated Reset theory to treat tinnitus supports the concept of using synaptic excitation to retrain neural networks.

Figures 8A, 8B, 8C, 8D, 8E:
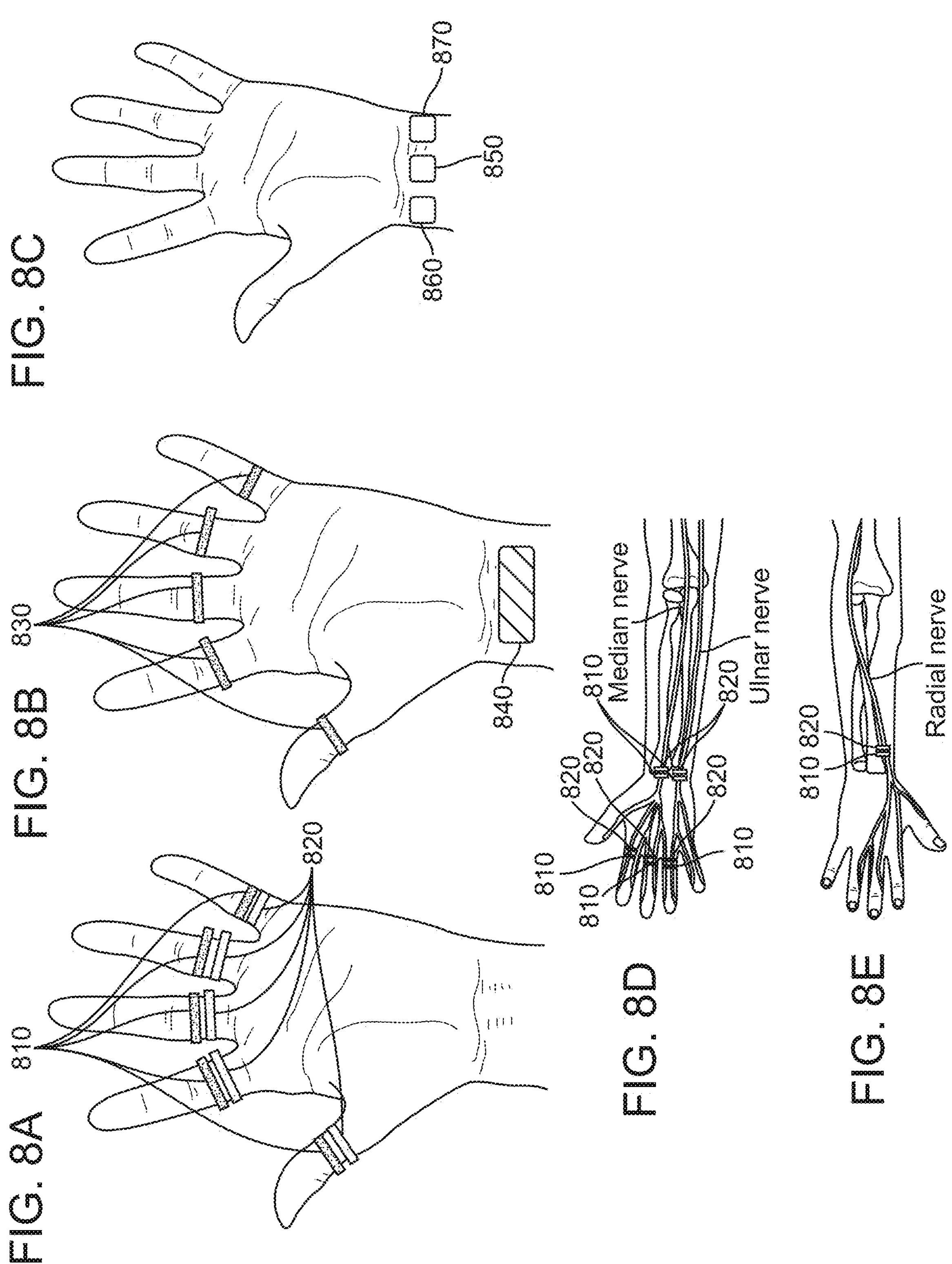
FIG. 8A illustrates an embodiment of an electrode pair used to excite nerves in different fingers, in which both electrodes are positioned on the finger.
FIG. 8B illustrates an alternative means of exciting nerves in different fingers, in which the second electrode is positioned at the wrist.
FIG. 8C illustrates an embodiment of the placement of electrodes on the wrist to target different underlying nerves.
FIGS. 8D and 8E illustrate various stimulation sites.

The device disclosed herein offers several advantages over high-frequency TENS stimulation, including using lower power (leading to extended battery life, less discomfort from motor recruitment and contraction, less discomfort from sensory excitation), less suppression of firing in activity in adjacent nerves (by depletion or other mechanisms), and maintaining longer-lasting effects such that the device only need be used intermittently to train or maintain training of the neural circuit dynamics. The device stimulates sets of nerves in such a way that it targets neural subpopulations to reduce synchronization of the population. For example, this may be achieved by stimulating different fingers on the hand. FIG. 8A is a diagram showing a preferred embodiment of the device, in which (810) anode and (820) cathode electrode pairs on the fingers are used to excite the branches of the proprioceptive nerves (the median, radial and ulnar nerves) in each finger. This arrangement of anode (distal) and cathode (proximal) is designed to induce a nerve pulse traveling towards the brain. The unique stimulation pattern on each finger will send a unique signal to a specific subpopulation of neurons in the brain because of the somatotopic organization of the brain, in which signals from different adjacent or nearby body parts synapse at nearby locations in the brain. In an alternative embodiment, the anode and cathode position may be reversed to inhibit the passage of sensory impulses towards the brain (antidromic collision). FIG. 8B shows an alternate arrangement, in which there is only a (830) single electrode on the finger and the (840) second electrode is positioned on the wrist. It will be appreciated by one skilled in the art that the fingers represent only one possible set of targets and different locations may similarly be used target adjacent subpopulations of neurons. In the alternative embodiment shown in FIG. 8C, the electrodes are positioned on different locations on the wrist to target the (850) median, (860) ulnar and (870) radian nerves. It will be appreciated by one skilled in the art that the input may also be positioned on other locations or branches of the nerves that input into the abnormal brain circuit. The location may be on the same or opposite side of the limb with tremors. The location may be on the surface of the skin, crossing the skin, or implanted. FIG. 8D illustrates various stimulation sites which can be subjected to stimulation that is delayed or offset by a predetermined fraction or multiple of the tremor period, T, as shown for example in FIG. 9.

Figures 9A, 9B:
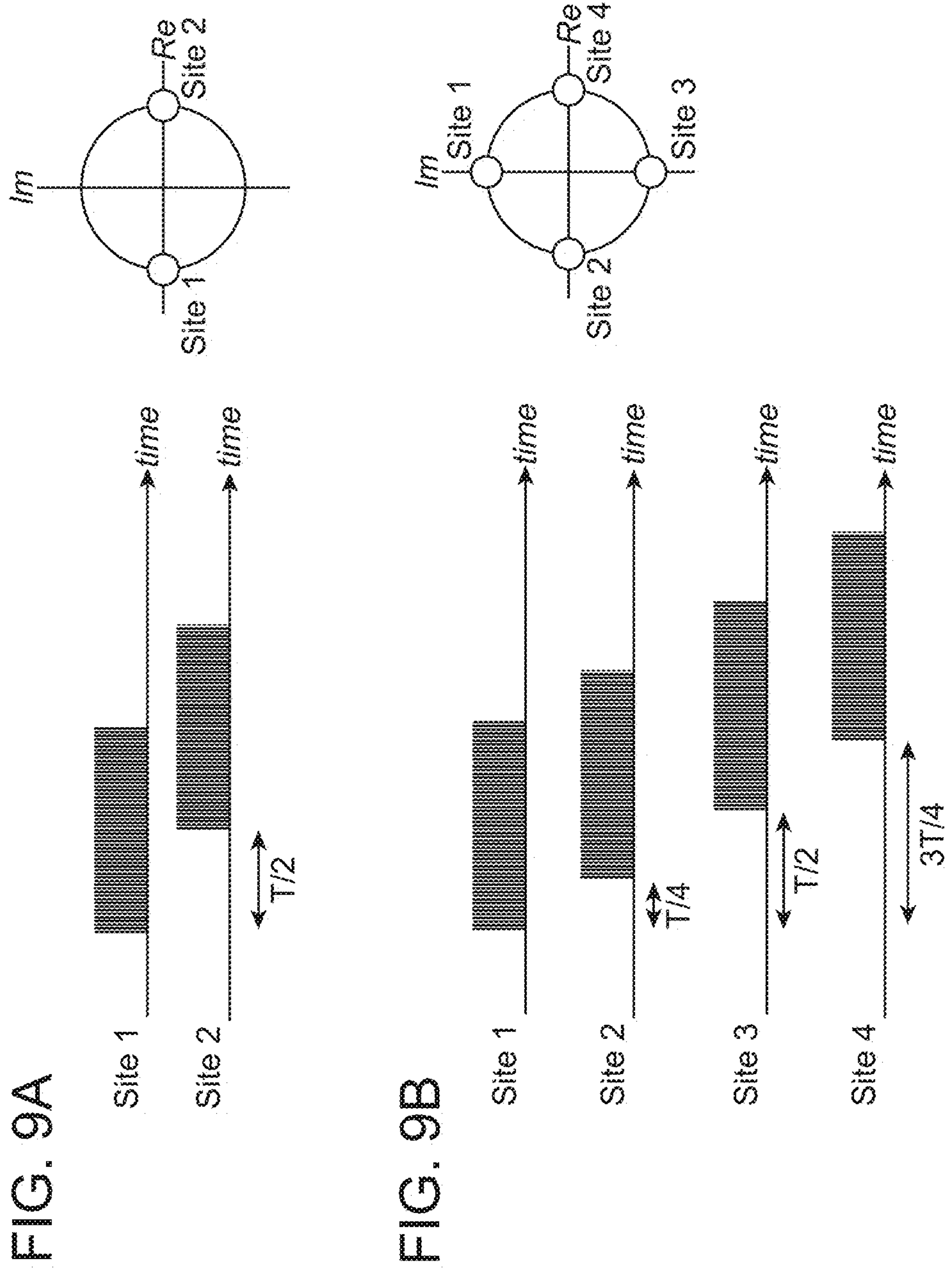
FIG. 9A is a diagram showing an embodiment of an excitation scheme to dephase the brain regions receiving sensory input from two fingers.
FIG. 9B is a diagram showing an embodiment of an excitation scheme to dephase the brain regions receiving sensory input from four fingers.

The device uses stimulation schemes designed to dephase, override or obscure the abnormal network. FIG. 9A is a conceptual diagram showing a sample excitation scheme to dephase brain regions receiving sensory input from two sites. For example, the two sites could be two of the fingers shown in FIGS. 8A-8D. The stimulation at site 2 is delayed after site 1 by time T/2, where T is the period of the native tremor. For example, if the tremor is at 8 Hz the period is 125 ms and the stimulation of site 2 would be delayed by 62.5 ms. The stimulation is designed to reset the phase of the neuron, which may be implemented using high frequency stimulation (above 100 Hz) or a DC pulse. FIG. 9B is a conceptual diagram showing a sample excitation scheme to dephase brain regions receiving sensory input from four sites, with subsequent sites delayed by T/4. In another embodiment, the stimulation at different locations is variable in parameters other than timing such as frequency or pulse width, or a combination of these. These variations are similarly designed to retrain the brain by dephasing, overriding or obscuring the abnormal network dynamics. In yet another embodiment, the stimulation may occur at a single location but vary in parameters over time. For example, it may vary in frequency every few seconds or turn on and off. In yet another embodiment, the stimulation is constant and at a single location. In preferred embodiments of these, the location is at the median nerve close to the wrist.

Optimizing Stimulation: Sub-Sensory

Stimulating at intensities below the sensory threshold will avoid the discomfort (tingling, numbness, pain) that can be associated with peripheral nerve stimulation. Because the exact electrode position, size and surface contact have a large effect on the stimulation level and the anatomical structures that receive the stimulation, the sensory threshold may needed to be calibrated for each patient and even for each session. This calibration may be done by the user manually setting the stimulation parameters or otherwise indicating their sensory threshold. Another possible mechanism is for the device to automatically sweep through a range of stimulation parameters and the patient chooses the most comfortable set of parameter values. Another possible mechanism is for the patient to choose from among a set of previously chosen parameter values that provided effective and comfortable stimulation. In some embodiments, the electrode pad can include a topical analgesic, such as Lidocaine, to reduce the discomfort from stimulation, thereby increasing the sensory threshold tolerated by the patient. In some embodiments, the topical analgesic can be delivered using a controlled release formation to provide pain relief for the duration the electrode pad is to be worn, which can be days, weeks or months. Such a method may provide more comfort or greater therapeutic effect, due to greater stimulation intensity and/or synergistic effects with the topical analgesic, which can reduce tremor in some patients.

Optimizing Stimulation: High Frequency

Alternatively or additionally, the stimulation waveform may be very high frequency, typically in the kHz and above, such that the stimulation is not felt by the user, or it is felt very little. Very high frequency stimulation is thought to make a conduction blockade. However, prior to the blockade there is an onset response including a strong depolarization of the nerve. To effectively implement very high frequency stimulation without causing discomfort for the patient, it would be preferable to eliminate this onset response. This can be done by cooling the nerve during the initial stimulation. Motor nerves are generally excited by stimulation at about 15 Hz and below, while sensory nerves are generally excited by stimulation at about 50 Hz and above. In some embodiments, it may be desirable to specifically stimulate above the 15 Hz threshold of motor neuron stimulation to avoid causing muscle contraction.

Optimizing Stimulation: Triggered

Alternatively or additionally, triggering the stimulation to the phase of the tremor can improve effectiveness. The goal of such stimulation is to break the rhythmic entrainment of motor units. More effective treatment may permit stimulating at lower levels to achieve similar therapeutic benefits with less discomfort. Essential tremor is essentially a problem of feedback in a resonant circuit. Stimulation timed off-phase from the tremor may reduce the tremor by altering the circuit dynamics, for example by shifting the gains on the feedback loop.

Figures 10A, 10B, 10C:
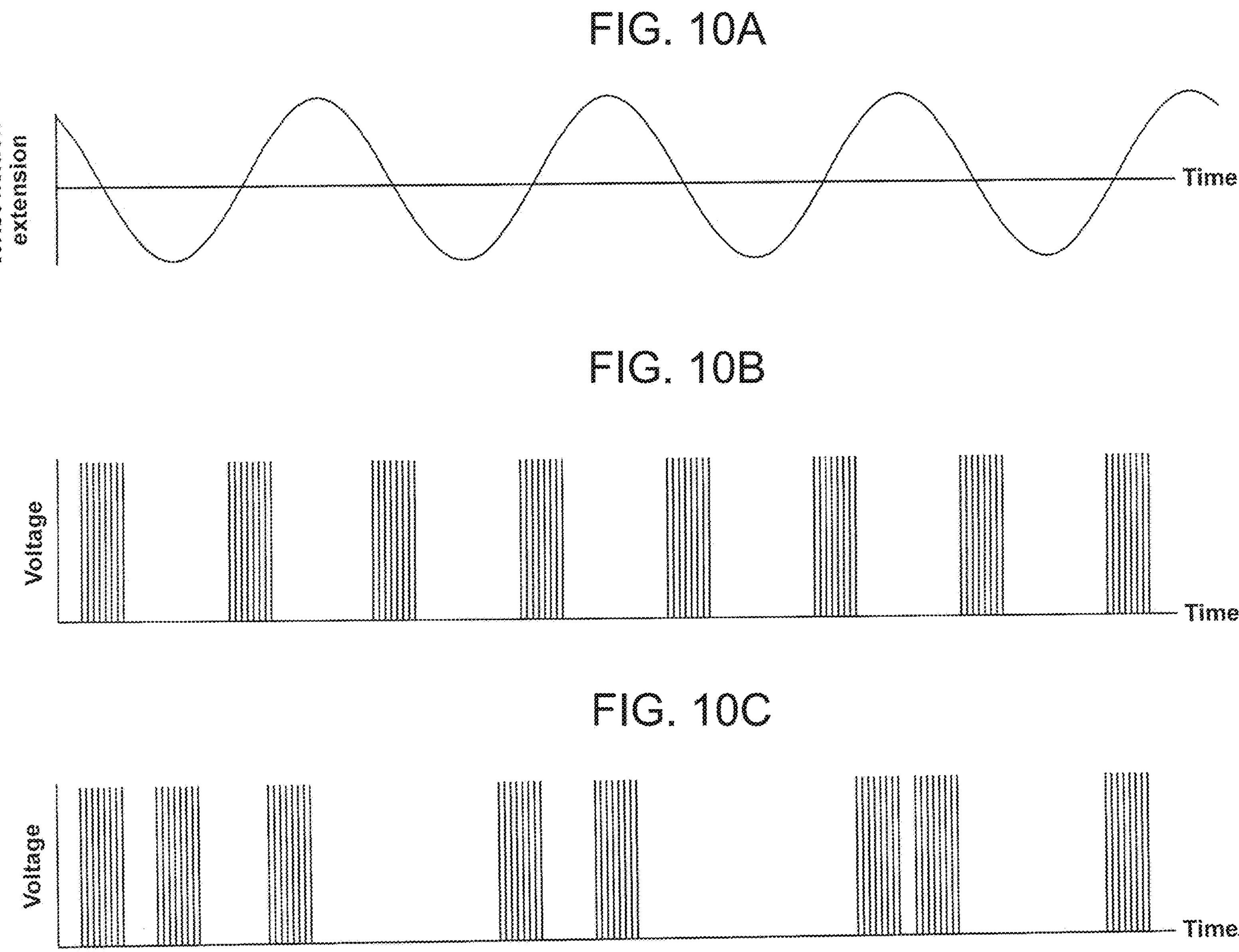
FIGS. 10A-10C illustrate an embodiment where the position of the hand may determine the optimal stimulation duty cycle and timing.

As shown in FIG. 10B, bursts of high-frequency stimulation may be timed to occur when the wrist is at its maximum flexion or extension (FIG. 10A). In example (FIG. 10C), the bursts have been shifted to a random phase. The position of the hand (FIG. 10A) may determine the optimal stimulation duty cycle and timing, such as (FIG. 10B) stimulating off-resonance with the maximum tremor deviation or (FIG. 10C) using bursts of variable temporal delays to avoid resonance with the tremor.

Figure 11:
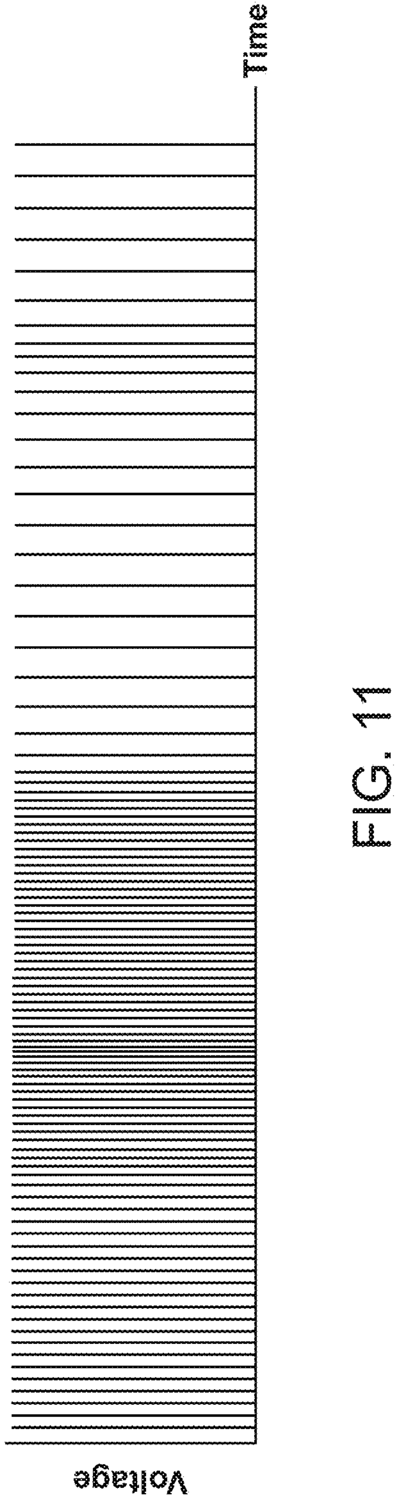
FIG. 11 illustrates an embodiment of variable stimulation that changes frequency over time.

Alternatively or additionally, the stimulation may be chaotic or variable. The goal of chaotic, random or variable stimulation is to prevent habituation and reduce resonance in the circuit. For example, this may be implemented by varying the stimulation frequency over time and/or by superimposing higher and lower frequency components, as illustrated in FIG. 11. [0159] Alternatively or additionally, the stimulation may be high frequency alternating current. This has been shown to block action potentials as they transmit along axons and could adjust circuit dynamics.

In some embodiments, the stimulation parameters as described above can be cycled according to a predetermined order to determine the optimal stimulation parameter. In some embodiments, the effectiveness of the stimulation parameters can be monitored over time to determine whether a particular set of stimulation parameters is losing effectiveness. In some embodiments, when the effectiveness of a particular set of stimulation parameters has been reduced by a predetermined amount, the stimulation parameters can be altered or cycled according to a predetermined order. For example, if stimulation is being triggered to the phase of the tremor, the stimulation can be delivered with random or variable temporal delays, or if the stimulation was using a set amplitude and/or frequency, the stimulation can be changed to a chaotic, random or variable modality to prevent or disrupt habituation. In some embodiments, the random or variable type stimulation parameters can be utilized according to a predetermined routine, such as daily for a predetermined number of hours, or weekly for a predetermined number of days, or at some other predetermined interval including time of day.

Effector: Vibrotactile Stimulation

The effector may be mechanical excitation of the proprioceptors by means including vibrotactile or haptic sensation. The mechanical stimulation might include force, vibration and/or motion. The effector induces action potentials in the target nerves by exciting the Golgi tendon organs (GTOs) or Pacinian corpuscles. Mechanical effectors can include, for example, small motors; piezoelectrics; one or more vibrotactile units comprised of a mass and an effector to move the mass such that a vibratory stimulus is applied to the body; an eccentric mass mounted on a shaft such that a vibratory stimulus is produced when the shaft is rotated; or an ultrasonic motor but can alternatively be a magnetorheological fluid (MRF) effector or electroactive polymer (EAP) effector.

The vibratory stimulus is optimally 250 Hz, corresponding to the optimal sensitivity of the Pacinian corpuscles (also known as lamellar corpuscles). The Pacinian corpuscles are the nerve endings in the skin that sense touch and vibration. Deformation of the corpuscle opens pressure-sensitive sodium ion channels to cause action potentials. Alternatively, the vibration may be below 50 Hz to excite the Meissner's corpuscles (also called tactile corpuscles) in the fingers that are sensitive to light touch.

This mechanical-type stimulator may function to reduce tremor through several methods. One method may be to transmit proprioceptive signals to the brain that obscure or modify the driving proprioceptive signal transmitted from the tremulous muscles. Another method may be impedance control. Joint impedance may altering co-contracting muscles through transcutaneous neurostimulation, affecting the stiffness of muscles and consequently muscle contractions. Another method may be the generation of compensatory muscle contractions, through neurostimulation, that oppose the tremulous contractions. The stimulator is preferably affixed firmly against the dermal surface, for example through an elastic or Velcro band.

Effectors: Chemical, Thermal & Other

The examples herein have primarily described the stimulation as electrical or vibrotactile. However, stimulation may alternately be achieved using other effectors that may offer significant benefit in terms of patient comfort, portability, safety or cost.

In another variation of the embodiment, the effector may be a neuromodulating chemical that either raises or lowers neurons firing thresholds. The chemical used in the invention may be a topical anesthetics including, but not limited to the "caine" family. The "caine" family of anesthetics may include but are not limited to benzocaine, bupivacaine, butacaine, carbisocaine, chloroprocaine, ciprocaine, dibucaine, etidocaine, heptacaine, levobupivacaine, lidocaine, lidocaine hydrochloride, mepivacaine, mesocaine, prilocaine, procaine, propanocaine, ropivacaine, and tetracaine. Other chemical families may include those of menthol family, or alpha-hydroxy sanshool from Szechuan peppercorn, or capsaicin, all of which are known to influence peripheral sensory nerves.

Figure 12:
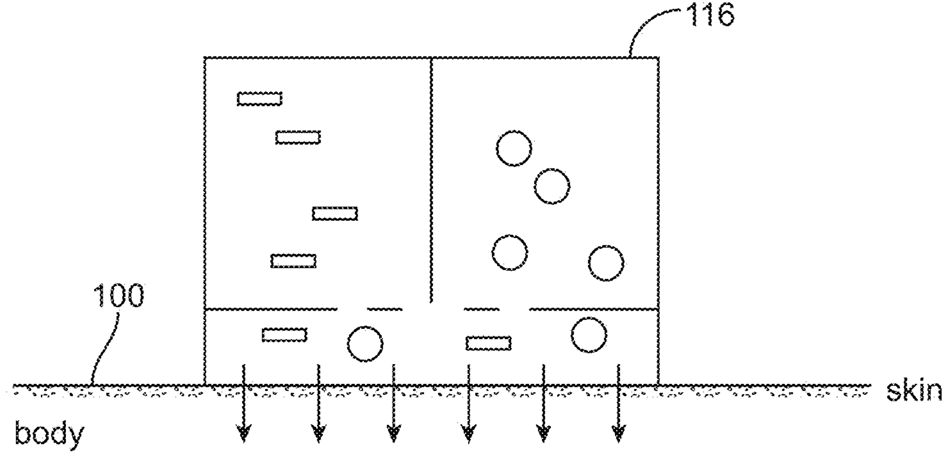
FIG. 12 is a drawing showing an embodiment where the stimulator is chemical and two neuromodulating chemicals can be mixed to provide tailored chemical stimulation.
Figures 13A, 13B:
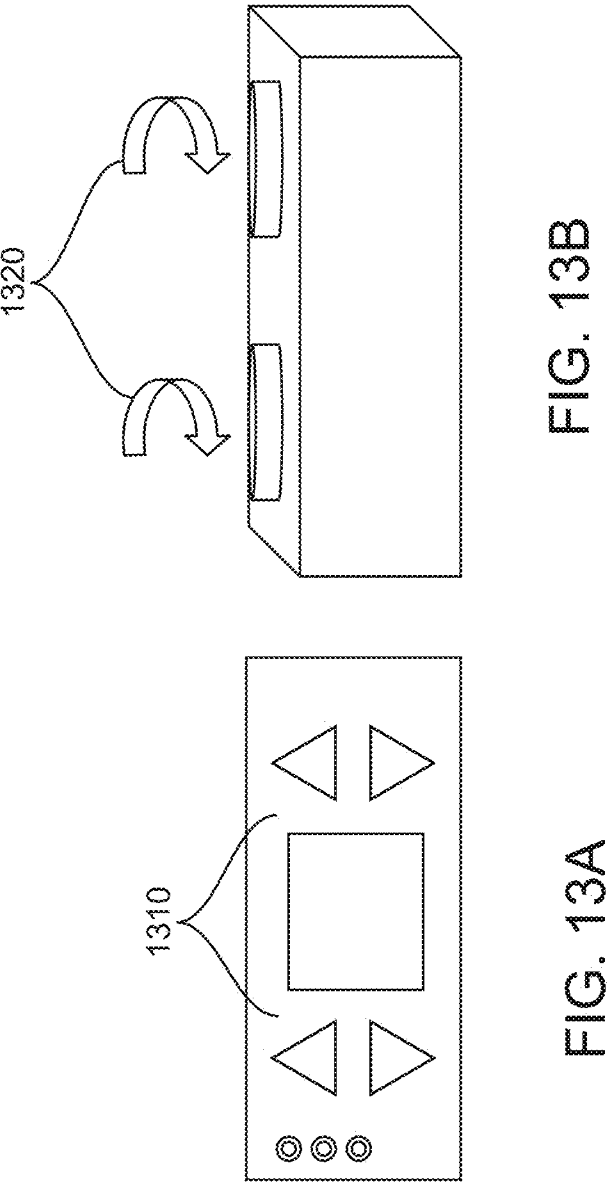
FIGS. 13A and 13B illustrate various forms of user controls.

FIG. 12 shows a chemical stimulator that may deliver chemical stimulus transdermally through a patch or could be delivered by microinjection. The preloaded protocols may preferably be predetermined compositions of the one or more chemicals. The topical anesthetics in this invention may be known for other indications and the recommended doses for simulation have been tested and approved for treatment of other indications. For example, the topical anesthetic lidocaine may be administered at 2-10% by weight. Alternatively, lidocaine may be administered in conjunction with other anesthetics. As seen in FIG. 12, the two neuromodulating chemicals are mixed to provide a tailored composition. The chemical stimulator may be administered as a composition comprising lidocaine 2.5% and prilocaine 2.5% by weight. Alternatively, the chemical stimulator could be administered as a composition comprising lidocaine 0.1-5% and prilocaine 0.1-5% by weight.

The chemical stimulator may be alpha hydroxy sanshool from Szechuan peppercorn. The alpha hydroxy sanshool may be contained in an excipient or carrier. The excipient may include gels, creams, oils, or other liquid. If the method of delivery is a transdermal patch, the formulation of the chemical agent may preferably be a cream or gel. The composition can be selected by the user through the control module 740 (of FIG. 7). If the method of delivery is microinjection, the formulation may preferably be a solution.

In some embodiments, the effector can be a temperature effector 732 (of FIG. 7) that induces cooling or heating. The effector may modulate neuronal firing by directly cooling the nerve or indirectly by cooling adjacent muscle, skin or other component of the arm. A temperature effector can include, for example, piezoelectrics (e.g. Peltier cooling tiles), circulating fluid, compressed expandable gas, cooled or warmed solid material or evaporative material. One example of a cooling effector can be as disclosed in U.S. Publication No. 2010/0107657, which is incorporated herein by reference. Heating or cooling may be applied as a patch that adheres to the dermal surface, by attachment to affix the stimulator to the dermal surface, such as an armband, or by an implant.

In an embodiment with a thermal stimulator, the preloaded protocols may preferably be predetermined temperatures of stimulation and associated durations of stimulation. Preferably, a preloaded protocol may call for thermal cooling for the duration of 15 minutes and cooling temperatures in the range of 15-25° C. The duration of stimulation may be preprogrammed to (but is not limited to) approximately 5 minutes to 30 minutes. The maximum length of stimulation should be well tolerated by the user and not cause any muscular or neurological damage. Temperature sensors may function to detect the effective cooling temperature in an embodiment where the stimulator is a thermal stimulator. Effective cooling or heating temperature may be the temperature felt by the user, and this is not necessarily the same as the applied temperature. If the temperature sensors determine that the effective temperature reaches a threshold, which may range from 5 degrees C. greater or less than the applied temperature for a particular protocol, the processor 797 (from FIG. 7) may modify said protocol to cool or heat more than originally programmed to compensate for the discrepancy between effective and intended cooling.

The invention may alternatively apply other effectors including acoustic (using ultrasonic excitation for exciting sensory nerves at the fingertips), vibratory, tactile, luminescent (e.g. light exposure in optogenetically modified nerves), magneticically (e.g. by rapidly switching RF fields) or a combination of mechanisms.

Form Factors: General Wearable Stimulator

Referring to FIG. 14A-E, the system 700 from FIG. 7 can be non-invasive, fully implantable, or partially implantable. For example, a non-invasive embodiment can include a non-invasive housing such as a sleeve 1400, or a patch 1410, or a glove. In such non-invasive embodiments, the interface of the housing is in communication with an external part of the patient. In some embodiments, one or more of the system components can be implanted 1420. For example, an effector and/or at least a portion of the housing interface can be implanted in the patient at a point of contact while the power source is external to the patient.

A non-invasive system housing can facilitate in maintaining the interface and/or effector in close proximity to the patient. The sleeve can cover a long stretch of arm or be a narrow band. The sleeve can cover at least a portion of the circumference of any part of a limb or the sleeve may cover the full circumference of any part of the limb. The function of the sleeve may be to maintain the position of the external device relative to the implant. The purpose of maintaining the position may include achieving good power transfer, reliable communication or other purposes.

The housing may be made of any material suitable to achieve the desired properties. For example, the housing material may be flexible and/or stretchable material, polymer or fabric. The housing can include fasteners such as Velcro, laces, toggles and/or ties to secure the device to the patient. The housing can include multiple layers and/or pockets configured to hold various components of the system as disclosed herein.

The system may be positioned by the patient with or without the assistance of a caregiver. In some embodiments, the system may have assistive mechanisms to position it on the arm, such as pressure-responsive snaps and/or self-aligning magnets. In some embodiments, such as sleeve 1400, the system may be slipped on (similar to a sports sleeve) over the end of a limb or wrapped around the arm or self-wrapped around the arm (similar to a snap-band). In some embodiments, the housing may be in the form of a patch 1410. For example, a housing patch 1410 can be secured to the patient's skin using a removable or degradable adhesive. The patch may be worn for a variety of times, including but not limited to patches worn only during the period of stimulation and patches left in place for several days, weeks, or months. The patch may also be attached mechanically, chemically, or electrically. Such embodiments include but are not limited to staples, strings, or magnets that secure the patch in a desired place.

Figures 14A, 14B, 14C, 14D, 14E, 14F, 14G, 14H, 14I, 14J, 14K, 14L, 14M:
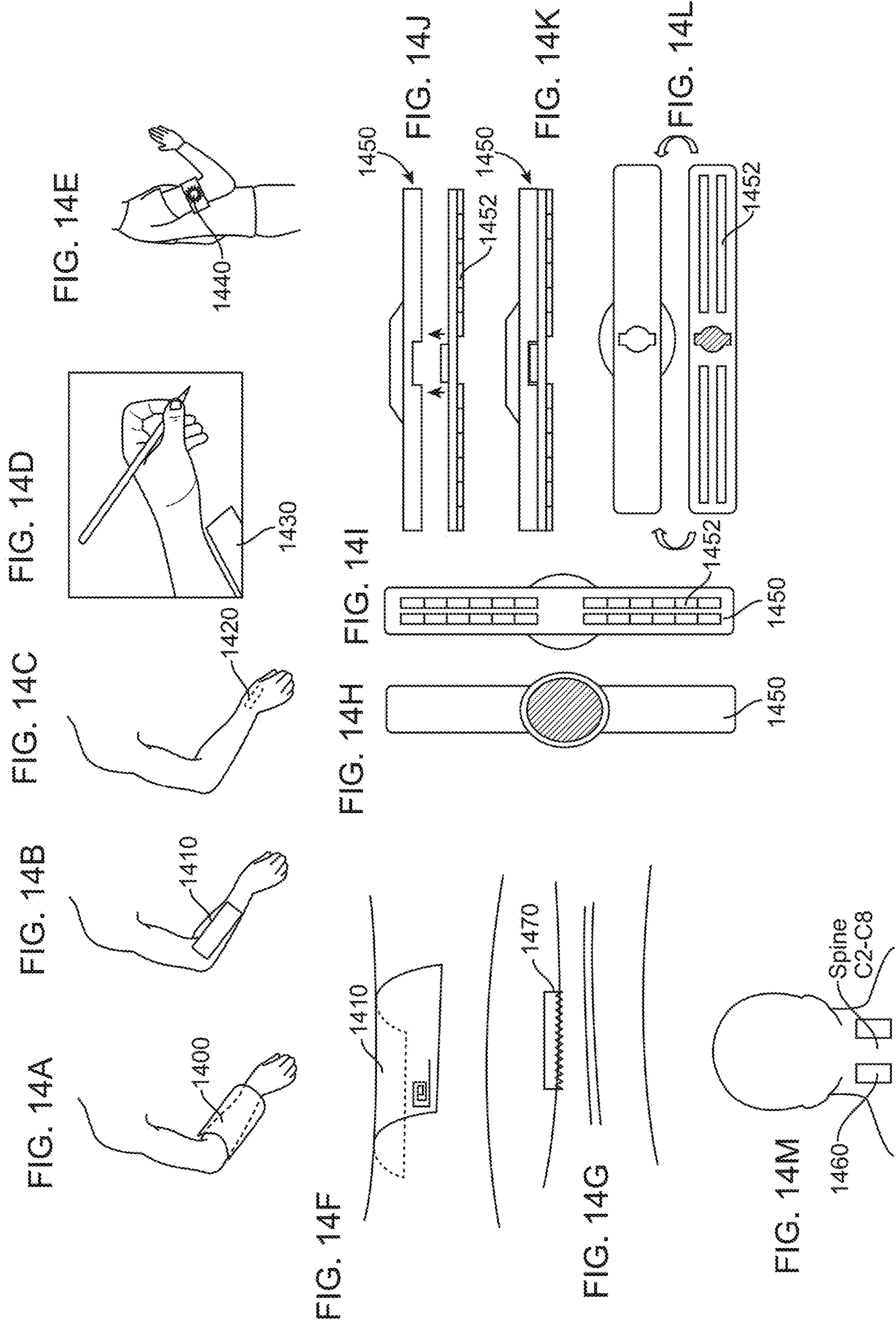
FIGS. 14A-14M illustrate various non-invasive or invasive embodiments of the tremor altering system.

In some embodiments, the non-invasive system can include an interface, which is in communication with the patient, but where the housing is not attached to the patient. For example, the system can be an external device with which the patient interacts. For example, the housing might be an open or closed tube-like structure in which the patient can place a limb. As illustrated in FIG. 14D, another example includes an external device that resembles a pad 1430 or support structure, such as a wrist pad or support, over which a patient can place at least a portion of a limb.

In one embodiment, the housing 1450 may have the configuration of a wristwatch as shown in FIG. 14H-L worn on the wrist or arm of the user. The housing 1450 may contain an interface 1452 separated, partially separated, or connected to the housing, and which may interact with the user. The interface 1452 may connect to the housing 1450 and be disposable after use for a period of time. The electrodes 1454 of the interface may be arranged in strips and may be arranged in anode/cathode pairs. Other electrode configurations as described herein may also be used. The period of time may be after a single use, or after multiple uses over the period of minutes, hours, days, weeks, or months. The interface itself may be the entire portion that is the wristband or may be a portion of the wristband or be attached to the wristband. The wristband itself can be part of the interface or be part of the housing, or both. In one example, the wristband with or without the interface may snap around the wrist, by including a feature of elastic material that is slightly curved so that when moved, the wristband wraps into a circular shape around the wrist. In another example, there is a temperature sensitive material, like nitinol, that has shape memory, so that when the device comes into contact with skin, the wristband with or without the interface may change shape to wrap around the patient's wrist. In another example, the wristband with or without the interface has one or more metal wires inside or outside the wristband that retains a new shape when moved to allow the user to place the device on the wrist and add force to shape the wristband onto the user's unique anatomy. In another example, the wristband with or without the interface wraps partially or completely around the wrist. This wrap may be in the same axis, or may be a spiral wrap.

The disposable or non-disposable interface may be connected to the housing in a number of different ways, including but not limited to snapping features, velco, pressfit, magnets, temperature, adhesive, that may or may not include self aligning features. The connection may be in one or more multiple dimensions or axes. As an example, FIG. 14J 14L show one potential embodiment where there is a self aligning piece, that can be a magnet, that connects the interface to the body in 3 dimensions. The circular shape of the aligning piece may allow the first dimensional alignment in one plane. The bar shape portion of the aligning piece, which can be offset from the circular feature of the aligning piece, may align the interface in the proper axis. The overall shape of the aligning piece can align the interface in the final dimension, which in this particular example of embodiment is the depth. The housing can have a matching feature of this shape for which the connection can connect to. It is possible that the connection feature can be reversed and the aligning piece be placed on the housing, and the matching feature of shape be placed on the interface. These connections of the aligning piece can possibly have or not have magnets on one, both or none of the housing or interface components.

Alternatively, the external device may be an object not worn on the body. For example, it may have the form factor of a cellphone and the patient would carry the device around in their pocket, bag, hand or other ways that cellphones are transported and supported, such as on a tabletop. It may be designed to sit on a furniture surface in the location where the patient wants their tremor controlled, such as at the dining room table, in the kitchen, or in their dressing room.

As shown in FIG. 14M, another preferred embodiment of the invention may comprise a stimulation device with one or more electrodes 1460 applied along the spine. The stimulation device may function to stimulate the release of neurotransmitters and reduce tremor through neuromodulation of the nerves located along the spine. Stimulation may affect the release and uptake of neurotransmitters, thereby affecting the nerves innervating the tremulous regions. The electrodes are preferably placed on the dermal surface at the cervical spine roots, preferably from C1 to C8 but most preferably between C5 and C8. The electrodes are preferably patch electrodes. The operating unit is preferably affixable to the user and the leads connecting the electrodes to the operating unit are preferably magnetized for easy connection. The operating unit may be connected to and controlled by the processor. Since the electrodes are preferably placed along the spine (back side of the user), a detached and portable controls module may be more convenient for a user to operate.

In one embodiment the electrodes may be placed on either side of the spine around C2 to C8 region of the neck and shoulders. The electrodes may be placed approximately 100 cm to 1 cm away from the spine, and may be placed 200 cm to 5 cm apart from each other. The stimulation parameters may include a phase duration of between 500 and 30 μseconds, which may preferably be 300-60 μseconds (micro-seconds). The pulse rate may range from 10 Hz to 5000 Hz, and the preferable range may be 50 Hz to 200 Hz, or 150 Hz. The cycle time may be continuous, or may range from 5 seconds to 1 hour. The preferable cycle time may be approximately 5 seconds to 20 seconds, or 10 seconds. The duration of electrical stimulation may range from 5 minutes to 24 hours per day. The preferable range may include 30 minutes to 60 minutes repeated approximately 10 times per day, or the preferable range may be approximately 40 minutes to 1 hours per day and repeated once per week to once every day. The amplitude (which may be used interchangeably with intensity) may range from 0.1 mA to 200 mA, and a preferable range may include 1 mA to 10 mA. The length of time the user may use the device before having an effect on the user's tremor may be one day to one month, or may preferably range from 2 days to 4 days.

Form Factors: For Electrical Stimulation

Conventional TENS devices are often difficult to position, bulky and uncomfortable. The innovations below are solutions to make it easy to quickly apply, adjust a simulator to control ET and to enable patients to use it discretely and comfortably.

With a conventional TENS device, it is difficult to properly size and position the sticker electrodes to optimally target the desired nerve. Smaller electrodes increase the current density at the target nerve, but with smaller pads it is more likely they will miss the nerve, and higher current density from smaller electrodes can cause discomfort. Larger pads are easier to position, but need more power and are more likely to unintentionally stimulate adjacent tissues. The following innovations resolve these challenges and achieve consistent, effective, comfortable, and safe stimulation.

Figure 15A:
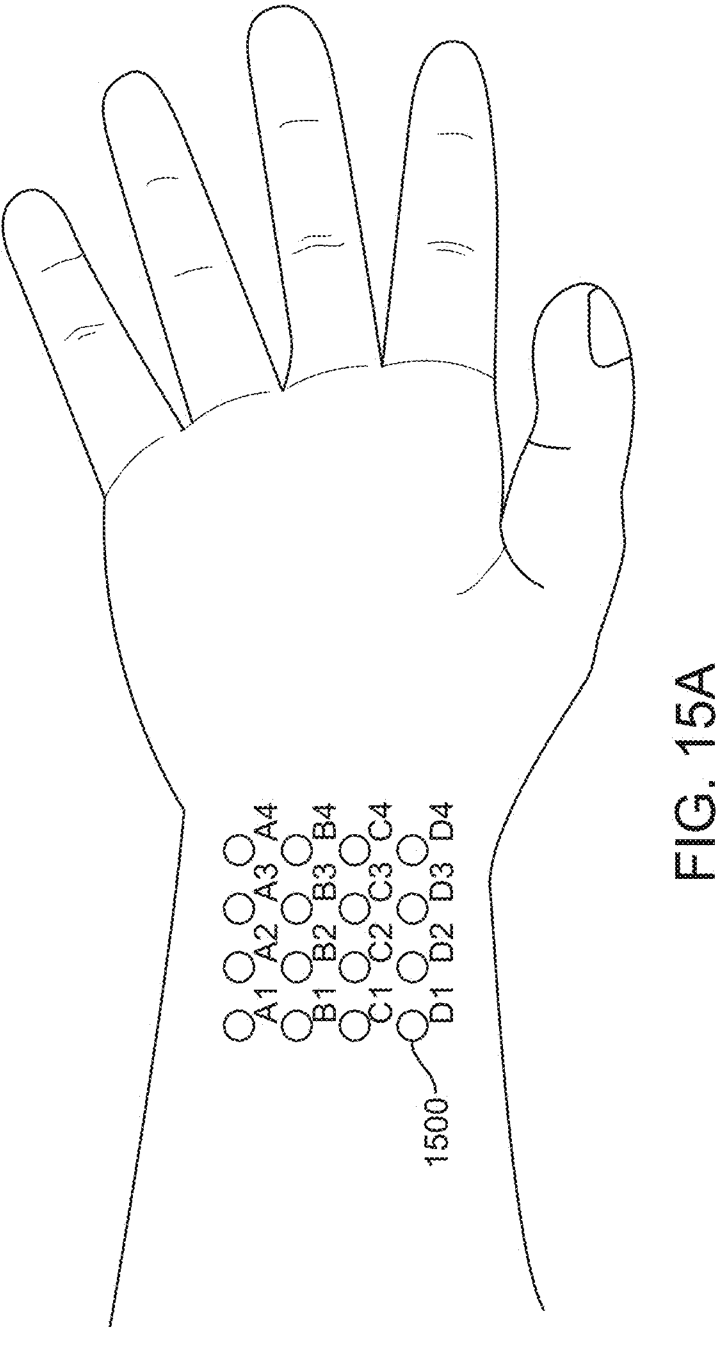
FIGS. 15A-15C illustrate various embodiments of an array of electrodes.
Figure 15B:
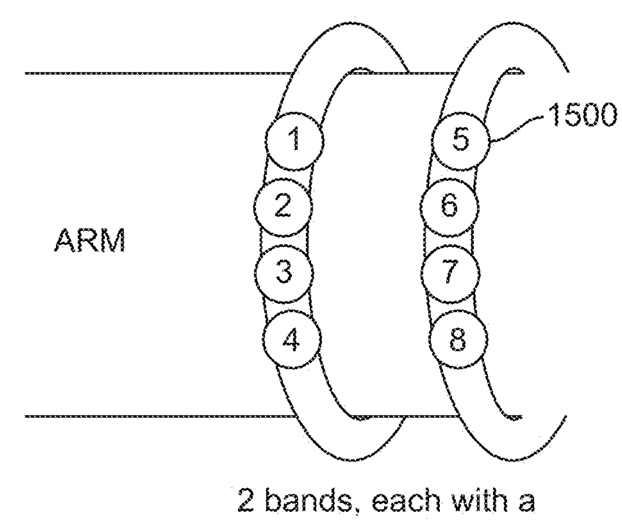
Figure 15C:
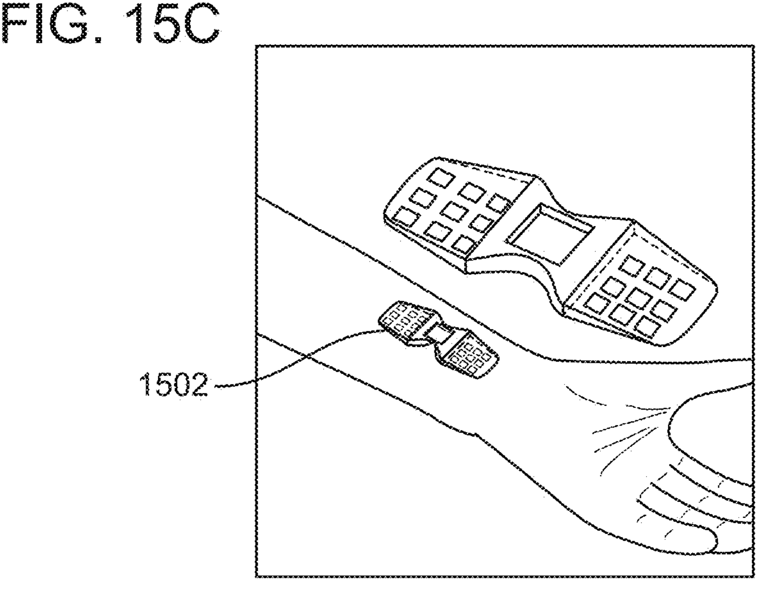
Figures 16A, 16B, 16C, 16D:
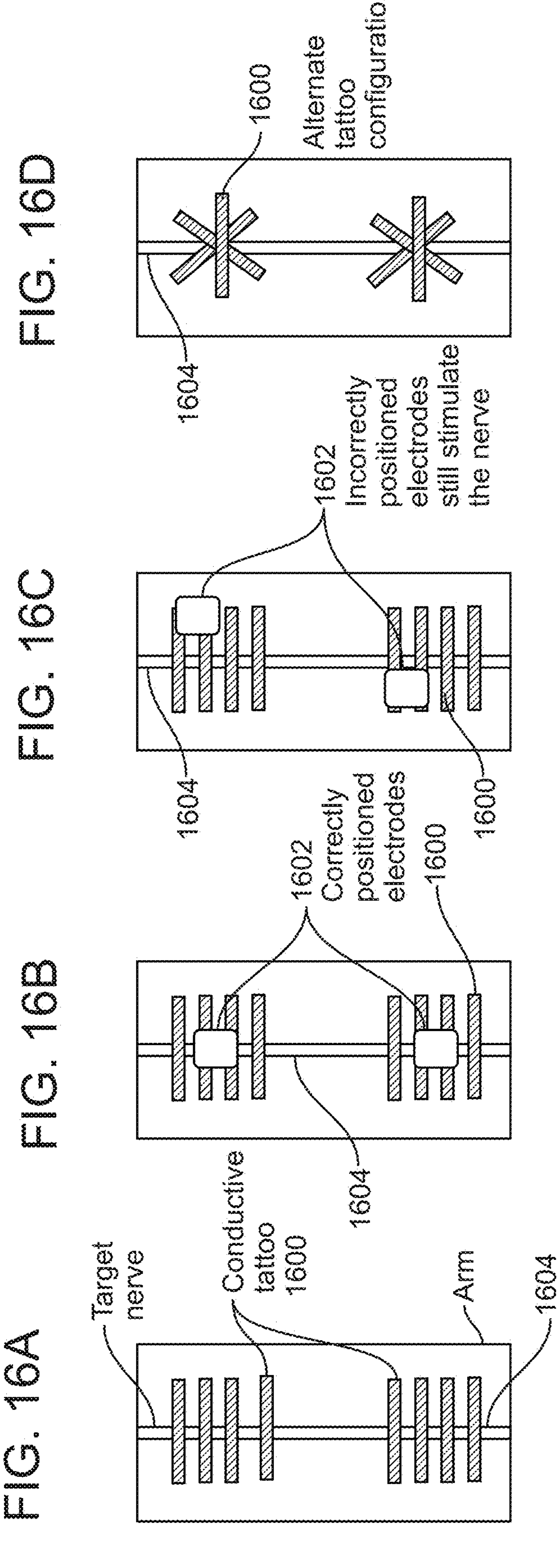
FIG. 16A-16D illustrate various embodiments of conductive ink tattoos.

Instead of using only a single electrode as the cathode and a single electrode as the anode, the device may contain an array of electrodes 1500, as illustrated in FIG. 15A-15C. Although the electrodes are shown individually on the patient's skin for the sake of clarity, in practice the array of electrodes can be integrated into a sleeve, flexible pad or substrate, or other form factor as described herein. An appropriate combination of electrodes would be selected each time the device is repositioned or based off the detected stimulation needs. The stimulation may use single electrodes as the anode and cathode, or may use a combination of electrodes to shape the simulation field. The electrode selection may be automatic based on feedback from sensors in the device (see below). Alternatively, the electrode selection may be done manually by the user. For example, the user may cycle through the electrode combinations until they find the combination that provides optimal tremor reduction or achieves a surrogate for the correct placement such as tingling in the 1$^{st}$ (index) and 2$^{nd}$ finger as occurs with median nerve sensory stimulation. FIG. 15A illustrates a two dimensional array of discrete electrodes 1500. Alternatively, some of the electrodes can be combined into linear rows, such that the two dimensional array is formed from a plurality of rows of electrodes. FIG. 15B illustrates a linear array of electrodes 1500 which can be worn as bands, as shown, or patches, pads, sleeves, and the like. FIG. 15C illustrates a housing 1502 that can be used to hold the array of electrodes 1500.

Alternatively, electrical stimulation from a poorly positioned electrode may be redirected to the target nerve by modifying the conduction pathway between the electrode and the target nerve. For example, a conduction pathway enhancer 1600, which can be made from a conductive material, can be placed on the patient's skin, embedded into the skin, implanted, or a combination of the above, in order to enhance the conduction of the electrical stimulus from the electrode 1602 to the target nerve 1604, as illustrated in FIGS. 16A-16D. The conduction pathway enhancer may be placed over the nerve and/or across the nerve. For example, in one embodiments, a tattoo of conductive ink may direct off-target stimulation towards the median nerve. A tattoo more conductive than adjacent structures (i.e. blood vessels, nerves) will provide the path of least resistance and redirect the current. To place or position the conductive tattoo, the target nerve is first positively identified. Then the conductive tattoo is placed over the target nerve. As illustrated in FIGS.

16A-16D, the conductive tattoo may include a plurality of conductive stripes that cross the nerve. In some embodiments, the stripes can be parallel to each other and cross the nerve transversely. In other embodiments, the stripes can be formed into a star or cross hatch pattern with a center located over the nerve. In other embodiments, a stripe can also be placed over and parallel to the nerve (not shown).

For user adoption, a wearable device should be discrete and comfortable. In the preferred embodiment shown in FIGS. 14B and 14F, for example, the effector is electrical and the skin patch has a single electrode or plurality of electrodes electronics printed onto a flexible substrate in a predetermined pattern to make a "second-skin", similar to a bandaid. For optimal comfort and surface adhesion, the mechanical characteristics such as the elasticity and stiffness should be matched to the skin. The circuitry and wiring for surface electrical stimulation may be printed or etched into a flexible material such that the device conforms to the body or to tissue within the body. For example, it may be copper printed on a flexible substrate such as plastic.

In another embodiment as illustrated in FIG. 14G, the device may be positioned on the surface of the body but containing a transcutaneous penetrating elements 1470 to improve influence on the nerves. These elements may be microneedles, used for improvement of stimulation and/or drug delivery. In some embodiments, the transcutaneous penetrating elements can form a microelectrode array that is placed on the skin surface and penetrates through the skin. The microelectrode array can function like microneedles, and can both improve signal transmission from the electrode to the nerve and to improve the permeability of the skin to improve topical drug delivery.

Sensors: Types of Sensors

Figures 17A, 17B:
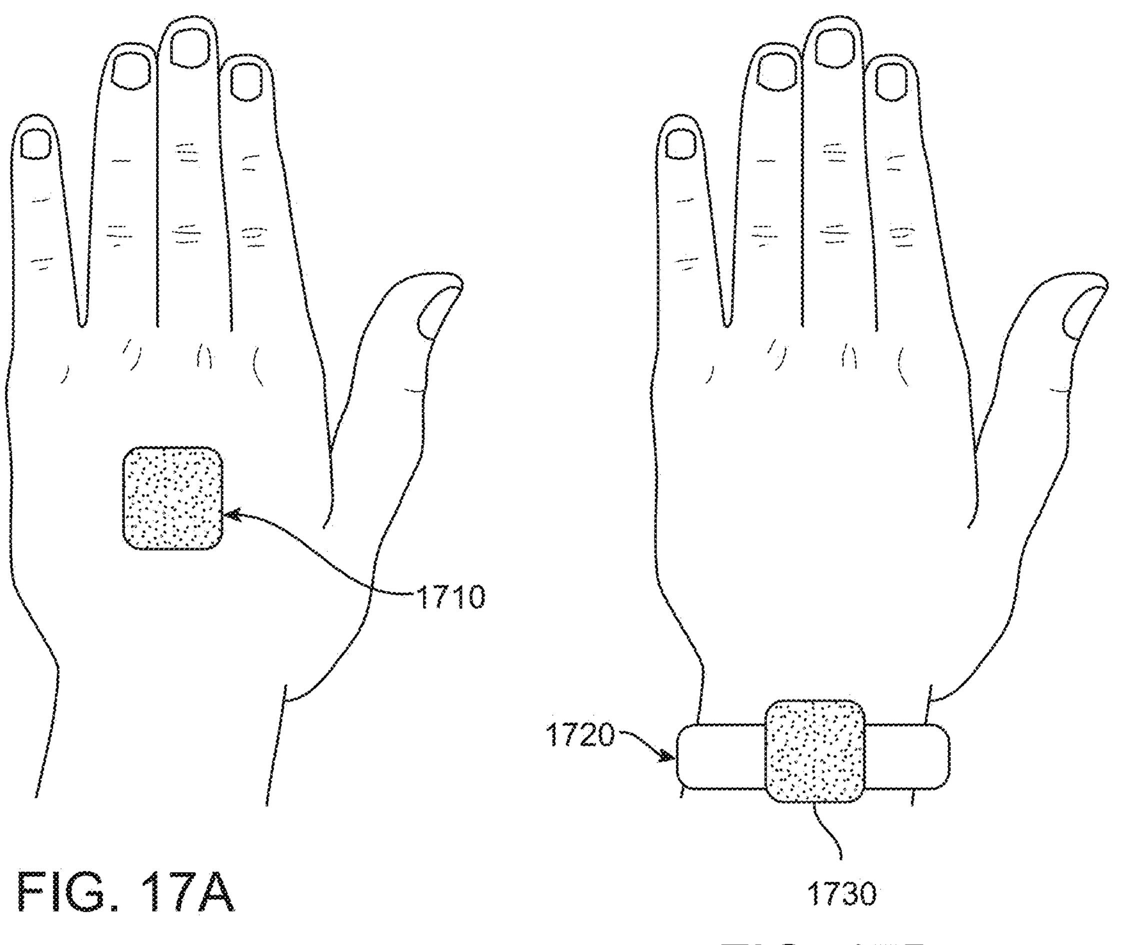
FIGS. 17A-17B is a diagram showing an embodiment of the positioning of an accelerometer on the hand or wrist for measuring the patient's activity and tremor.

The device or system may include sensors. Sensors for monitoring the tremor may include a combination of single or multi-axis accelerometers, gyroscopes, inclinometers (to measure and correct for changes in the gravity field resulting from slow changes in the device's orientation), magnetometers; fiber optic electrogoniometers, optical tracking or electromagnetic tracking; electromyography (EMG) to detect firing of tremoring muscle; electroneurogram (ENG) signals; cortical recordings by techniques such as electroencephalography (EEG) or direct nerve recordings on an implant in close proximity to the nerve. FIGS. 17A-17B show representative positions of motion sensors on the (1710) hand or (1720) wrist. Other tracking locations may include the fingers or other body parts.

The data from these tremor sensors is used measure the patient's current and historical tremor characteristics such as the amplitude, frequency and phase. These sensors may also be used to determine activities, such as to distinguish involuntary movements (e.g. tremor) from voluntary movements (e.g. drinking, writing) or the presence and absence of the tremor relative to the time of day or other detected activities such as sleep/wake cycles.

The device may also include sensors to provide performance and usage data, including when the device was worn (e.g. from temperature sensors), the device's location (e.g. from GPS), battery level, or video recording. In another embodiment, the sensor is a temperature sensor to measure the temperature of a cooled limb. In another embodiment, the sensor includes video recording. In another embodiment, sensors from existing hardware such as a smartphone are used. For example, the tremor may be measured using the accelerometers on a smartphone or engaging the patient in a tremor-inducing writing task by analyzing a line traced on a smartphone screen.

Sensors: Algorithms To Extract Tremors

Algorithms will be used to extract information about tremors from the stream of data provided by the sensors. The tremor may be identified based off its time-domain signal, frequency-domain signal, amplitude, or firing pattern (e.g. bursts, spikes). For example, in FIG. 18A-18B, the frequency analysis of the spectral power of gyroscopic motion data indicates that the tremor is centered at approximately 6.5 Hz (see the maximum power in the lower plot).

Motion data can be taken as each raw sensor channel or by fusing the raw signals of multiple sensors. As one example, multi-axis accelerometer data can be combined into a single numerical value for analysis. The algorithm will extract motion data in the 4 to 12 Hz range to remove motions that are not attributable to the tremor. This may be done using any combination of notch filters, low pass filters, weighted-frequency Fourier linear combiners, or wavelet filters. As each patient has a dominant tremor frequency, this range may be narrowed based on specific knowledge of the patient's tremor or tremor history. For example, for a patient with a 6 Hz tremor an analysis algorithm may extract only motion data in the 5 to 7 Hz range. Alternatively, if a patient is known to have a tremor that flexes and extends the wrist by a maximum of 5-degrees then an analysis algorithm would determine that a measured motion of 45-degree wrist flexion is likely due to intentional gross movement rather than tremor. Alternatively, the algorithm will sample the motion data by identifying time periods likely to correspond to postural holds or kinetic fine motor tasks.

Once the appropriate motion data has been extracted, the algorithm will analyze key characteristics of the tremor including the amplitude, center frequency, frequency spread, amplitude, phase, and spectral power.

Sensor fusion techniques can also be used to analyze different aspects of the tremor. For example, a multi-axis accelerometer and gyroscope attached to the backside of the hand could be combined to reduce noise and drift and determine an accurate orientation of the hand in space. If a second pair of multi-axis accelerometer and gyroscope were also used on the wrist, the joint angle and position of the wrist could be determined during the tremor. This could isolate what excitations of which nerves are causing damping of the different muscle groups controlling the tremor.

ET patients have two components of their tremor. Kinetic tremors are present during intentional movement and have a major impact on quality of life because they impact a person's ability to accomplish daily tasks like drinking, eating writing and dressing. Postural tremors are present during static positions held against gravity. They can be embarrassing, though are less impactful on quality of life. Postural tremors typically present earlier in the disease course and are thought to drive kinetic tremors. Both components are typically in the range of 4 to 12 Hz, with older patients experiencing lower frequency tremors.

Detecting postural and kinetic tremors is more challenging than detecting resting tremors. Resting tremors are present in other movement disorders including Parkinson's disease and can be easily identified by analyzing tremors present only while the limb is at rest. Extracting kinetic tremors from motion data is challenging because it is necessary to separate the motion due to tremor from the motion due to the task.

Figure 19:
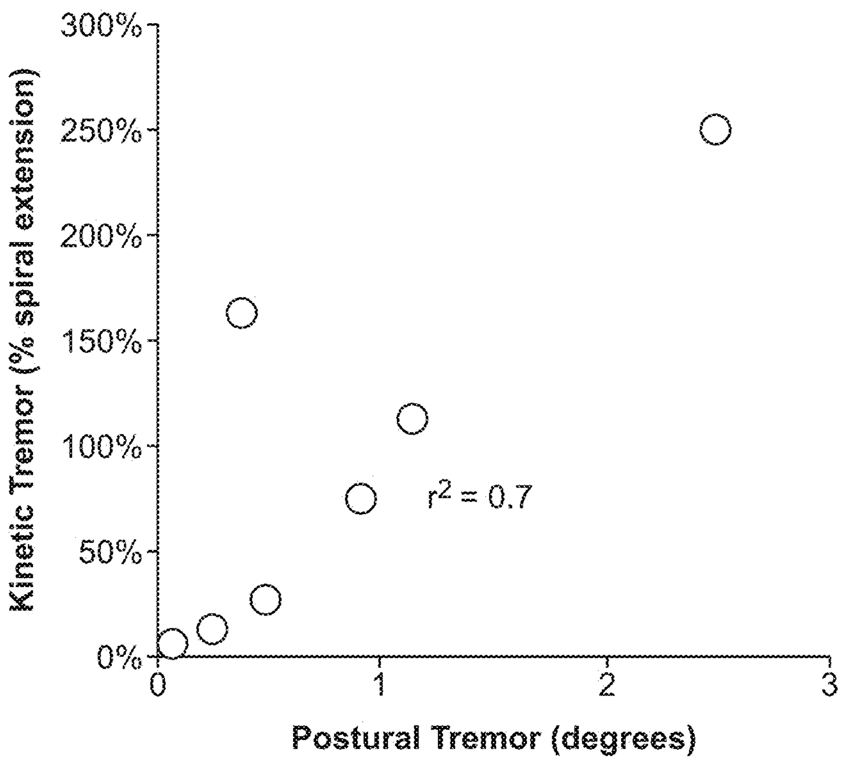
FIG. 19 illustrates the correlation of postural tremor with kinetic tremor.

Identifying postural tremors may be easier than kinetic tremors since accelerometer/gyroscopic data during kinetic tasks are corrupted by the motion involved in the task. It is thought that postural tremors may drive the kinetic tremors because people often have postural tremors earlier in life than kinetic tremors and they are about the same frequency. The correlation of postural and kinetic tremors we discovered in our clinical study, as illustrated in FIG. 19, supports this theory of using postural tremor data to analyze or treat kinetic tremors.

Sensors: Data Storage & Usage

Figure 20:
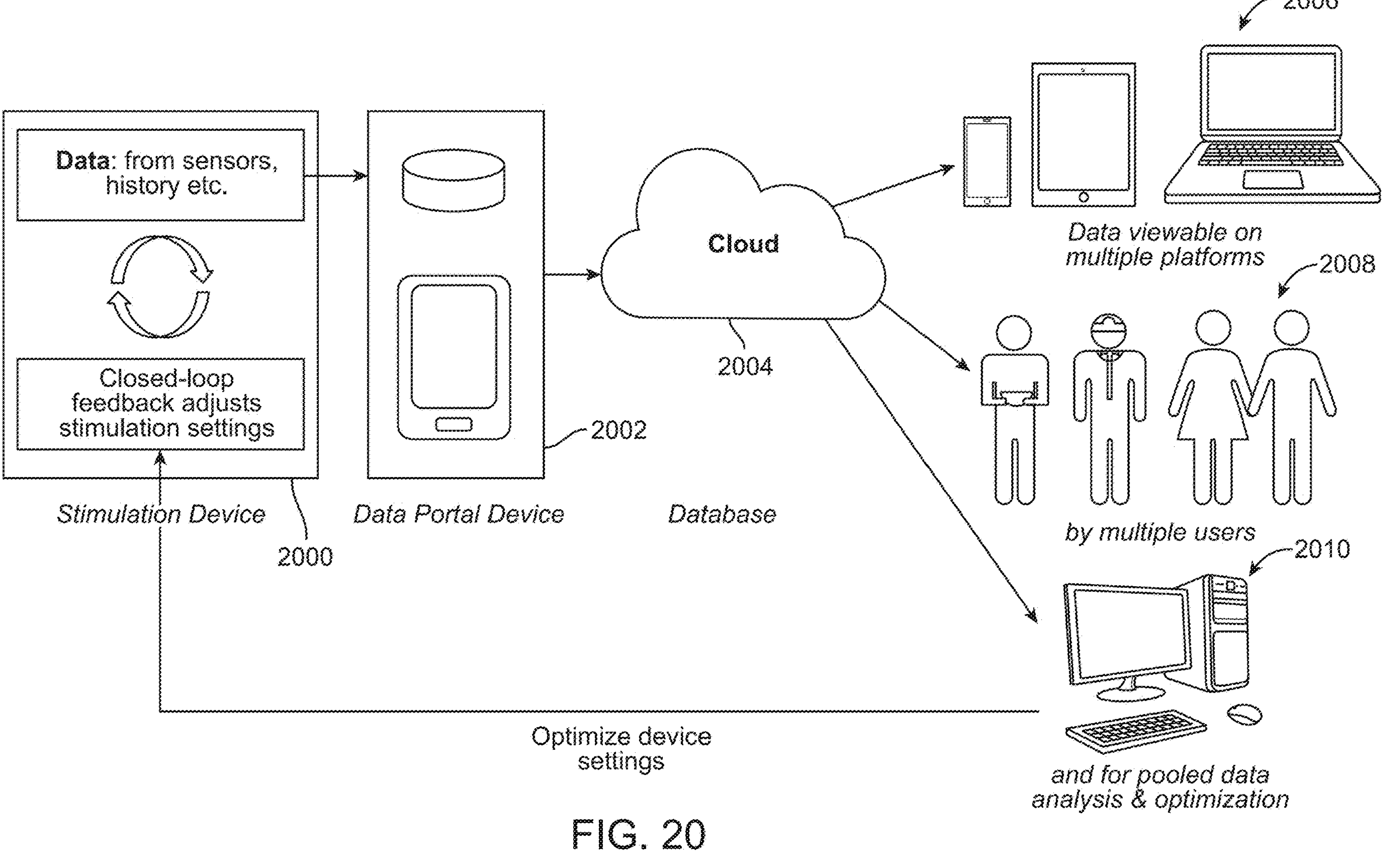
FIG. 20 illustrates an embodiment of a stimulation device that can record and transmit data, such as the tremor characteristics and stimulation history, to a data portal device, such as a smartphone, that transmits the data to a cloud-based server.

As shown in FIG. 20, the stimulation device 2000 can contain hardware, software and firmware to record and transmit data such as the tremor characteristics, stimulation history, performance, usage and/or control of the device to a data portal device 2002, such as a smartphone, cell phone, tablet computer, laptop computer, desktop computer or other electronic device using a wireless communication protocol, such as Bluetooth.

Data recorded using the device used the ET patients can be stored on a smartphone that transmits it to a cloud-based database/server 2004, or the device used by the ET patients may directly transmit data to a cloud-based database/server 2004, enabling many activities including tracking tremors, optimizing stimulation, sharing with caregivers and physicians, and building community. The data may provide information to the controller, real-time feedback to the patient, caregivers and/or clinicians, or may store the data to provide historical data to the patient, caregivers and clinicians. The data stored on the cloud 2004 can be viewed on multiple platforms 2006 by multiple users 2008. In addition, the data on the cloud 2004 can be pooled and analyzed by a computing device 2010.

Patients are generally monitored for tremor every few months, or perhaps annually, when they visit their physician. This monitoring is typically highly subjective. Further, tremor severity can be dramatically affected by many factors, including sleep patterns, emotional status, previous physical activity, caffeine intake, food, medications etc.

Such infrequent and inaccurate monitoring limits the ability of patients, their caregivers and physicians to understand the severity and progression of a patient's ET and the effects of various treatments and behaviors. These factors can interact with the effects of the stimulation provided by the device, and it can be difficult to detect these interactions. These interactions could be identified to optimize the therapy and help patients better understand how their behavior affects their tremor.

In one embodiment shown in FIG. 21A, the tremor is 2100 monitored using sensors that may be IMUs, electrodes, or any of the other sensors previously discussed. The monitoring may be continuous or during discrete time periods. The data from these sensors is 2110 analyzed to identify changes in the tremor characteristics (amplitude, frequency etc.) over time. The results are recorded and 2120 displayed to the user. The 2110 analysis and/or 2120 display may be done on the stimulation device itself or by communicating either the raw or analyzed data to a secondary device such as a smartphone or computer.

In another embodiment, 2101 behavioral data may also be collected such that the analysis may examine the relationship between the tremor history and the user's behaviors. Behavioral data may include consumption of caffeine, alcohol, medications and anxiety levels. The system can then alert the patient of the interactions between the behaviors and the tremor.

In another embodiment in which the device is therapeutic (i.e. if it has an effector), the 2102 stimulation history may be collected such that the analysis may examine the relationship between the stimulation history and the tremor characteristics.

The embodiment shown in FIG. 21B adds a 2140 upload to the cloud. The order of 2140 upload and 2110 analysis may be swapped such that the analysis is done on-board prior to upload (not shown). Use of the cloud enables the results to be 2120 displayed to the user on a variety of networked devices including smartphone, tablets, laptops and desktop computers; to other users such as 2150 physicians or caregivers; or for 2160 pooled analysis across multiple patients.

FIG. 21C shows some of the potential uses of the pooled data, including 2170 connecting patients to similar patients based on features such as their tremor characteristics, geography, age and gender or 2180 improving the stimulation algorithms.

FIG. 21D shows how the data monitoring and analysis shown in FIGS. 21A-C may be used in a closed loop to adjust the stimulation parameters. In this way, the algorithms detect interactions between the variables to optimize the therapy.

Figure 26A:
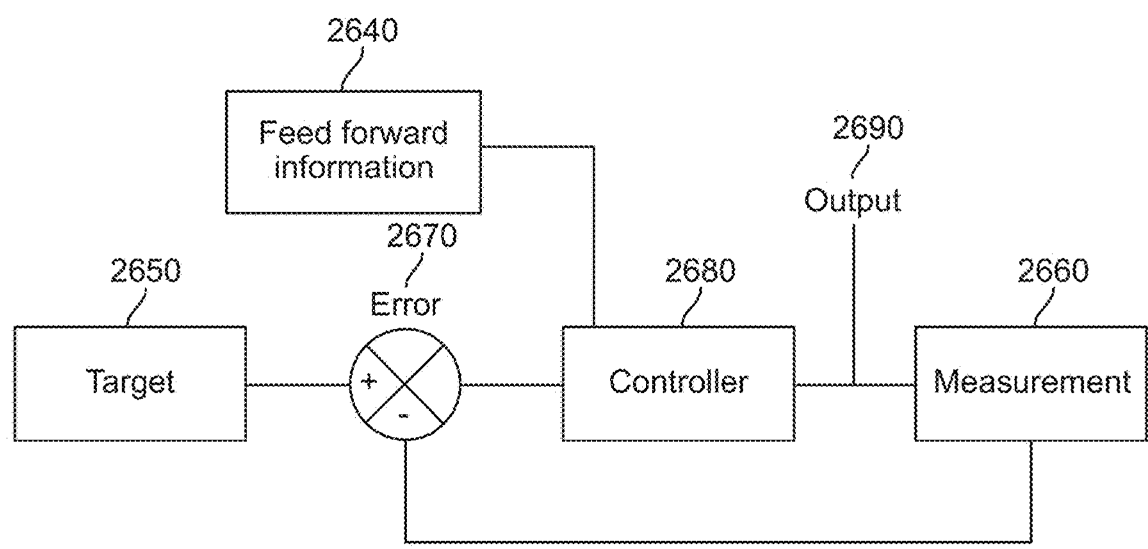
FIGS. 26A-26B illustrate two preferred embodiments of the controls module that is used to interact with the device. A control system for the tremor device utilizes feedback to modify the stimulation. It is a closed loop in which the stimulation is adjusted based on measurement of the activity and tremor.

The device may contain closed-loop control of the stimulation to adaptively respond to detected tremor or activity levels. The device enables sensation of tremor through an activity sensor, data logging and systematic adjustment of the stimulation parameters to achieve an optimal tremor reduction. FIG. 26A is a control diagram showing the basic components of this detection and response system. The (2650) target defines the intended profile. For example, in ET patient this profile may be absence of tremor and in a PD patient this profile may be absence of tremor or rigidity. The (2670) error between the (2650) target and (2660) detection is fed into the (2680) controller, which modifies the (2690) output. The (2680) controller may include a processor and memory. In addition to the error and measurements, the (2680) controller algorithms may also input the history of measurements, stimulation and activity into its algorithms. The output (2690) modifies the stimulation. If the effector is electrical, this may include modifying the waveform, frequency, phase, location and/or amplitude of the stimulation. In the preferred embodiment (FIG. 15), the device contains an array of small electrodes and the output modifies the selection of which electrodes to use as the anode and cathode. The effect of the modifications are then (2660) detected by the measurement device and the process repeats. The (2660) detection and/or (2690) output modification may occur continuously in real-time, with periodic delays between predefined times (e.g. hourly or daily), or in response to a user-generated signal such as a pre-defined sequence of movements or a button press. Alternatively, the controller may alert the patient to manually modify the stimulation parameters. This closed loop may be used for automatic self-calibration.

Figure 26B:
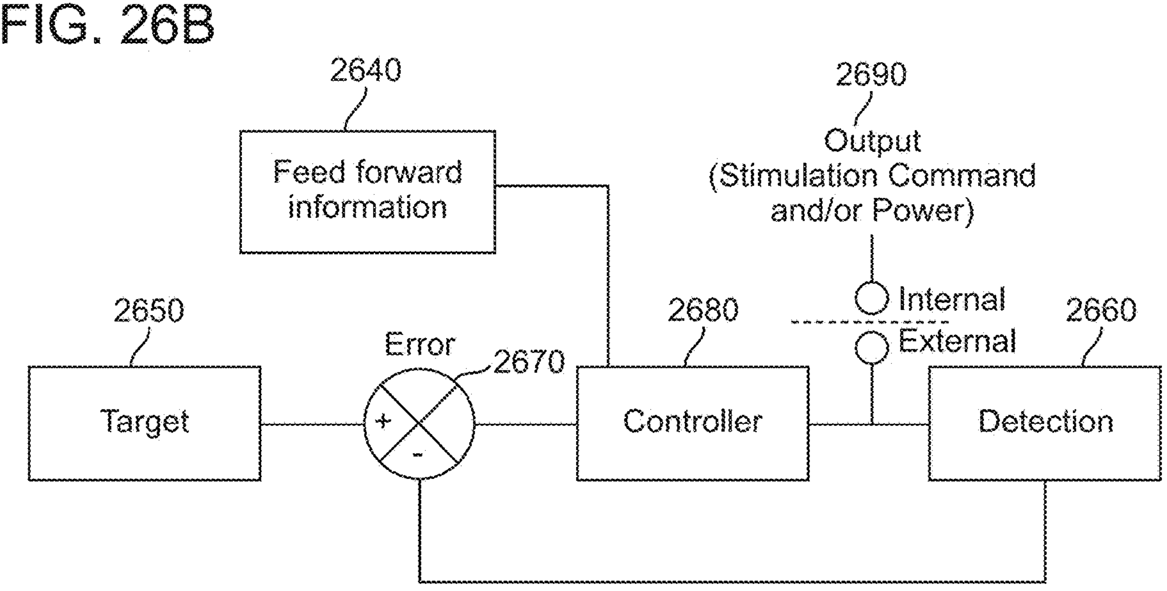

FIG. 26B illustrates a control diagram showing the basic components of this detection and response system, which is similar to the description shown in FIG. 26A, but now with internally and externally located components.

The control could also take into account other patterns in behavior, more like a feed-forward controller 2640. For example, typical patterns in eating times could cause the effector to fire more actively at particular times to reduce tremor for those activities. Also, the person could indicate in a schedule, based upon their activities for the day if they would like increased treatment at certain periods of time, for example if they had a speech or other anxiety causing events. This type of information could also be obtained and learned over time by the control unit. Other data such as sleep, food intake, particularly alcohol and caffeine consumption, exercise history, emotional status, particularly levels of anxiety, and medication usage collected through other mobile technologies and applications, such as Azumio, Jawbone, Fitbit, etc., which may be integrated into the cloud-based patient database, as illustrated in FIGS. 20 and 21. The user can be prompted to enter such data, such as taking a photo of a meal to determine food uptake using an imaging processing application. The database will combine discrete events (e.g., time and amount of caffeine intake) with time series data (e.g., tremor measurements). Algorithms will examine the relationship between patient behaviors, stimulation, and tremor. These will optimize stimulation and alert the patient of the behaviors that influence tremor. This will allow for individually optimized treatment for tremor and feed forward into the system.

In some embodiments, the user may be prompted at predetermined times by the device or cell phone to perform a specific task, which may be tailored to the type of tremor afflicting the patient, such as holding the arm out in a specific posture for ET, or placing the arm in a rest position for Parkinson's. During this time, the sensors can record the tremors. In some embodiments, the patient may additionally or alternatively be instructed to consume caffeine or to record the time period that has elapsed since they last consumed caffeine. This data may be used to determine how caffeine affects tremor, the efficacy of the treatment protocol and stimulation parameters, the duration of the effectiveness, and the like. In some embodiments, the patient can be prompted at a predetermined amount of time after stimulation, such as 10, 20, 30, and/or 60 minutes after stimulation. The time can be adjusted depending on measured duration of the tremor reduction following stimulation.

The device will have on-board data logging and may transmit this information to an external data portal device, such as a smartphone or internet-enabled charge & sync station. This transmission may be wireless or direct. The external device will have greater storage capacity and allow transmission to a database in the cloud. The external device may analyze this data on-board and present information on a screen or using indicators such as LED lights, or the data may be shown on the stimulation device itself.

The data in the cloud will be viewable on multiple platforms including smartphones, tablets and computers. The data will be viewable by multiple people including the user, his or her physicians, caregivers or family members. This will provide a much more comprehensive picture of a patient's tremor and enable optimization of treatment. In some embodiments, users viewing the data can also add comments and notes to the data, which can be tagged with the identity of the user making the comment or note, and the time the comment or note was made. In some embodiments, the ability to make annotations can be restricted to the health care providers, such as the patient's physician, and the patient.

In some embodiments, access to the data is restricted to the health care providers and the patient. Access can be limited by requiring users to set up a secure username and password to access the data. In some embodiments, the patient can also provide others, such as family and friends, with access to the data.

Algorithms for Optimization

Figure 22:
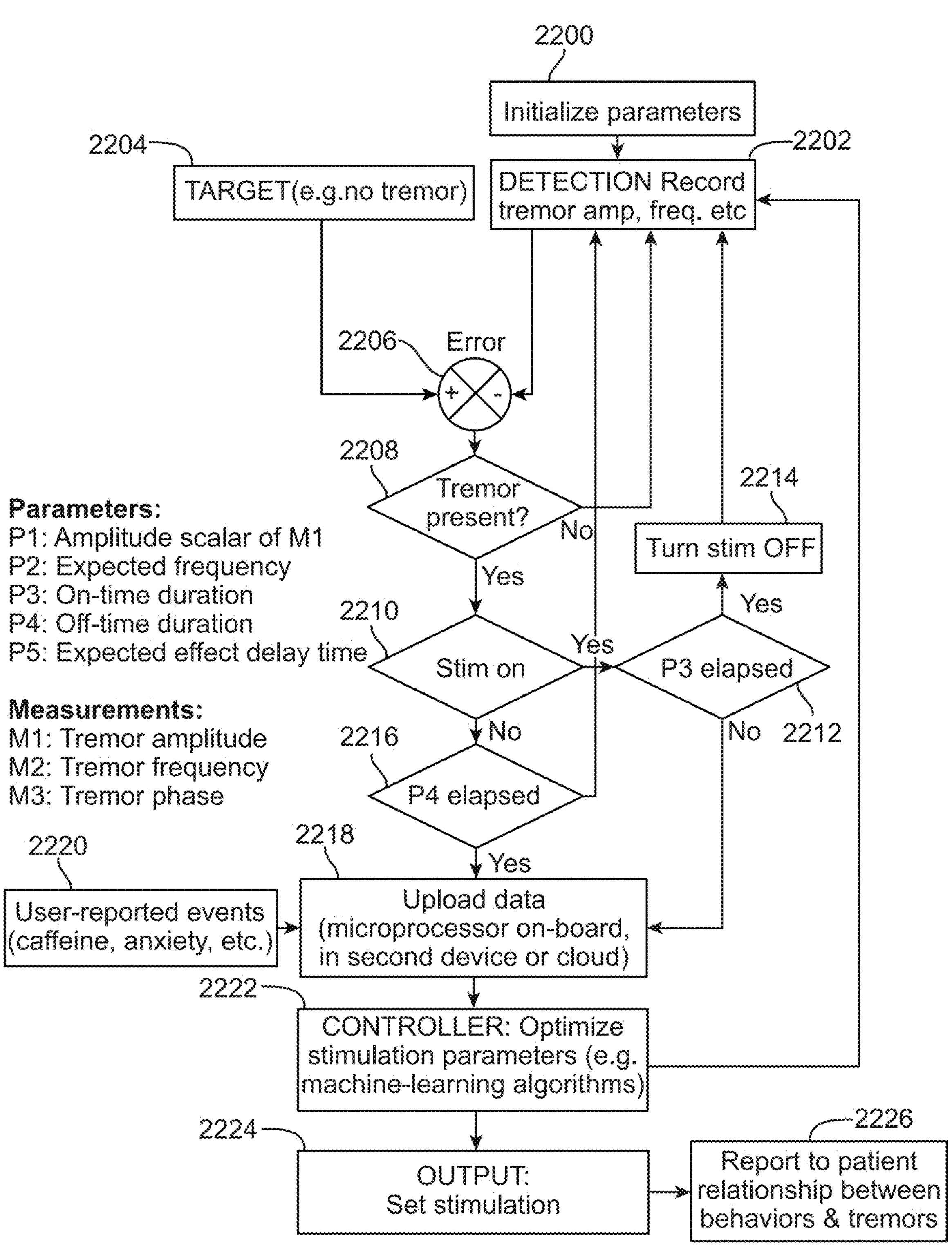
FIG. 22 is a flowchart showing the feedback logic.

Our data indicate that stimulation using a TENS device is highly effective in some patients, somewhat effective in other patients, and ineffective in others. However, optimization of the simulation parameters (simulation intensity, frequency, waveform, duty cycle, phasing etc.) enables the device to achieve the greatest tremor reduction with the most comfort in each patient and allows the device to adjust over time in response to changes in the circuit dynamics, device positioning, patient state, etc. FIG. 22 shows a decision algorithm/controller for device.

In one embodiment, the optimization algorithm starts by initializing one or more parameters 2200, which may include stimulus amplitude, expected frequency, on-time duration, off-time duration, and expected stimulation effect delay time. Next, a sensor detects 2202 and records tremor characteristics, including tremor amplitude, frequency, phase, and other characteristics described herein. The detected tremor characteristics 2202 are compared with desired target tremor characteristics 2204, which may be no tremor or a reduced tremor. The comparison step 2206 can determine the error or difference between the detected tremor characteristics and the target tremor characteristics, and determine whether tremor or reduced tremor is present 2208, or in other words, whether the detected tremor meets or exceeds the target conditions. If no tremor is detected, or more generally, if a predetermined target tremor condition is not exceeded, then the algorithm loops back to the detection step 2202. If a tremor is detected, or more generally, if a predetermined target tremor condition is exceeded, then stimulation can be turned on 2210. Once the stimulation has exceeded the set on-time duration 2212, then the stimulation is turned off 2214, and the algorithm proceeds back to the detection step 2202. While stimulation is on, the device can upload the recorded data 2218 to the cloud or another device for further processing. Once the stimulation has been turned off 2214, the algorithm can monitor the off-time duration 2216, and can continue to upload data 2218 once the off-time duration has elapsed. Alternatively, data can be uploaded even before the off-time has elapsed. User-reported events 2220, which can include caffeine or alcohol intake, feelings of anxiety, and other events that may affect tremor, can also be entered into the system and sent to the cloud. The data can be processed by a controller 2222 which can optimize the stimulation parameters using various algorithms, including machine learning algorithms. Once the parameters are optimized, the new stimulation parameters are set 2224. A report 2226 can also be sent to the patient that can highlight or correlate various behaviors identified in the user-reported events with measured tremors.

In one embodiment, the stimulation algorithm is designed to optimize the therapeutic "on"-time. The optimization algorithm may find the best solution for outputs including but not limited to controlling tremor during specific tasks, at specific times of day, in specific location or simply to optimize the overall daily minimization of tremor. The algorithm may be self-calibrating to adjust stimulation parameters including but not limited to the frequency, amplitude, pulse width, electrode selection for cathode and anode and/or timing of turning the stimulation on and off. The algorithm may respond user input or may be entirely preprogrammed. The algorithm may be a learning algorithm to tailor the stimulation over time to adjust in real-time to a patient's tremor or patient-defined needs. The stimulation may be triggered on or off in response to inputs including but not limited to user input (e.g. turning the device on or and off), timing since previous use, time of day, detection of tremor (e.g. by accelerometers), electrical recordings, or algorithms based on the previously described or other inputs. As an example, the user can use voice activation to turn the device off to utilize the therapeutic window (i.e., the time of tremor reduction after stimulation is turned off) to provide a time interval of steadiness needed for intentional movements. In another example, the user bites down or uses the tongue muscle detected by an external device placed inside or outside the oral cavity, which will signal to turn off the stimulation and allow the user steadiness of the arm to enable execution of intention actions with steadiness. In some embodiments, the system and algorithm can detect the type of tremor, such as differentiating between a postural tremor and kinetic tremor, based on an analysis of the tremor parameters and the measured activity of the patient. In some embodiments, the stimulation parameters may be determined in part based on the type of tremor detected.

In some embodiments, the system can be controlled by an event trigger. Event triggers can include defined movements, temperature, voice activation, GPS location, or based on data received by a sensor or any combination thereof. For example, the device can be turned on or off during an intentional movement, such as, before a tremor has started or ended respectively. In another example, the device is turned on or off when a specified temperature is reached. The system may act to achieve a desired tremor suppression profile. For example, the control may activate the device during a period of desired tremor suppression; prior to a period of desired tremor suppression, with effects lasting beyond the use of the device; and/or in response to detection of the tremor.

Optimization Based on Community Data

At present, the time course of tremors is poorly understood. While creating a database for a single patient will improve our ability to reduce tremor in that patient, combining individual patient data into a database that includes recordings from many patients enables more powerful statistical methods to be applied to identify optimal stimulation parameters. In some embodiments, data from patients suffering from the same type of tremor can be combined. In some embodiments, the tremor data from each patient can include searchable and sortable metadata that allow the collection of data in the database to be sorted, searched and/or reorganized on demand. The metadata can include type of tremor (tremor amplitude, tremor frequency, temporal presence of tremor etc.), name, age, race, sex, location, time, food and drink consumption (particularly for caffeine and alcohol), activity history (exercise, sleep etc.), medications, past treatments, and current treatments.

The systems described above with respect to FIGS. 20 and 21 can be adapted to data from many patients going into a database, and the algorithms can operate on the massive set of data.

Community Building

Individuals with ET feel isolated by the disability associated with their tremor. As a result, they are highly motivated to meet other people with ET. There is an active and growing set of support groups that organize meetings and enable patients with ET talk about their issues and discuss possible solutions. Attending these meetings can be challenging because some patients with ET have difficulty driving. Also, the individuals within a particular physical location who attend a support group may have symptoms that are different from each other, and they lack the ability to identify other patients that are most like each other.

Algorithms can help individuals find members of the ET community that have similar profiles. For example, algorithms can characterize patients based their age, tremor severity, tremor features, success with treatment, treatment type, medication type, location (based on address or GPS), and other characteristics. This will help them communicate with each other and to share information from the central community website that is customized to a particular individual with ET or a caregiver. For example, system can identify patients within a geographical location or identify other patients within a predetermined distance from a particular patient. Patients may have the option of joining an online ET community and making their location searchable on the system. The system may identify to a patient existing ET community support groups within a predetermined distance.

Other Processor, Library, Data Storage

The processor 797, as illustrated in FIGS. 7A-7D for example, may function to operate on data, perform computations, and control other components of the tremor reduction device. It may preferably be a microprocessor with peripherals or a microcontroller. For example, the processor could receive input from the user via the controls module 740 and could control the execution of stimulation as selected by the user. In another embodiment, the processor 797 could execute predefined stimulation protocols selected by the user. These stimulation protocols could be found in the digital library of stimulation protocols 798, which may be loaded in the processor 797 or stored in external memory, like an EEPROM, SD card, etc. The processor 797 can also receive information from the sensors 780 and process that information on board and adjust the stimulation accordingly. The selection of the processor is determined by the degree of signal processing it needs to do and the number and type of peripherals it needs to control. Communication with peripherals can be executed by any of the well-known standards such as USB, UART, SPI, I2C/TWI, for example. The processor may also communicate wirelessly with other device components using Bluetooth, Wifi, etc. The processor may be on board the device, or the tremor data be transmitted via a wireless link between the processing unit and the stimulation unit.

In an embodiment with an electrical stimulator 730, the preloaded protocols 798 may be electrical stimulation or a sequence of electrical stimulations. Electrical stimulation or electrical signal refers to an electrical pulse or pattern of electrical pulses. The electrical stimulation may include parameters such as pulse frequency, amplitude, phase, pulse width, or time duration of electrical stimulation. These parameters may be predefined or controlled by the user.

The data storage unit 770 may function to store operational statistics about the device and usage statistics about the device, preferably in NAND flash memory. NAND flash memory is a data storage device that is non-volatile, which does not require power to retain the stored information, and can be electrically erased and rewritten to. In some cases, it may be beneficial to have this memory be removeable in the form of a micro-SD card.

Power

The effector may be electrically coupled to one or more power sources, as illustrated in FIGS. 7A-7D for example.

The power source 750 functions to power the device. The power source 750 may be connected to the processor 797 and provide energy for the processor to run. The power source may preferably be rechargeable and detachable as this allows the device to be reused. The power source may preferably be a battery. Several different combinations of chemicals are commonly used, including lead acid, nickel cadmium (NiCd), nickel metal hydride (NiMH), lithium ion (Li-ion), and lithium ion polymer (Li-ion polymer). Methods of recharging the battery are preferably attaching to a wall socket or other powered device, solar power, radio frequency, and electrochemical. An alternative source of power is ultracapacitors. Ultracapacitors may be divided into three different families-double-layer capacitors, pseudocapacitors, and hybrid capacitors. Ultracapacitors may preferably be made with nanoporous material including activated charcoal, graphene, carbon nanotubes, carbide-derived carbons, carbon aerogel, solid activated carbon, tunable nanoporous carbon, and mineral-based carbon. Ultracapacitors provide an advantage of faster charging than batteries as well as tolerance of more charge and discharge cycles. Batteries and ultracapacitors could alternatively be used in conjunction as the tolerance of ultracapacitors to a large number of charge-discharge cycles makes them well suited for parallel connections with batteries and may improve battery performance in terms of power density. Alternatively, the power source may harness energy from the body. In some embodiments the power can be harnessed by kinetic motion, by thermal energy, and/or by sound. The power source may alternatively include a plug to an external source, such as a general appliance.

In one embodiment, a special charging station or dongle could be used to recharge the device. The benefit of the special charging station is that it could also facilitate the upload of data from the device to the web via Wifi or another communication protocol.

Implants

In some embodiments, at least a portion of the system is implantable. An implanted stimulator may offer greater control and comfort than surface stimulation because it is located closer to the nerve and avoids exciting cutaneous afferents.

The method of stimulating peripheral nerves to control hand tremors introduces specific requirements for an appropriate implanted stimulator. First, the implant should be small to minimize the invasiveness of the procedure used to position the implant and make it appropriate for implantation. Second, because the stimulation may be responsive to the detected tremor or user input, the implant should be capable of receiving communication from an external device. Third, the device should tolerate variability in the positioning of the external device.

Any number of the system components disclosed herein can be implanted. In some embodiments, the housing, interface, effector and power source are implanted and the controller is external to the patient. In such embodiments, the controller, may be, for example, in wireless communication with the effector. In other embodiments, the power source is external to the patient.

The device may be implanted subcutaneously, partially implanted, or may be transcutaneous (passing through the skin), may be on the surface of the skin or may not be in contact with the body. It may be an assembly of these devices, such as a surface component that communicates with or powers an implanted component. If it is implanted, the device may be implanted in or around nerves, muscle, bone, ligaments or other tissues.

In one embodiment, the implant is positioned in or near the carpal tunnel to influence the nerves passing through the carpal tunnel. In another embodiment, the implant is positioned on or near the median nerve in the upper arm between the biceps. In another embodiment, the implant is positioned on or near the median, radial or ulnar nerve in the forearm or wrist. In another embodiment, the implant is positioned on or near the brachial plexus to influence the proprioceptive nerves passing from the arm toward the central nervous system.

The implanted portions may be placed or delivered intravascularly to affect nerves in the area within range of the implant's effect. In one example, a device is placed in or through the subclavian artery or vein to affect the nerves of the brachial plexus.

Figure 23:
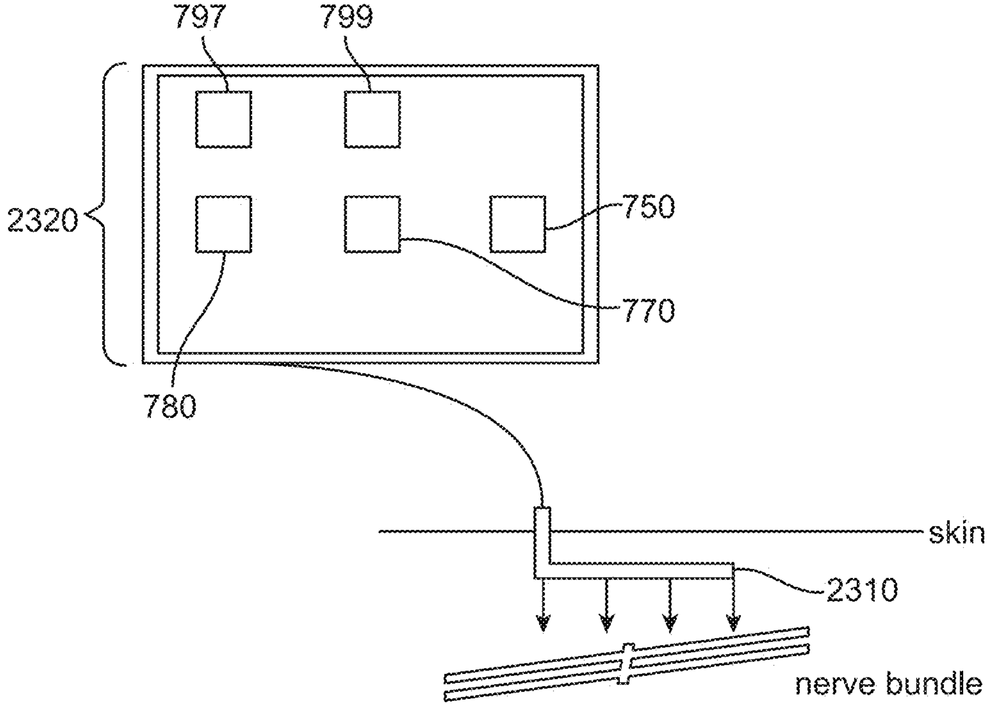
FIG. 23 is a drawing showing an embodiment where the stimulator is an electrode implanted at least partially subdermally.
Figure 24C:
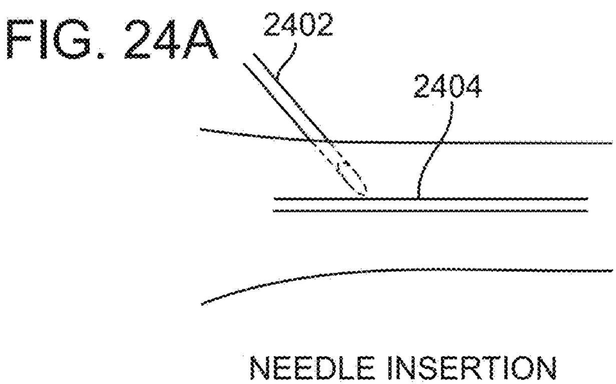
Figure 24C:
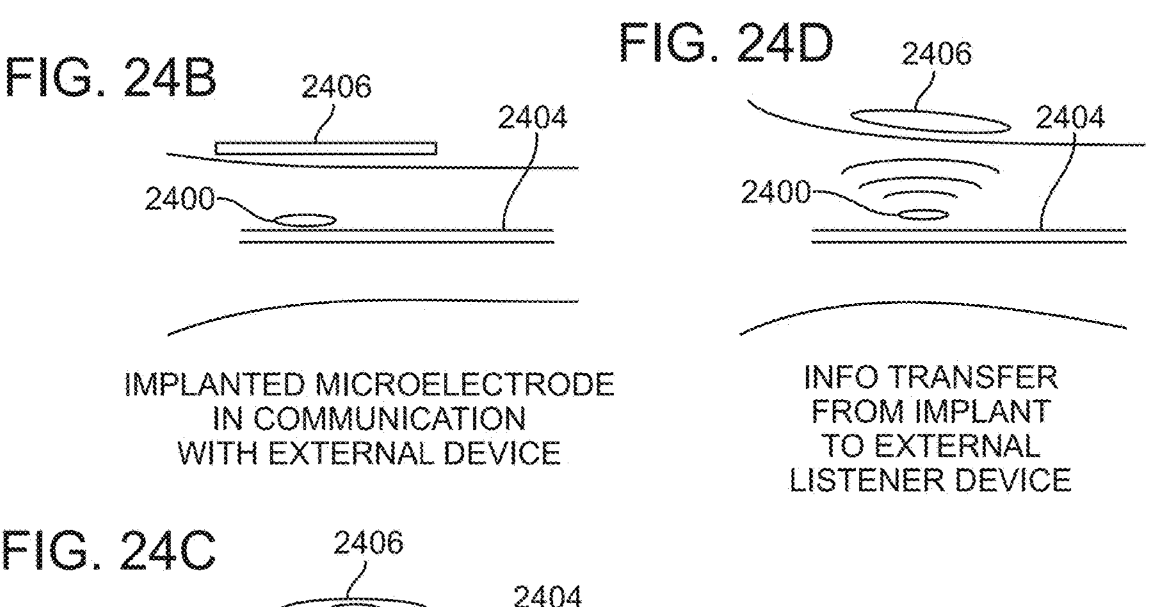

As shown in FIG. 23, a preferred embodiment of a controllable device for a user to reduce essential tremor comprises electrodes 2310 made from biocompatible materials implanted at least partially sub-dermally to stimulate targeted nerves; an external operating unit 2320, which contains a user controls interface, connected by leads to the implanted electrode 2310.

The device may contain further elements which may include a processor 797 that performs computations and controls other components; a processor controlled function generator; a digital library 799 stored on the processor or memory which contains preloaded modulation protocols; a sensor 780 connected to or in communication with the processor 797 which detects predefined parameters and transmits that parameter information to the processor; a data storage unit 770 connected to the sensor and processor; and a power supply 750.

In this embodiment, the implanted electrodes 2310 may function to provide direct electrical stimulation to the targeted nerves. Since the electrodes are implanted at least partially into the body and will remain an extended period of time (preferably several years), the electrodes may be made of material that has suitable electrical properties and is biocompatible. The electrode 2310 material is preferably selected from a group including silicones, PTFE, parylene, polyimide, polyesterimide, platinum, ceramic, and gold, or of natural materials such as collagen or hyaluronic acid. The electrodes 2310 can be of varying shape and size but importantly contact the nerves of interest. Electrode shapes include planar shanks, simple uniform microwires, and probes that taper to a thin tip from a wider base. The electrode may have a proximal end and a distal end. The distal end, may contact the nerves, and be adapted to deliver neural stimulation pulses to the selected nerves. The proximal end of the lead may be adapted to connect to the external operating unit run by a processor 797.

In a variation of the embodiment, there may be multiple leads connected to different nerve bundles. In another variation, there may be wireless communication with the implant as shown in FIGS. 24A-24D. The implant 2400, which can be a microelectrode or microstimulator, can be inserted proximate the nerve using needle insertion. The needle 2402 can be inserted into the patient next to or near the target nerve 2404, and then the implant can be ejected from the needle. The implant 2400 can be in communication with, transfer and receive data with, and be powered by an externally located device 2406, such as a decision unit described herein.

In one embodiment, the Interface may be an implanted nerve cuff. The cuff may either fully or partially encircle the nerve. The cuff may be attached to the nerve by means of closing butterfly arm electrodes. In another embodiment, the Interface may be a nerve abutment. The abutment may be in close proximity to the nerve or may lie along the nerve. The function of the cuff may be to provide good contact or close proximity between the device and the nerve. In another embodiment, the Interface may be anchored on the nerve or sheath around the nerve. For example, the device may be wrapped around, tied to, clamped to, tethered with small barbs to or chemically fused to the nerve or nerve sheath. The function of the cuff, coil, abutment or anchor is to provide good contact or close proximity between the device and the nerve. Some of these embodiments are depicted in FIGS. 25A-25F.

For example, FIGS. 25A-25C illustrate an embodiment of a coil electrode interface, which can be a multi-coil electrode, as shown, or a single coil electrode. In some embodiments, the coil electrode 2500 can be made of a shape memory material, such as nitinol, and can have a relaxed, straight configuration before insertion and implantation, and a coiled configuration after exposure to body temperature. FIGS. 25D and 25E illustrate embodiments of butterfly cuff type electrodes 2510, which may at least partially encircle the nerve. As in other embodiments, the interface can include single or multiple electrodes, and can be fabricated from a shape memory material to have an open configuration during delivery and a closed configuration wrapped around the nerve after implantation. FIG. 25F illustrates an embodiment of an interface having a linear array of electrodes 2520 that can abut against and lie along the nerve.

The method of inserting the implant may involve local or general anesthesia. The implant may be delivered through one or more punctures in the skin, such as a needle or suture, or it may be an open incision made in the skin to access the target area, or it could include both methods. In one embodiment, the device may be implanted by threading all or part of the device around the nerve and or surrounding tissue, such as blood vessels or tendons.

In one embodiment, the implant may include two electrodes positioned along a vascular pathway. The pathway may be along the palmar arch and the electrodes may be positioned in the brachial and axillary arteries. The fluid column between the electrodes may carry electricity and stimulate adjacent nerves. The electrodes may be either internal to the vascular pathway, like a stent, or external to the vascular pathway similar to a vascular wrap. In one embodiment, the device may be an implant capable of two-way communication with an external device. The embodiment may contain memory. The external "listener" device may also be a power source. The implant could communicate information such as its power reserves or usage history to the "listener". In another embodiment, the device is an implant capable of sensing activity on the nerve or adjacent nerves and reporting this information to the listener.

In another embodiment, the device or devices used to place the device may use ultrasound for guidance. Ultrasound may be used to measure proximity to blood vessels, nerves or other tissues, or to characterize the type and location of adjacent tissues.

In another embodiment, the electrodes for stimulation may be injected as a liquid. In another embodiment, the electrodes may be flexible and delivered in a viscous medium like hyaluronic acid. In another embodiment, the electrodes may be made of nitinol that takes its shape at 37 degrees Celsius. This would permit injecting or inserting the electrodes in one configuration, such as an elongated configuration to fit in a needle, and then would take their form when warmed to body temperature. Some of these examples are depicted in FIG. 25.

The implant may contain the necessary components for uni-directional or bi-directional communication between the implant, an external power transmission, a communication system, and/or electronics to store programmable stimulation parameters. The device may contain a wireless micromodule that receives command and power signals by radiofrequency inductive coupling from an external antenna. If the effector is electrical, the incoming communication channel may include information including the stimulation frequency, delay, pulsewidth and on/off intervals.

Transcutaneous charging or powering reduces the implant size by eliminating the need for a large power source (e.g. battery) and eliminates the need to replace the power source with repeat surgeries. An external component may be used to wirelessly power the internal component, such as by radiofrequency (RF) power transfer. For example, the external device may emit RF power that the internal component receives with a resonant coil. The power may be transmitted at a variety of wavelengths, including but not limited the radiofrequency and microwave spectrums, which range from 3 kHz to 300 GHz. Alternatively, the internal device may contain a battery. The external device may be worn or carried on the body, or it may be in the nearby surroundings such as on a nearby table or wall. It may be portable or fixed. The device may contain a capacitative energy storage module electrode that stimulates when it discharges. The electronics may be significantly simplified if the powering itself drives the stimulation profile. The capacitor blocks direct current while allowing alternating current to pass. When the capacitor reaches its dielectric breakdown, it discharges and releases a stimulation pulse.

The implant may also sense the tremor directly, such as by using electroneurography (ENG) or electromyography (EMG) signals or an accelerometer or a combination of the above. In this case, the implant may include multiple electrodes since microelectrodes and macroelectrodes are preferable for sensing and stimulating, respectively. The device may also include an outgoing communication channel to communicate the detected events.

Various embodiments of a tremor altering device and methods for using it have been disclosed above. These various embodiments may be used alone or in combination, and various changes to individual features of the embodiments may be altered, without departing from the scope of the invention. For example, the order of various method steps may in some instances be changed, and/or one or more optional features may be added to or eliminated from a described device. Therefore, the description of the embodiments provided above should not be interpreted as unduly limiting the scope of the invention as it is set forth in the claims.

Certain features that are described in this specification in the context of separate embodiments also can be implemented in combination in a single embodiment. Conversely, various features that are described in the context of a single embodiment also can be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

What is claimed is:

1. A method for transcutaneously stimulating peripheral nerves of a user, the method comprising:

calculating a fraction of a period of a tremor of the user;

delivering a first stimulus to a first peripheral nerve through a first peripheral nerve effector positioned on a first skin surface of the user to stimulate the first peripheral nerve; and delivering a second stimulus to a second peripheral nerve through a second peripheral nerve effector positioned on a second skin surface of the user to stimulate the second peripheral nerve;

wherein the second stimulus is offset in time from the first stimulus by the calculated fraction of the period of the tremor.

2. The method of claim 1, further comprising analyzing one or more characteristics of the tremor of the user by performing a frequency analysis of a spectral power of motion data on a predetermined length of time of the motion data, wherein the frequency analysis is restricted to between about 4 Hz to about 12 Hz, and wherein the first stimulus and the second stimulus comprise electrical stimuli.

3. The method of claim 1, wherein the calculated fraction is in a range of between one quarter of the tremor period and three quarters of the period of the tremor.

4. The method of claim 1, wherein the calculated fraction is one half of the period of the tremor.

5. The method of claim 1, wherein the first stimulus comprises a frequency of between 50 Hz to 300 Hz.

6. The method of claim 1, wherein the first stimulus comprises a frequency of below 50 Hz.

7. The method of claim 1, wherein calculating the fraction of the period of the tremor comprises performing a frequency analysis of a spectral power of motion data.

8. The method of claim 1, wherein the first skin surface is located at an extremity of the user.

9. The method of claim 8, wherein the extremity comprises a wrist.

10. The method of claim 1, wherein the first peripheral nerve is selected from the group comprising: a median nerve, a radial nerve, and an ulnar nerve.

11. The method of claim 1, wherein the second peripheral nerve is selected from the group comprising: a median nerve, a radial nerve, and an ulnar nerve.

12. The method of claim 1, wherein the first peripheral nerve is a median nerve and wherein the second peripheral nerve is a radial or ulnar nerve.

13. The method of claim 1, wherein at least one of the first stimulus and the second stimulus is a vibratory stimulus.

14. A method for transcutaneously stimulating peripheral nerves of a user, the method comprising:

delivering a first stimulus to a first peripheral nerve through a first peripheral nerve effector positioned on a first portion of a skin surface of the user to stimulate the first peripheral nerve; and delivering a second stimulus to a second peripheral nerve through a second peripheral nerve effector positioned on a second portion of the skin surface of the user to stimulate the second peripheral nerve, wherein the second stimulus is offset in time from the first stimulus by a fraction of a period of a tremor, wherein the fraction is selected from the group consisting of one half of the period of the tremor, one quarter of the period of the tremor, and three fourths of the period of the tremor.

15. The method of claim 14, further comprising repeating the first stimulus and the second stimulus in cycles, wherein the first stimulus and the second stimulus comprise electrical stimuli.

16. The method of claim 14, wherein the fraction is selected from the group consisting of: one half of the tremor period and one quarter of the period of the tremor.

17. The method of claim 14, further comprising repeating the first stimulus and the second stimulus in cycles.

18. The method of claim 14, wherein the skin surface is located at a wrist of the user.

19. The method of claim 14, wherein at least one of the first stimulus and the second stimulus is a vibratory stimulus.

20. The method of claim 14, wherein the first peripheral nerve is a median nerve and wherein the second peripheral nerve is a radial or ulnar nerve.

* * * * *